United States Patent
Wang et al.

(10) Patent No.: US 11,459,334 B2
(45) Date of Patent: Oct. 4, 2022

(54) SUBSTITUTED PYRROLO[2,1-F][1,2,4]TRIAZINES AS KIT AND/OR PDGFR-α INHIBITORS

(71) Applicant: SHENZHEN TARGETRX, INC., Guangdong (CN)

(72) Inventors: Yihan Wang, Guangdong (CN); Huanyin Li, Shenzhen (CN)

(73) Assignee: Shenzhen TargetRx, Inc., Guangdong (CN)

( * ) Notice: Subject to any disclaimer, the term of this patent is extended or adjusted under 35 U.S.C. 154(b) by 58 days.

(21) Appl. No.: 17/044,697

(22) PCT Filed: Apr. 15, 2019

(86) PCT No.: PCT/CN2019/082618
§ 371 (c)(1),
(2) Date: Oct. 1, 2020

(87) PCT Pub. No.: WO2019/201194
PCT Pub. Date: Oct. 24, 2019

(65) Prior Publication Data
US 2021/0040101 A1   Feb. 11, 2021

(30) Foreign Application Priority Data

Apr. 16, 2018   (CN) .......................... 201810339098.1

(51) Int. Cl.
*A61K 31/53* (2006.01)
*C07D 487/04* (2006.01)
(52) U.S. Cl.
CPC .................. *C07D 487/04* (2013.01)
(58) Field of Classification Search
CPC ............................. A61K 31/53; C07D 487/04
USPC ........................................... 514/243; 544/184
See application file for complete search history.

(56) References Cited

U.S. PATENT DOCUMENTS

| | | | | |
|---|---|---|---|---|
| 6,221,335 B1 * | 4/2001 | Foster | ............... | C07B 59/002 424/1.81 |
| 6,440,710 B1 * | 8/2002 | Keinan | ............... | C12P 13/02 435/188.5 |
| 6,603,008 B1 * | 8/2003 | Ando | ............... | A61P 25/00 546/271.4 |
| 7,517,990 B2 * | 4/2009 | Ito | ............... | C07D 233/56 546/184 |
| 9,200,002 B2 * | 12/2015 | Hodous | ............... | A61P 1/04 |
| 2007/0082929 A1 * | 4/2007 | Gant | ............... | A61P 1/04 546/273.7 |
| 2007/0197695 A1 * | 8/2007 | Potyen | ............... | C08K 5/55 524/110 |
| 2020/0325141 A1 | 10/2020 | Dineen et al. | | |

FOREIGN PATENT DOCUMENTS

| | | |
|---|---|---|
| CN | 101007814 | 8/2007 |
| CN | 102171211 | 8/2011 |
| CN | 105308036 | 2/2016 |
| CN | 105658652 | 6/2016 |
| CN | 106188072 | 12/2016 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Kilpatrick Townsend & Stockton LLP

(57) ABSTRACT

Provided in the present invention are a substituted pyrrolotriazine compound, a pharmaceutical composition thereof and a use thereof, the pyrrolotriazine compound being a compound represented by formula (I), or a pharmaceutically acceptable salt, prodrug, hydrate or solvent compound, crystalline form, stereoisomer or isotope variant thereof. The compound and composition of the present invention may be used in the treatment of conditions associated with KIT and/or PDGFRα.

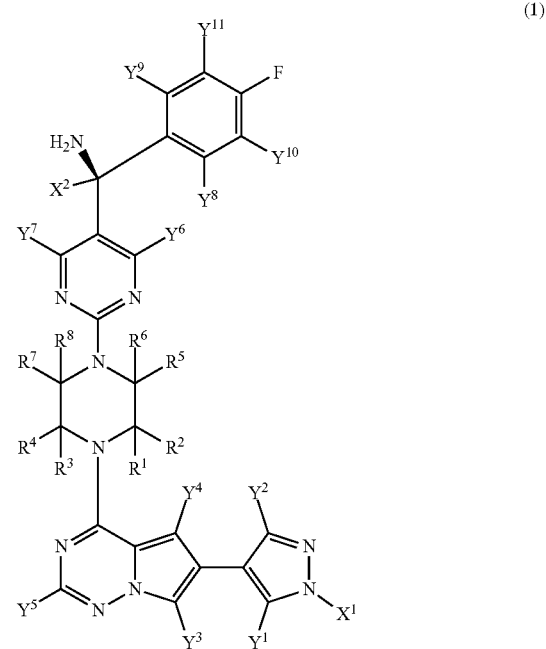

(I)

13 Claims, No Drawings

(56) References Cited

FOREIGN PATENT DOCUMENTS

| JP | 2016-538257 A | 12/2016 |
| WO | 0071129 | 11/2000 |
| WO | 2014039714 | 3/2014 |
| WO | 2014100620 | 6/2014 |
| WO | 2015057873 | 4/2015 |
| WO | 2016144844 | 9/2016 |
| WO | 2017072335 | 5/2017 |
| WO | 2017219800 | 12/2017 |

OTHER PUBLICATIONS

Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Dyck, et al. Journal of Neurochemistry, 46(2), 1986, 399-404.*
Kushner, et al. Canadian Journal of Physiology and Pharmacology, 77(2), 1999, 79-88.*
Tonn, et al. Biological Mass Spectrometry, 22(11), 1993, 633-642.*
Wolen. Journal of Clinical Pharmacology, 26, 1986, 419-424.*
Browne. Journal of Clinical Pharmacology, 38, 1998, 213-220.*
Pieniaszek, et al. in Journal of Clinical Pharmacology, 39, 1999, 817-825.*
Chinese Application No. CN201910297549.4, Office Action dated Dec. 16, 2019, 8 pages.
Chinese Application No. CN201910297549.4, Office Action dated Aug. 3, 2020, 7 pages.
Evans et al., A Precision Therapy Against Cancers Driven by Kit/pdgfra Mutations, Science Transitional Medicines, vol. 9, No. 414, Nov. 1, 2017.
Kettle et al., Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors, Journal of Medicinal Chemistry, vol. 61, No. 19, Sep. 11, 2018, 57 pages.
International Application No. PCT/CN2019/082618, International Search Report and Written Opinion dated Jul. 24, 2019, 8 pages.
Haodan et al., "Biomedical Marker Techniques", People's Medical Publishing House Co., Ltd., Dec. 31, 1995, pp. 312-317.
Office Action in JP 2020-554886, dated Nov. 9, 2021, 4 pages.
Amendment filed in JP 2016-538257, filed Nov. 24, 2017, 46 pages.
Supplemental European Search Report in 19789509.7, dated Nov. 9, 2021, 7 pages.
Anonymous, "Deuterated Drug—Wikipedia" Mar. 7, 2018, retrieved from the internet: URL:https://web.archive.org/web/20180307233020/ https://en.wikipedia.org/wiki/De uterated_drug, 1-13.
Office Action in JP2022-554886, dated May 4, 2022, 2 pages.

* cited by examiner

SUBSTITUTED PYRROLO[2,1-F][1,2,4]TRIAZINES AS KIT AND/OR PDGFR-α INHIBITORS

TECHNICAL FIELD

The invention belongs to the technical field of medicine, and in particular relates to a substituted pyrrolotriazine compound and a pharmaceutical composition containing the compound and its use. More specifically, the present invention relates to certain deuterium-substituted 1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethylamine or its stereoisomers. These deuterium-substituted compounds and the compositions thereof can be used to treat diseases related to KIT and/or PDGFRα, and these deuterium-substituted compounds have better pharmacokinetic properties.

BACKGROUND OF THE INVENTION

The receptor tyrosine kinase KIT (also known as CD117) is a type of transmembrane receptor protein with tyrosine kinase activity encoded by the retroviral proto-oncogene KIT. KIT kinase is composed of extracellular domain, transmembrane domain and intracellular domain. KIT ligand is a stem cell factor (SCF), which binds to the extracellular domain of KIT to induce receptor dimerization and activate downstream signaling pathways. KIT mutations usually appear in the DNA (exon 11) encoding the domains near the membrane region. They also appear in exons 7, 8, 9, 13, 14, 17, and 18 at a lower frequency. The mutation makes KIT function independent of SCF activation, leading to a high cell division rate and possible genome instability. Mutant KIT has been implicated in the pathogenesis of several diseases and conditions, including Systemic Mastocytosis (SM), Gastrointestinal Stromal Tumors (GIST), Acute Myeloid (Myelocytic) Leukemia (AML), melanoma and seminoma. Therefore, there is a need to develop therapeutic agents that inhibit KIT, and particularly drugs that inhibit mutant KIT.

Platelet Derived Growth Factor Receptor is a cell surface tyrosine kinase receptor of members of the platelet-derived growth factor (PDGF) family. PDGF subunits, PDGFα and PDGFβ, are important factors that regulate cell proliferation, cell differentiation, cell growth, development and many diseases including cancer. The PDGFRα D842V mutation has been found in different subsets of gastrointestinal stromal tumors (GIST), usually from the stomach. The D842V mutation is known to be associated with tyrosine kinase inhibitor resistance.

Gastrointestinal stromal tumor (GIST) is a rare cancer that arises from the Cajal interstitial cells or common precursor cells, and is caused by the tyrosine kinase receptor KIT (CD117) or platelet-derived growth factor receptor alpha polypeptide (PDGFRα) mutations. 80%-85% of GISTs are caused by KIT gene mutations, involving exon 11, exon 9, exon 13, and exon 17 and other rare mutation sites; and PDGFRα gene mutations account for 5% to 10%, and they are usually found in exon 18 and exon 12.

Avapritinib (also known as BLU-285, chemical name being (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethylamine, having the following structural formula) is an oral small molecule drug developed by Blueprint Medicines Corporation, which is a highly selective inhibitor of PDGFRα and KIT. It has activity against KIT and PDGFRα mutations (including KIT D816V, PDGFRα D842V and KIT exon 17 mutations, etc.), and is currently in Phase I clinical. In June of 2017, Avapritinib received FDA breakthrough therapy designation for the treatment of patients with unresectable or metastatic GIST with PDGFRα D842V mutation. Previously, FDA granted Avapritinib orphan drug designation for the treatment of gastrointestinal stromal tumor (GIST) and systemic mastocytosis (SM).

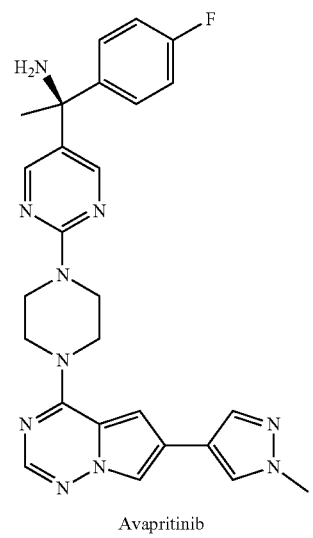

Avapritinib

It is known that poor absorption, distribution, metabolism, and/or excretion (ADME) properties are the main reason for the failure of many drug candidates in clinical trials. Many drugs currently on the market also have limited application fields due to their poor ADME properties. The rapid metabolism of agents will lead to many agents that could have been effective in treating diseases but are hard to be real drugs because of too rapid removal from the body. Although frequent or high-dose administration may solve the problem of rapid drug clearance, this method will bring about problems such as poor patient compliance, side effects caused by high-dose medication, and increased treatment costs. In addition, rapidly metabolizing drugs may also expose patients to undesirable toxic or reactive metabolites.

Although Avapritinib as a highly selective PDGFRα and KIT inhibitor can effectively treat GIST and SM, there are still serious clinical unmet needs in this field, and it is still challenging work to find novel compounds that can treat KIT and/or PDGFRα-mediated diseases, have good oral bioavailability, and can be made into medicaments. Therefore, there is still a need in the art to develop compounds that have selective inhibitory activity as therapeutic agents against mutant KIT and/or PDGFRα-mediated diseases and/or better pharmacodynamics/pharmacokinetics that are suitable as. The present invention provides such compounds

SUMMARY OF THE INVENTION

In view of the above technical problems, the present invention discloses a new deuterium-substituted pyrrolotriazine compound and its composition and use, which compound has better KIT and/or PDGFRα kinase inhibitory activity, high selectivity for drug resistant mutation KIT Exon 17 mutation, KIT D816V, or PDGFRα D842V, or all the three mutations, lower side effects, and better pharmacokinetic properties, and can be used to treat systemic mastocytosis (SM), gastrointestinal stromal tumor (GIST), and acute myeloid leukemia (AML).

As used herein, the term "compound of the present invention" refers to a compound represented by formula (I). The term also includes pharmaceutically acceptable salts, prodrugs, hydrates or solvates, polymorphs, stereoisomers or isotopic variants of the compounds of formula (I).

In this regard, the present invention adopts the following technical solutions:

The first aspect of the present invention provides a compound of formula (Φ):

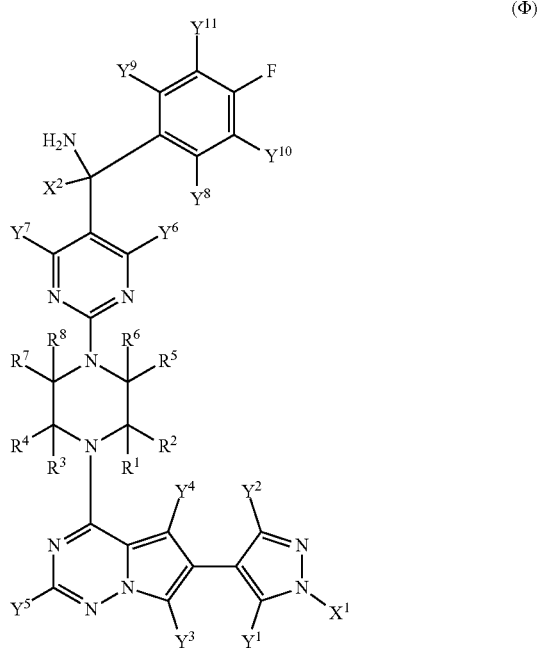

wherein $R^1$, $R^2$, $R^3$, $R^4$, $R^5$, $R^6$, $R^7$, and $R^8$ are each independently selected from hydrogen or deuterium;

$X^1$ and $X^2$ are each independently selected from $CH_3$, $CD_3$, $CHD_2$, or $CH_2D$;

$Y^1$, $Y^2$, $Y^3$, $Y^4$, $Y^5$, $Y^6$, $Y^7$, $Y^8$, $Y^9$, $Y^{10}$, and $Y^{11}$ are each independently selected from hydrogen, deuterium, halogen or trifluoromethyl;

provided that the compound of the above formula contains at least one deuterium atom; or a pharmaceutically acceptable salt, prodrug, hydrate or solvate, polymorph, stereoisomer or isotopic variant thereof.

In another aspect, the invention provides a pharmaceutical composition containing the compound of the invention and a pharmaceutically acceptable excipient. In a specific embodiment, the compound of the invention is provided in an effective amount in the pharmaceutical composition. In a specific embodiment, the compound of the invention is provided in a therapeutically effective amount. In a specific embodiment, the compound of the invention is provided in a prophylactically effective amount. In a specific embodiment, the pharmaceutical composition further contains another therapeutic agent, which has activity on the mutant KIT with a mutation in exon 9 or exon 11.

In another aspect, the present invention provides a method for preparing a pharmaceutical composition as described above, which comprises the following steps: mixing a pharmaceutically acceptable excipient with a compound of the present invention to form the pharmaceutical composition.

In another aspect, the present invention also relates to providing a method of treating a KIT-mediated disease in a subject. The method comprises administering to the subject a therapeutically effective amount of a compound or pharmaceutical composition of the invention. In a specific embodiment, the KIT has a mutation in exon 9. In a specific embodiment, the KIT has a mutation in exon 11. In a specific embodiment, the KIT has a mutation in exon 17. In a specific embodiment, the KIT has a mutation at residue 816. In a specific embodiment, the compound is administered orally, subcutaneously, intravenously, or intramuscularly. In a specific embodiment, the compound is administered for a long period. In a specific embodiment, the KIT-mediated disease is mastocytosis, gastrointestinal stromal tumor or acute myeloid leukemia.

In another aspect, the present invention also relates to providing a method of treating a disease mediated by mutant PDFGRα in a subject. The method comprises administering to the subject a therapeutically effective amount of a compound or pharmaceutical composition of the invention. In a specific embodiment, PDFGRα has a mutation in exon 18. In a specific embodiment, PDFGRα has a mutation at residue 842. In a specific embodiment, the compound is administered orally, subcutaneously, intravenously, or intramuscularly. In a specific embodiment, the compound is administered for a long period. In a specific embodiment, the disease mediated by mutant PDFGRα is mastocytosis, gastrointestinal stromal tumor or acute myeloid leukemia.

From the following specific embodiments, examples and claims, other objects and advantages of the present invention will be apparent to those skilled in the art.

Definition

Herein, unless otherwise specified, "deuterated" means that one or more hydrogen atoms in a compound or group are replaced by deuterium; and may be mono-, di-, multi-, or fully-substituted. The terms "mono- or multi-deuterated" and "substituted by one or more deuterium" are used interchangeably.

Herein, unless otherwise specified, "non-deuterated compound" refers to a compound that contains a proportion of deuterium atoms not higher than the content of natural deuterium isotope (0.015%).

The term "pharmaceutically acceptable salt" means, within the scope of reliable medical judgment, those salts suitable for contact with tissues of human and lower animal without excessive toxicity, irritation, allergic reactions, etc., and commensurate with a reasonable benefit/risk ratio. Pharmaceutically acceptable salts are well known in the art. For example, Berge et al. described the pharmaceutically acceptable salts in details in J. Pharmaceutical Sciences (1977) 66:1-19. Pharmaceutically acceptable salts of the compounds of the invention include those derived from suitable inorganic and organic acids and bases.

The compounds of the present invention may be in an amorphous or crystalline form. In addition, the compounds of the present invention may exist in one or more crystalline forms. Therefore, the present invention includes all amorphous or crystalline forms of the compounds of the present invention within its scope. The term "crystalline form" refers to the different arrangements of chemical drug molecules, which are generally exhibited as the forms of existence of the drug material in the solid state. A drug can exist in multiple crystalline forms, and different crystalline forms of the same drug may have different dissolution and absorption properties in the body, thereby affecting the dissolution and release of the preparation.

The term "crystalline form" refers to the different arrangements of chemical drug molecules, which are generally exhibited as the forms of existence of the drug material in the solid state. A drug can exist in multiple crystalline forms, and different crystalline forms of the same drug may have different dissolution and absorption properties in the body, thereby affecting the dissolution and release of the preparation.

As used herein, the term "subject" includes, but is not limited to: humans (i.e., men or women of any age group, for example, pediatric subjects (e.g., infants, children, adolescents) or adult subjects (e.g., young adults, middle-aged adults or older adults)) and/or non-human animals, for example, mammals, for example, primates (for example, cynomolgus monkeys and rhesus monkeys), cattle, pigs, horses, sheep, goats, rodents, cats and/or dogs. In some embodiments, the subject is a human. In other embodiments, the subject is a non-human animal.

"Disease", "disorder" and "condition" are used interchangeably herein.

Unless otherwise specified, the term "treatment" as used herein includes the effect that occurs when a subject suffers from a specific disease, disorder, or condition, and reduces the severity of the disease, disorder, or condition, or delays or slows the development of the disease, disorder, or condition ("therapeutic treatment"), and also includes the effect that occurs before the subject starts suffering from a specific disease, disorder or condition ("preventive treatment").

Generally, the "effective amount" of a compound refers to an amount sufficient to cause a desired biological response. As understood by those of ordinary skill in the art, the effective amount of the compound of the present invention may vary according to the following factors: for example, the biological objectives, the pharmacokinetics of the compound, the disease to be treated, the mode of administration, and the age, health conditions and symptoms of the subject. The effective amount includes therapeutically and prophylactically effective amounts.

Unless otherwise specified, the "therapeutically effective amount" of the compound used herein is an amount sufficient to provide therapeutic benefit during the treatment of a disease, disorder, or condition, or delay or minimize one or more symptoms related to the disease, disorder, or condition. The therapeutically effective amount of a compound refers to the amount of a therapeutic agent used alone or in combination with other therapies, which provides therapeutic benefits in the process of treating a disease, disorder, or condition. The term "therapeutically effective amount" can include an amount that improves overall treatment, reduces or avoids the symptoms or causes of a disease or disorder, or enhances the therapeutic efficacy of other therapeutic agents.

Unless otherwise specified, the "prophylactically effective amount" of the compound used herein is an amount sufficient to prevent a disease, disorder, or condition, prevent one or more symptoms related to a disease, disorder, or condition, or prevent recurrence of a disease, disorder, or condition. The prophylactically effective amount of a compound refers to the amount of a therapeutic agent used alone or in combination with other agents, which provides a preventive benefit in the process of preventing a disease, disorder or condition. The term "prophylactically effective amount" may include an amount that improves overall prevention, or an amount that enhances the preventive efficacy of other preventive agents.

"Combination" and related terms refer to the simultaneous or sequential administration of the therapeutic agents of the present invention. For example, the compound of the present invention may be administered simultaneously or sequentially with another therapeutic agent in separate unit dosage forms, or administered simultaneously with another therapeutic agent in a single unit dosage form.

DETAILED DESCRIPTION OF THE INVENTION

Compound

Herein, "the compound of the present invention" refers to the following compounds of formula (Φ), formula (I) and formula (II), or pharmaceutically acceptable salts, enantiomers, diastereomers, racemates, solvates, hydrates, polymorphs, prodrugs or active metabolites.

In one embodiment, the present invention relates to a compound of formula (Φ):

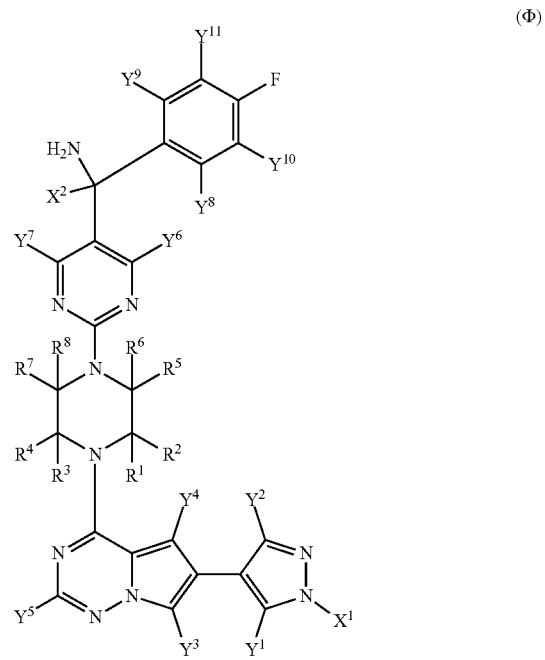

wherein $R^1$, $R^2$, $R^3$, $R^4$, $R^5$, $R^6$, $R^7$, and $R^8$ are each independently selected from hydrogen or deuterium;

$X^1$ and $X^2$ are each independently selected from $CH_3$, $CD_3$, $CHD_2$, or $CH_2D$;

$Y^1$, $Y^2$, $Y^3$, $Y^4$, $Y^5$, $Y^6$, $Y^7$, $Y^8$, $Y^9$, $Y^{10}$, and $Y^{11}$ are each independently selected from hydrogen, deuterium, halogen or trifluoromethyl;

provided that the compound of the above formula contains at least one deuterium atom; or a pharmaceutically acceptable salt, prodrug, hydrate or solvate, polymorph, stereoisomer or isotopic variant thereof.

In another embodiment, the present invention relates to the aforementioned compound, which is of formula (I) or formula (II):

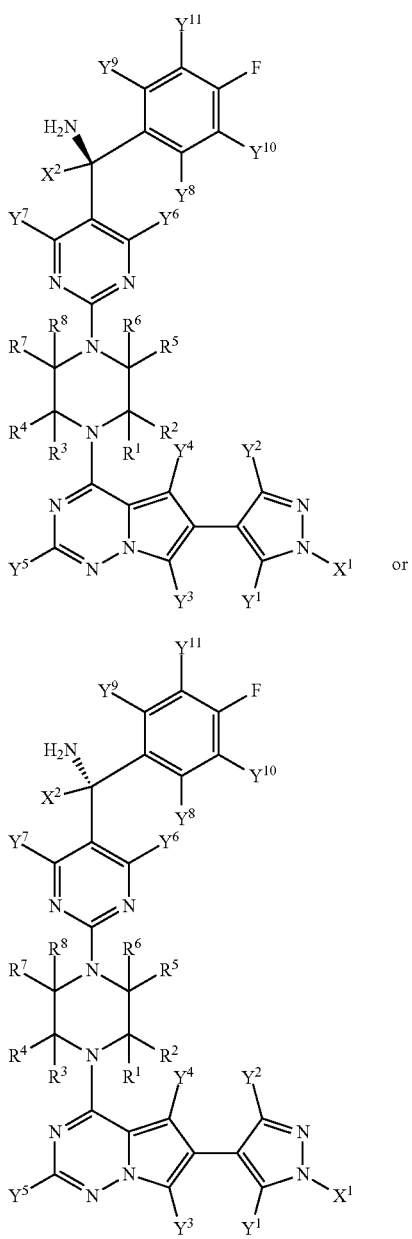

wherein
$R^1$, $R^2$, $R^3$, $R^4$, $R^5$, $R^6$, $R^7$, and $R^8$ are each independently selected from hydrogen or deuterium;

$X^1$ and $X^2$ are each independently selected from $CH_3$, $CD_3$, $CHD_2$, or $CH_2D$;

$Y^1$, $Y^2$, $Y^3$, $Y^4$, $Y^5$, $Y^6$, $Y^7$, $Y^8$, $Y^9$, $Y^{10}$, and $Y^{11}$ are each independently selected from hydrogen, deuterium, halogen or trifluoromethyl;

provided that the compound of the above formula contains at least one deuterium atom; or a pharmaceutically acceptable salt, prodrug, hydrate or solvate, polymorph, stereoisomer or isotopic variant thereof.

In a specific embodiment, the deuterium isotope content in the deuterated position is at least greater than the natural deuterium isotope content, 0.015%, preferably 30% greater, more preferably 50% greater, more preferably 75% greater, more preferably 95% greater, more than 99% greater than the natural deuterium isotope content.

Specifically, in the present invention, for $R^1$, $R^2$, $R^3$, $R^4$, $R^5$, $R^6$, $R^7$, $R^8$, $Y^1$, $Y^2$, $Y^3$, $Y^4$, $Y^5$, $Y^6$, $Y^7$, $Y^8$, $Y^9$, $Y^{10}$, $Y^{11}$, $X^1$, and $X^2$, the deuterium isotope content in each deuterated position is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In a specific embodiment, "$R^1$, $R^2$, $R^3$, $R^4$, $R^5$, $R^6$, $R^7$, and $R^8$ are each independently selected from hydrogen or deuterium" includes the embodiment where $R^1$ is selected from hydrogen or deuterium, the embodiment where $R^2$ is selected from hydrogen or deuterium, the embodiment where $R^3$ is selected from hydrogen or deuterium, and so on, until the embodiment where $R^8$ is selected from hydrogen or deuterium. More specifically, it includes the embodiment where $R^1$ is hydrogen or $R^1$ is deuterium, the embodiment where $R^2$ is hydrogen or $R^2$ is deuterium, the embodiment where $R^3$ is hydrogen or $R^3$ is deuterium, and so on, until the embodiment where $R^8$ is hydrogen or $R^8$ is deuterium.

In another specific embodiment, "$X^1$ and $X^2$ are each independently selected from $CH_3$, $CD_3$, $CHD_2$, or $CH_2D$" includes the embodiment where $X^1$ is selected from $CH_3$, $CD_3$, $CHD_2$, or $CH_2D$ and the embodiment where $X^2$ is selected from $CH_3$, $CD_3$, $CHD_2$, or $CH_2D$. More specifically, it includes the embodiment where $X^1$ is $CH_3$, $X^1$ is $CD_3$, $X^1$ is $CHD_2$, or $X^1$ is $CH_2D$ and the embodiment where $X^2$ is $CH_3$, $X^2$ is $CD_3$. $X^2$ is $CHD_2$, or $X^2$ is $CH_2D$.

In another specific embodiment, "$Y^1$, $Y^2$, $Y^3$, $Y^4$, $Y^5$, $Y^6$, $Y^7$, $Y^8$, $Y^9$, $Y^{10}$, and $Y^{11}$ are each independently selected from hydrogen, deuterium, halogen or trifluoromethyl" includes the embodiment where $Y^1$ is selected from hydrogen, deuterium, halogen or trifluoromethyl, the embodiment where $Y^2$ is selected from hydrogen, deuterium, halogen or trifluoromethyl, the embodiment where $Y^3$ is selected from hydrogen, deuterium, halogen or trifluoromethyl, and so on, until the embodiment where $Y^{11}$ is selected from hydrogen, deuterium, halogen or trifluoromethyl. More specifically, it includes the embodiment where $Y^1$ is hydrogen, $Y^1$ is deuterium, $Y^1$ is halogen (F, Cl, Br, or I) or $Y^1$ is trifluoromethyl; the embodiment where $Y^2$ is hydrogen, $Y^2$ is deuterium, $Y^2$ is halogen (F, Cl, Br, or I) or $Y^2$ is trifluoromethyl; the embodiment where $Y^3$ is hydrogen, $Y^3$ is deuterium, $Y^3$ is halogen (F, Cl, Br, or I) or $Y^3$ is trifluoromethyl; and so on, until the embodiment where $Y^{11}$ is hydrogen, $Y^{11}$ is deuterium. $Y^{11}$ is halogen (F, Cl, Br, or I) or $Y^{11}$ is trifluoromethyl.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are each independently selected from hydrogen or deuterium, and $R^1$-$R^8$, $X^1$ and $X^2$ are as described above, provided that the compound contains at least one deuterium atom.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are each independently selected from hydrogen or deuterium, $R^1$-$R^8$ are each independently selected from hydrogen or deuterium, and $X^1$ and $X^2$ are each independently selected from $CH_3$ or $CD_3$, provided that the compound contains at least one deuterium atom.

In another specific embodiment, the present invention relates to a compound of formula (4), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^8$ are each independently selected from hydrogen or deuterium, and $X^1$ and $X^2$ are each independently selected from $CH_3$, $CD_3$, $CHD_2$, or $CH_2D$, provided that the compound contains at least one deuterium atom.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^8$ are each independently selected from hydrogen or deuterium, and $X^1$ and $X^2$ are each independently selected from $CH_3$ or $CD_3$, provided that the compound contains at least one deuterium atom.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^4$ are all hydrogen or deuterium, $R^5$-$R^8$ are all hydrogen or deuterium, and $X^1$ and $X^2$ are each independently selected from $CH_3$ or $CD_3$, provided that the compound contains at least one deuterium atom.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^4$ are all hydrogen, $R^5$-$R^8$ are all hydrogen or deuterium, and $X^1$ and $X^2$ are each independently selected from $CH_3$ or $CD_3$, provided that the compound contains at least one deuterium atom. More specifically, the invention includes the embodiment where $Y^1$-$Y^{11}$ are all hydrogen, $R^1$-$R^4$ are all hydrogen, $R^5$-$R^8$ are all hydrogen, $X^1$ is $CH_3$, and $X^2$ is $CD_3$, the embodiment where $Y^1$-$Y^{11}$ are all hydrogen, $R^1$-$R^4$ are all hydrogen, $R^5$-$R^8$ are all hydrogen, $X^1$ is $CD_3$, and $X^2$ is $CH_3$, the embodiment where $Y^1$-$Y^{11}$ are all hydrogen, $R^1$-$R^4$ are all hydrogen, $R^5$-$R^8$ are all hydrogen, $X^1$ is $CD_3$, and $X^2$ is $CD_3$, the embodiment where $Y^1$-$Y^{11}$ are all hydrogen, $R^1$-$R^4$ are all hydrogen, $R^5$-$R^8$ are all deuterium, $X^1$ is $CH_3$, and $X^2$ is $CH_3$, the embodiment where $Y^1$-$Y^{11}$ are all hydrogen, $R^1$-$R^4$ are all hydrogen. $R^5$-$R^8$ are all deuterium, $X^1$ is $CH_3$, and $X^2$ is $CD_3$, the embodiment where $Y^1$-$Y^{11}$ are all hydrogen, $R^1$-$R^4$ are all hydrogen, $R^5$-$R^8$ are all deuterium, $X^1$ is $CD_3$, and $X^2$ is $CH_3$, or the embodiment where $Y^1$-$Y^{11}$ are all hydrogen, $R^1$-$R^4$ are all hydrogen, $R^5$-$R^8$ are all deuterium, $X^1$ is $CD_3$, and $X^2$ is $CD_3$.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^4$ are all deuterium, $R^5$-$R^8$ are all hydrogen or deuterium, and $X^1$ and $X^2$ are each independently selected from $CH_3$ or $CD_3$. More specifically, the invention includes the embodiment where $Y^1$-$Y^{11}$ are all hydrogen, $R^1$-$R^4$ are all deuterium, $R^5$-$R^8$ are all hydrogen, $X^1$ is $CH_3$, and $X^2$ is $CH_3$, the embodiment where $Y^1$-$Y^{11}$ are all hydrogen, $R^1$-$R^4$ are all deuterium, $R^5$-$R^8$ are all hydrogen, $X^1$ is $CH_3$, and $X^2$ is $CD_3$, the embodiment where $Y^1$-$Y^{11}$ are all hydrogen, $R^1$-$R^4$ are all deuterium, $R^5$-$R^8$ are all hydrogen, $X^1$ is $CD_3$, and $X^2$ is $CH_3$, the embodiment where $Y^1$-$Y^{11}$ are all hydrogen, $R^1$-$R^4$ are all deuterium, $R^5$-$R^8$ are all hydrogen, $X^1$ is $CD_3$, and $X^2$ is $CD_3$, the embodiment where $Y^1$-$Y^{11}$ are all hydrogen, $R^1$-$R^4$ are all deuterium, $R^5$-$R^8$ are all deuterium, $X^1$ is $CH_3$, and $X^2$ is $CH_3$, the embodiment where $Y^1$-$Y^{11}$ are all hydrogen, $R^1$-$R^4$ are all deuterium, $R^5$-$R^8$ are all deuterium, $X^1$ is $CH_3$, and $X^2$ is CD %, the embodiment where $Y^1$-$Y^{11}$ are all hydrogen, $R^1$-$R^4$ are all deuterium, $R^5$-$R^8$ are all deuterium, $X^1$ is $CD_3$, and $X^2$ is $CH_3$, or the embodiment where $Y^1$-$Y^{11}$ are all hydrogen, $R^1$-$R^4$ are all deuterium. $R^5$-$R^8$ are all deuterium, $X^1$ is $CD_3$, and $X^2$ is $CD_3$. In another specific embodiment, the present invention relates to a compound of formula (N), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^8$ are all hydrogen or deuterium, and $X^1$ and $X^2$ are each independently selected from $CH_3$ or $CD_3$, provided that the compound contains at least one deuterium atom.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^8$ are all hydrogen, and $X^1$ and $X^2$ are each independently selected from $CH_3$ or $CD_3$, provided that the compound contains at least one deuterium atom. More specifically, the invention includes the embodiment where $Y^1$-$Y^{11}$ are all hydrogen, $R^1$-$R^8$ are all hydrogen, $X^1$ is $CH_3$, and $X^2$ is $CD_3$, the embodiment where $Y^1$-$Y^{11}$ are all hydrogen, $R^1$-$R^8$ are all hydrogen, $X^1$ is $CD_3$, and $X^2$ is $CH_3$, or the embodiment where $Y^1$-$Y^{11}$ are all hydrogen. $R^1$-$R^8$ are all hydrogen, $X^1$ is $CD_3$, and $X^2$ is $CD_3$.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $R^1$-$R^8$ are all deuterium, and $X^1$ and $X^2$ are each independently selected from $CH_3$ or $CD_3$. More specifically, the invention includes the embodiment where $Y^1$-$Y^{11}$ are all hydrogen, $R^1$-$R^8$ are all deuterium, $X^1$ is $CH_3$, and $X^2$ is $CH_3$, the embodiment where $Y^1$-$Y^{11}$ are all hydrogen, $R^1$-$R^8$ are all deuterium, $X^1$ is $CH_3$, and $X^2$ is $CD_3$, the embodiment where $Y^1$-$Y^{11}$ are all hydrogen, $R^1$-$R^8$ are all deuterium, $X^1$ is $CD_3$, and $X^2$ is $CH_3$, or the embodiment where $Y^1$-$Y^{11}$ are all hydrogen, $R^1$-$R^8$ are all deuterium, $X^1$ is $CD_3$, and $X^2$ is $CD_3$.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $X^1$ is $CH_3$, $R^1$-$R^4$ are all hydrogen or deuterium, $R^1$-$R^8$ are all hydrogen or deuterium, and $X^2$ is each independently selected from $CH_3$, or $CD_3$, provided that the compound contains at least one deuterium atom. More specifically, the invention includes the embodiment where $Y^1$-$Y^{11}$ are all hydrogen, $X^1$ is $CH_3$, $R^1$-$R^4$ are all hydrogen, $R^5$-$R^8$ are all deuterium, and $X^2$ is $CH_3$, the embodiment where $Y^1$-$Y^{11}$ are all hydrogen, $X^1$ is $CH_3$, $R^1$-$R^4$ are all hydrogen, $R^5$-$R^8$ are all deuterium, and $X^2$ is $CD_3$, the embodiment where $Y^1$-$Y^{11}$ are all hydrogen, $X^1$ is $CH_3$, $R^1$-$R^8$ are all deuterium, $R^5$-$R^8$ are all hydrogen, and $X^2$ is $CH_3$, the embodiment where $Y^1$-$Y^{11}$ are all hydrogen, $X^1$ is $CH_3$, $R^1$-$R^4$ are all deuterium, $R^5$-$R^8$ are all hydrogen, and $X^2$ is $CD_3$, the embodiment where $Y^1$-$Y^{11}$ are all hydrogen, $X^1$ is $CH_3$, $R^1$-$R^8$ are all hydrogen, and $X^2$ is $CD_3$, the embodiment where $Y^1$-$Y^{11}$ are all hydrogen, $X^1$ is $CH_3$, $R^1$-$R^8$ are all deuterium, and $X^2$ is $CH_3$, or the embodiment where $Y^1$-$Y^{11}$ are all hydrogen, $X^1$ is $CH_3$, $R^1$-$R^8$ are all deuterium, and $X^2$ is $CD_3$.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $X^1$ is $CD_3$, $R^1$-$R^8$ are each independently selected from hydrogen or deuterium, and $X^2$ is each independently selected from $CH_3$ or $CD_3$, provided that the compound contains at least one deuterium atom. More specifically, the invention includes the embodiment where $Y^1$-$Y^{11}$ are all hydrogen, $X^1$ is $CD_3$, $R^1$-$R^4$ are all hydrogen, $R^5$-$R^8$ are all deuterium, and $X^2$ is $CH_3$, the embodiment where $Y^1$-$Y^{11}$ are all hydrogen, $X^1$ is $CD_3$, $R^1$-$R^4$ are all hydrogen, $R^5$-$R^8$ are all deuterium, and $X^2$ is $CD_3$, the embodiment where $Y^1$-$Y^{11}$ are all hydrogen, $X^1$ is $CD_3$, $R^1$-$R^4$ are all deuterium, $R^5$-$R^8$ are all hydrogen, and $X^2$ is $CH_3$, the embodiment where $Y^1$-$Y^{11}$ are all hydrogen, $X^1$ is $CD_3$, $R^1$-$R^4$ are all deuterium, $R^5$-$R^8$ are all hydrogen, and $X^2$ is $CD_3$, the embodiment where $Y^1$-$Y^{11}$ are all hydrogen, $X^1$ is $CD_3$, $R^1$-$R^8$ are all hydrogen, and $X^2$ is $CH_3$, the embodiment where $Y^1$-$Y^{11}$ are all hydrogen, $X^1$ is $CD_3$, $R^1$-$R^8$ are all hydrogen, and $X^2$ is $CD_3$, the embodiment where $Y^1$-$Y^{11}$ are all hydrogen, $X^1$ is $CD_3$, $R^1$-$R^8$ are all deuterium, and $X^2$ is $CH_3$, or the embodiment where $Y^1$-$Y^{11}$ are all deuterium, $X^1$ is $CD_3$, $R^1$-$R^8$ are all hydrogen, and $X^2$ is $CD_3$.

In another specific embodiment, the present invention relates to a compound of formula (Φ), formula (I) or formula (I), or a pharmaceutically acceptable salt, prodrug, hydrate or solvate, polymorph, stereoisomer or isotopic variant thereof, wherein $Y^1$-$Y^{11}$ are all hydrogen, $X^2$ is $CH_3$, $R^1$-$R^8$ are each independently selected from hydrogen or deuterium, and $X^1$ is each independently selected from $CH_3$ or $CD_3$, provided that the compound contains at least one deuterium atom. More specifically, the invention includes the embodiment where $Y^1$-$Y^{11}$ are all hydrogen, $X^2$ is $CH_3$, $R^1$-$R^4$ are all hydrogen, $R^5$-$R^8$ are all deuterium, and $X^1$ is $CH_3$, the embodiment where $Y^1$-$Y^{11}$ are all hydrogen, $X^2$ is $CH_3$, $R^1$-$R^4$ are all hydrogen, $R^5$-$R^8$ are all deuterium, and $X^1$ is $CD_3$, the embodiment where $Y^1$-$Y^{11}$ are all hydrogen, $X^2$ is $CH_3$, $R^1$-$R^4$ are all deuterium, $R^5$-$R^8$ are all hydrogen, and $X^1$ is $CH_3$, the embodiment where $Y^1$-$Y^{11}$ are all hydrogen. $X^2$ is $CH_3$, $R^1$-$R^4$ are all deuterium, $R^5$-$R^8$ are all hydrogen, and $X^1$ is $CD_3$, the embodiment where $Y^1$-$Y^{11}$ are all hydrogen, $X^2$ is $CH_3$, $R^1$-$R^8$ are all hydrogen, and $X^1$ is $CD_3$, the embodiment where $Y^1$-$Y^{11}$ are all hydrogen, $X^2$ is $CH_3$, $R^1$-$R^8$ are all deuterium, and $X^1$ is $CH_3$, or the embodiment where $Y^1$-$Y^{11}$ are all hydrogen, $X^2$ is $CH_3$, $R^1$-$R^8$ are all deuterium, and $X^1$ is $CD_3$.

In another specific embodiment, the present invention relates to a compound of formula (Φ), formula (I) or formula (II), or a pharmaceutically acceptable salt, prodrug, hydrate or solvate, polymorph, stereoisomer or isotopic variant thereof, wherein $Y^1$-$Y^{11}$ are all hydrogen, $X^2$ is $CD_3$, $R^1$-$R^8$ are each independently selected from hydrogen or deuterium, and $X^1$ is each independently selected from $CH_3$ or $CD_3$, provided that the compound contains at least one deuterium atom. More specifically, the invention includes the embodiment where $Y^1$-$Y^{11}$ are all hydrogen, $X^2$ is $CD_3$, $R^1$-$R^4$ are all hydrogen, $R^5$-$R^8$ are all deuterium, and $X^1$ is $CH_3$, the embodiment where $Y^1$-$Y^{11}$ are all hydrogen, $X^2$ is $CD_3$, $R^1$-$R^4$ are all hydrogen, $R^5$-$R^8$ are all deuterium, and $X^1$ is $CD_3$, the embodiment where $Y^1$-$Y^{11}$ are all hydrogen, $X^2$ is $CD_3$, $R^1$-$R^4$ are all deuterium, $R^5$-$R^8$ are all hydrogen, and $X^1$ is $CH_3$, the embodiment where $Y^1$-$Y^{11}$ are all hydrogen, $X^2$ is $CD_3$, $R^1$-$R^4$ are all deuterium, $R^5$-$R^8$ are all hydrogen, and $X^1$ is $CD_3$, the embodiment where $Y^1$-$Y^{11}$ are all hydrogen, $X^2$ is $CD_3$, $R^1$-$R^8$ are all hydrogen, and $X^1$ is $CH_3$, the embodiment where $Y^1$-$Y^{11}$ are all hydrogen, $X^2$ is $CD_3$, $R^1$-$R^8$ are all hydrogen, and $X^1$ is $CD_3$, the embodiment where $Y^1$-$Y^{11}$ are all hydrogen, $X^2$ is $CD_8$, $R^1$-$R^8$ are all deuterium, and $X^1$ is $CH_3$, or the embodiment where $Y^1$-$Y^{11}$ are all deuterium, $X^2$ is $CD_3$, $R^1$-$R^8$ are all hydrogen, and $X^1$ is $CD_3$.

A preferred embodiment of the present invention is a compound or a pharmaceutically acceptable salt thereof, wherein the compound has any of the following structures:

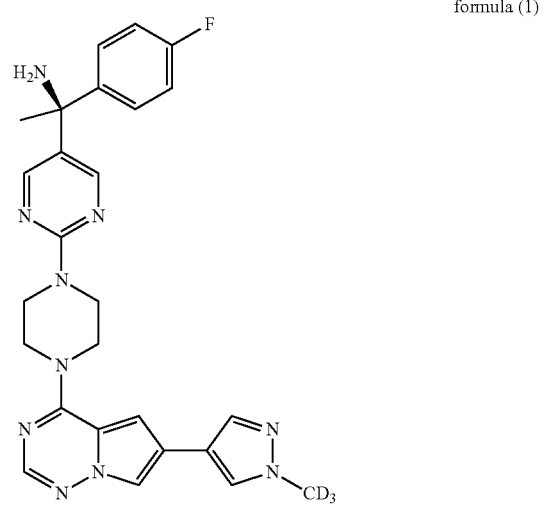

formula (1)

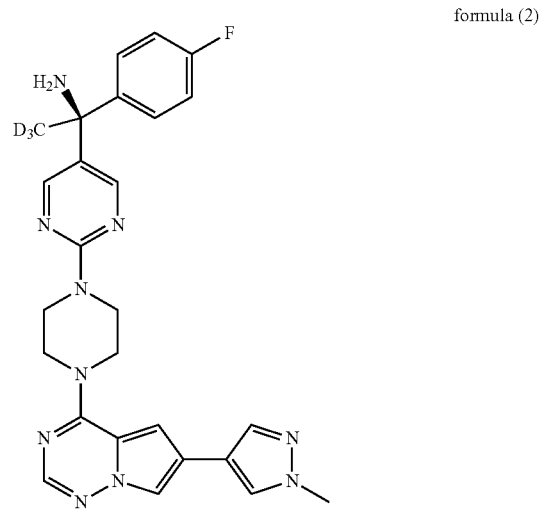

formula (2)

formula (3)
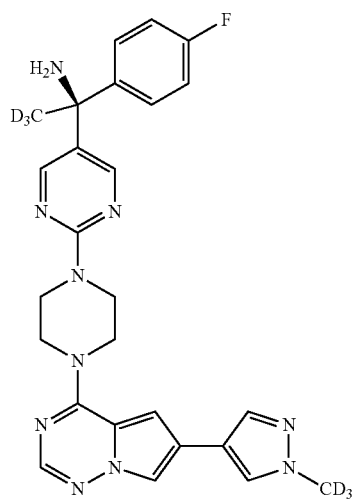
formula (4)
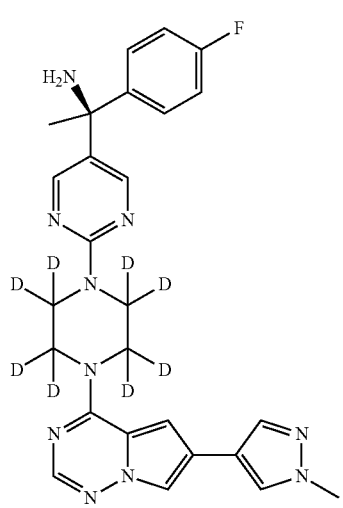
formula (5)
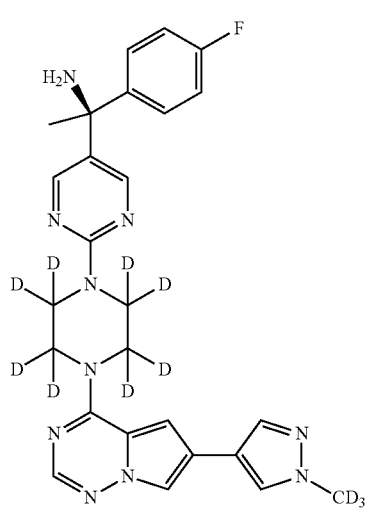
formula (6)
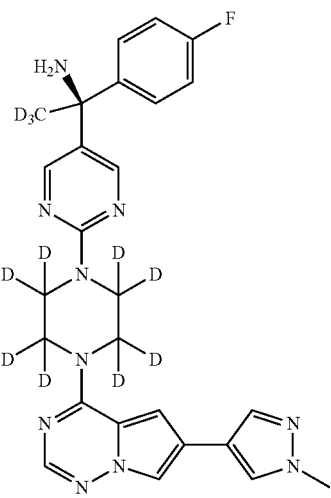
formula (7)
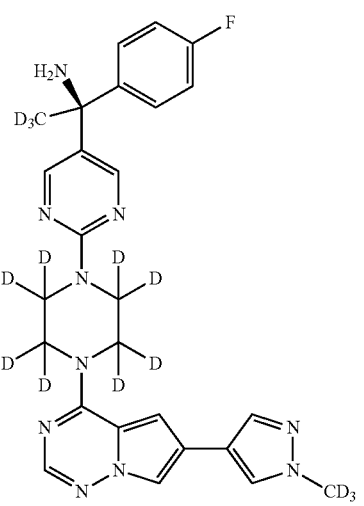
formula (8)
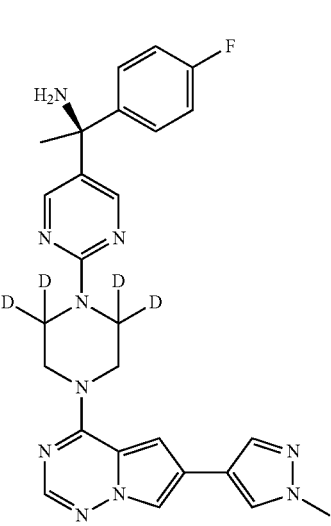

formula (9)
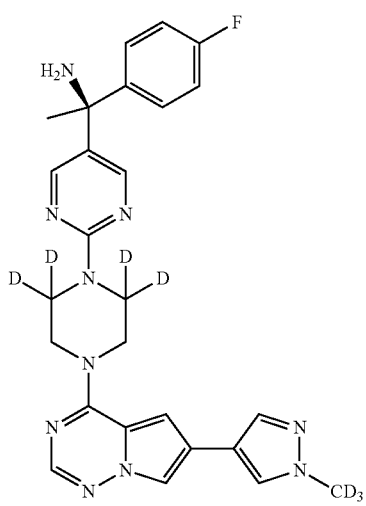
formula (10)
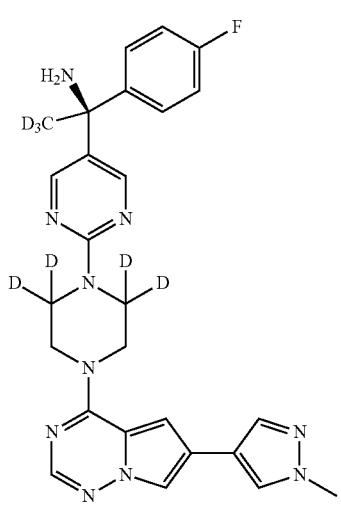
formula (11)
formula (12)
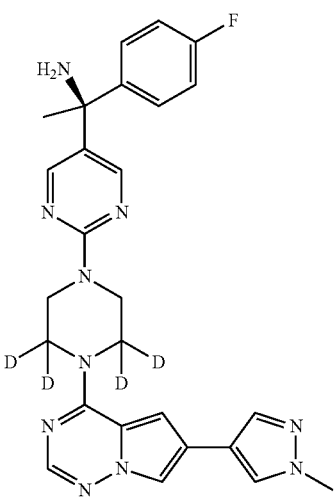
formula (13)
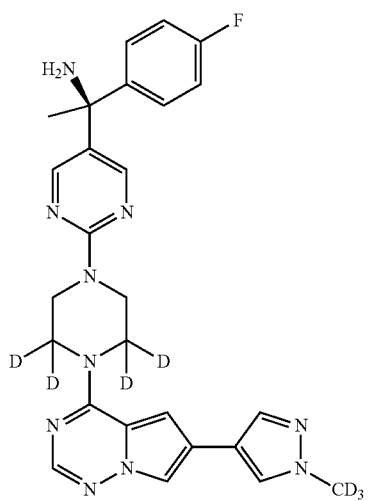
formula (14)
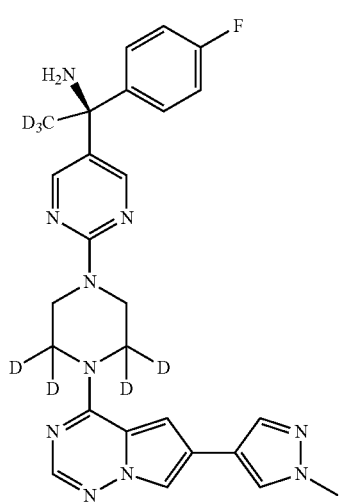

formula (15)
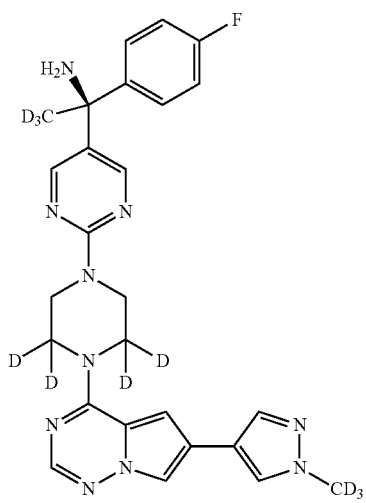
formula (18)
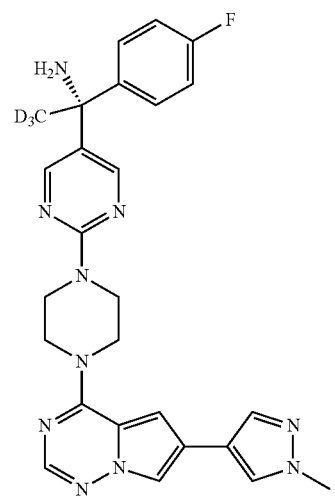
formula (16)
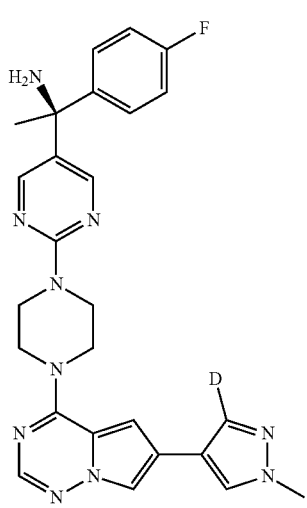
formula (19)
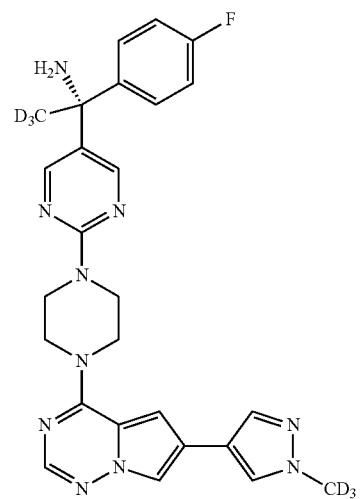
formula (17)
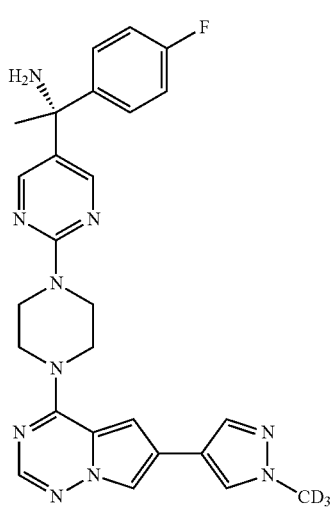
formula (20)
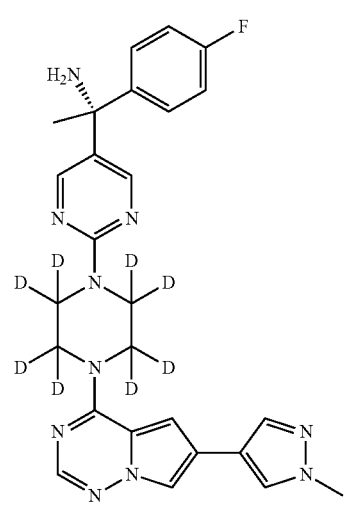

formula (21)
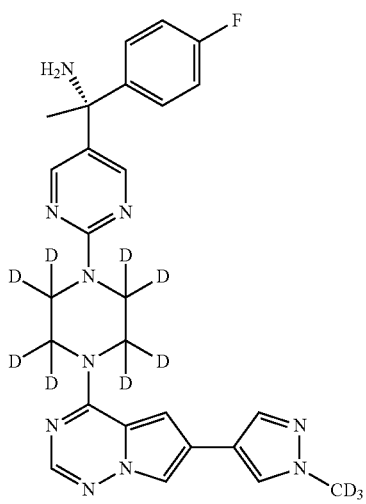
formula (22)
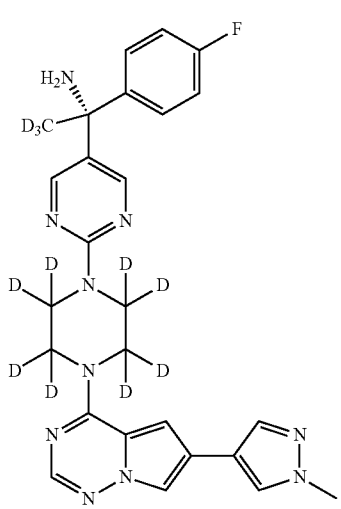
formula (23)
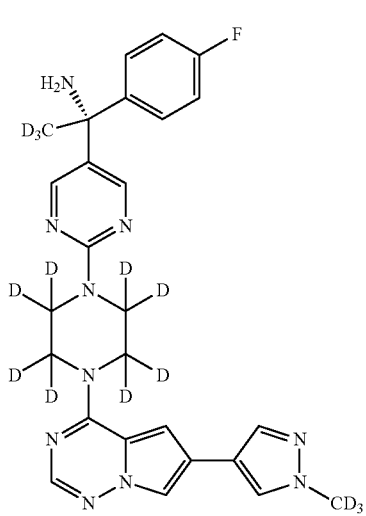
formula (24)
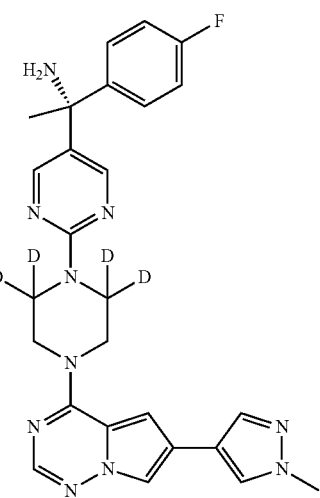
formula (25)
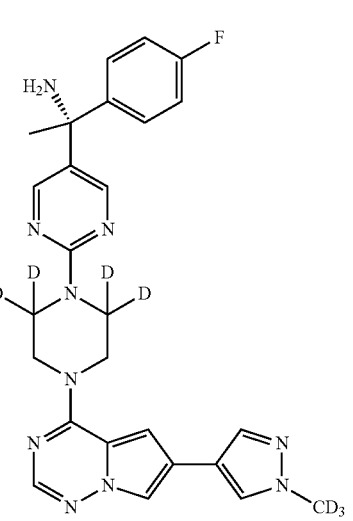
formula (26)
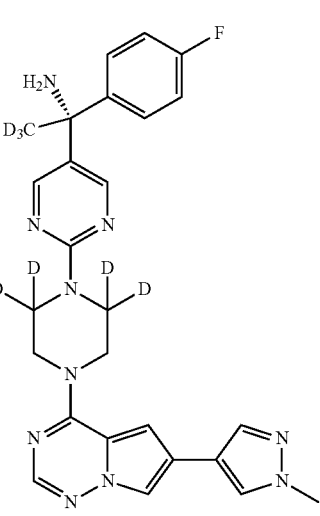

formula (27)
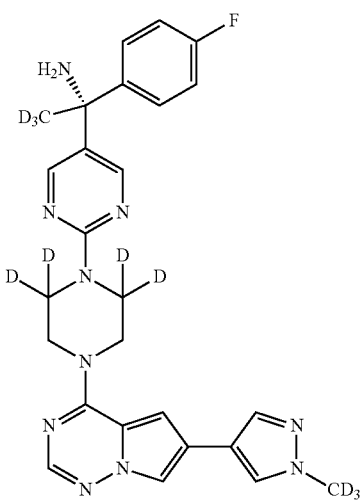
formula (28)
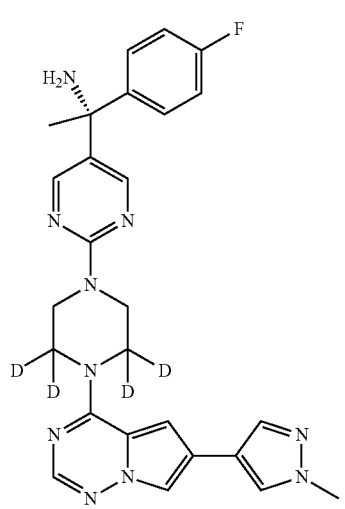
formula (29)
formula (30)
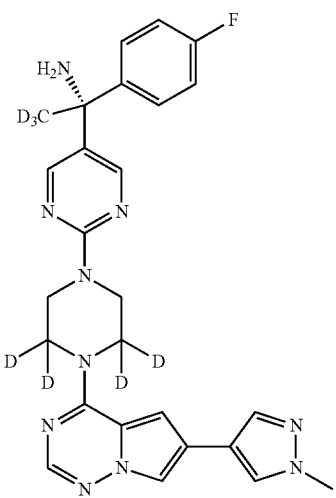
formula (31)
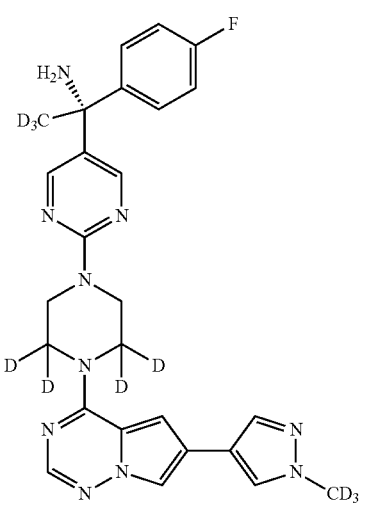
formula (32)
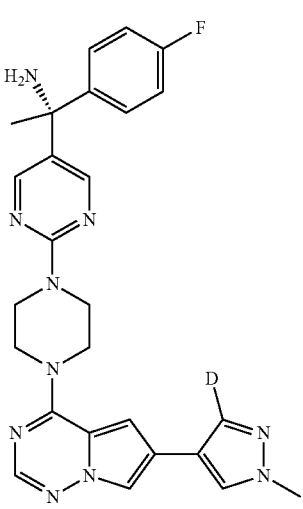

formula (33)
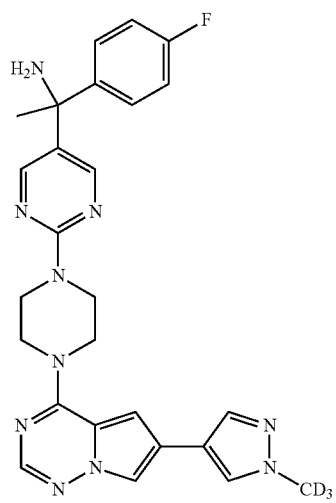
formula (34)
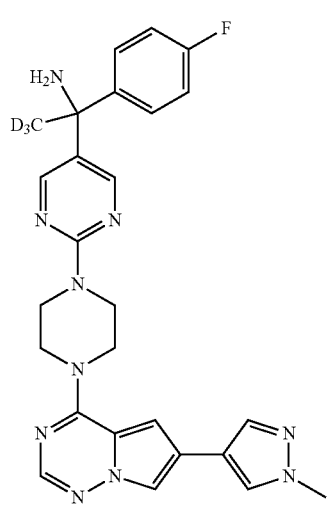
formula (35)
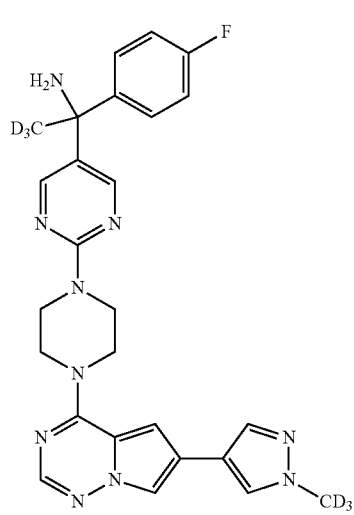
formula (36)
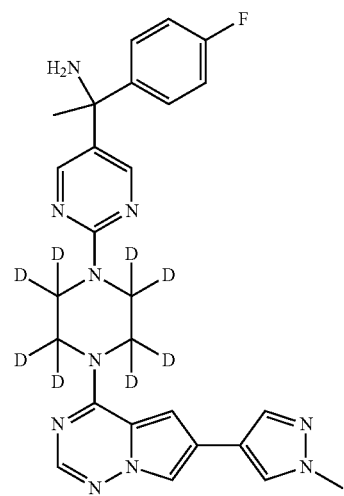
formula (37)
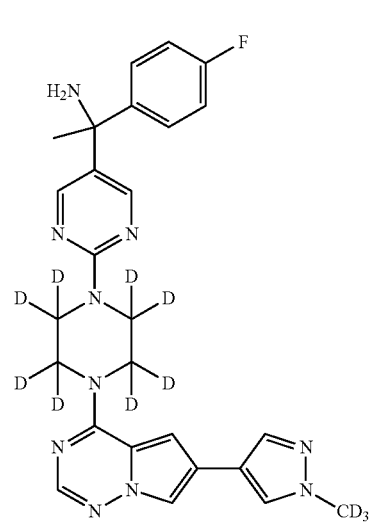
formula (38)
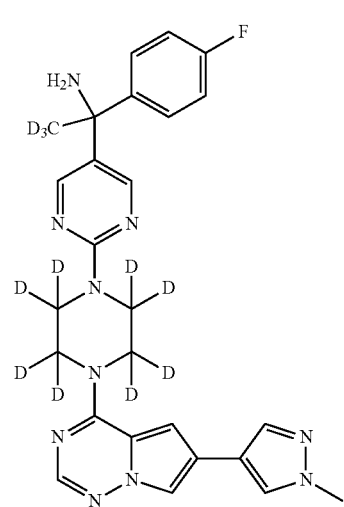

formula (39)
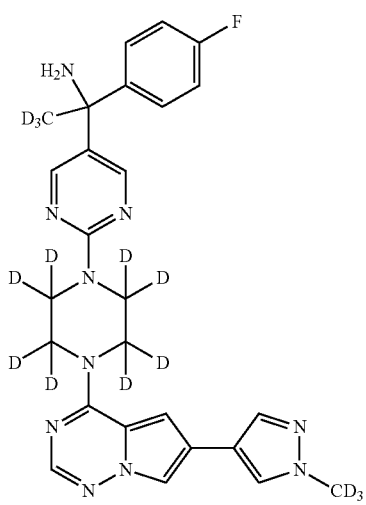
formula (42)
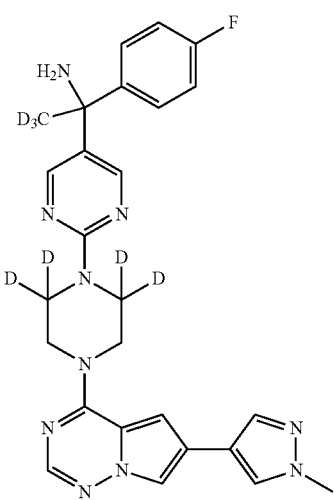
formula (40)
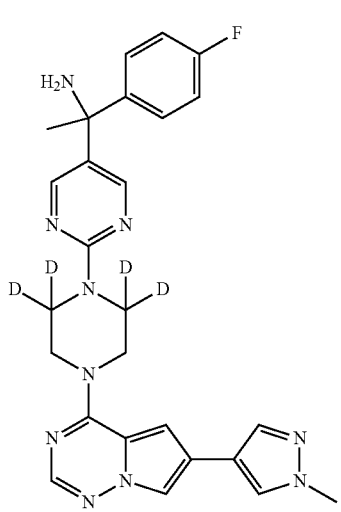
formula (43)
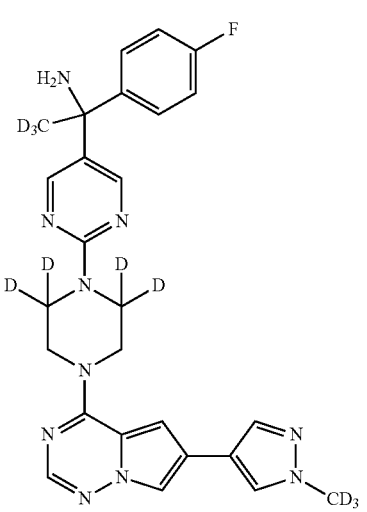
formula (41)
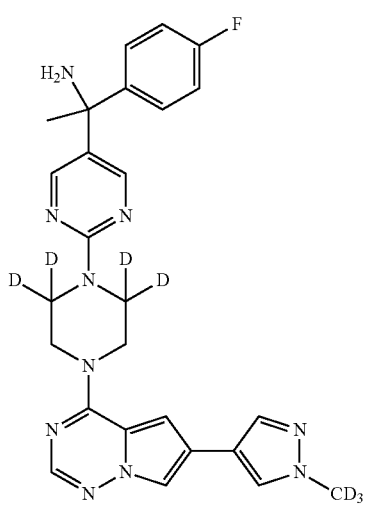
formula (44)
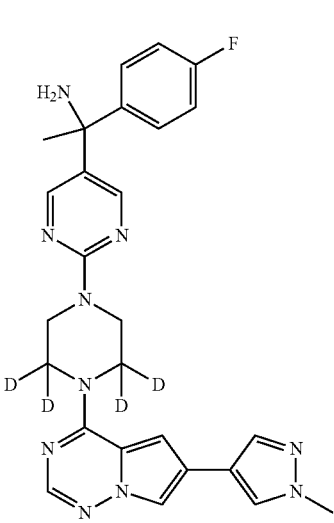

formula (45)

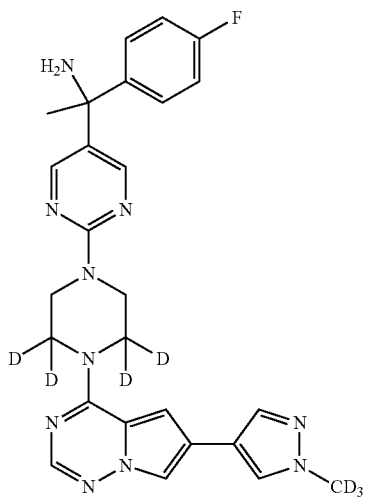

formula (46)

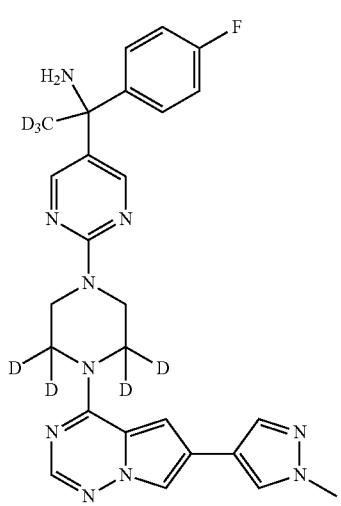

formula (47)

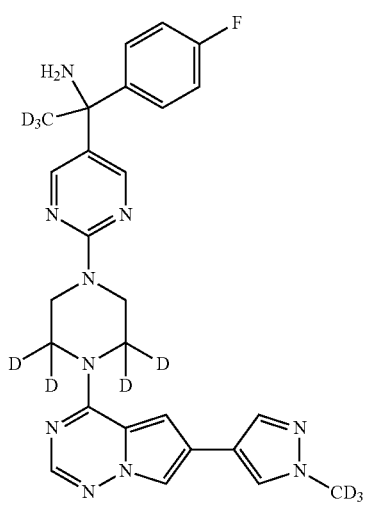

formula (48)

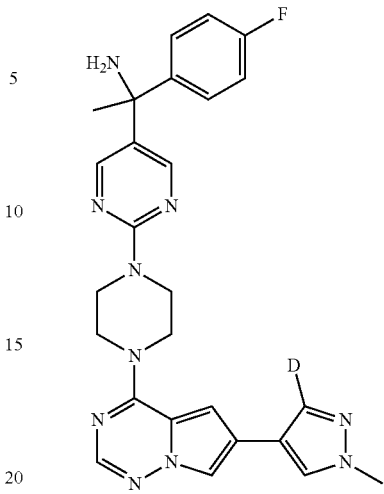

The compounds of the present invention may exist in the form of specific geometric isomers or stereoisomers. The present invention covers all such compounds, including their cis- and trans-isomers, R- and S-enantiomers, (D)-isomers, (L)-isomers, racemates and other mixtures, such as those falling within the scope of the present invention. Additional asymmetric carbon atoms may be present in the substituents (such as an alkyl group). All such isomers and mixtures thereof are intended to be included in the present invention.

For example, if a specific enantiomer of the compound of the present invention is desired, it can be prepared by asymmetric synthesis or derived by the use of chiral auxiliaries, wherein the resulting mixture of diastereomers is separated to dissociate the auxiliary group to provide the pure desired enantiomer. Alternatively, in the case that the molecule contains a basic functional group (such as an amino group) or an acidic functional group (such as a carboxyl group), a diastereomeric salt is formed with an appropriate optically active acid or base, followed by fractional crystallization or chromatography methods well known in the art to resolve the diastereomers thus formed and subsequently recovery of the pure enantiomers.

Unless otherwise specified, when the disclosed compound is named without specifying the stereochemistry or is depicted by the structure with one or more chiral centers, it should be understood to mean all stereoisomers of the compound and its enantiomeric mixtures.

The "enantiomeric excess" or "% enantiomeric excess" of a composition can be calculated using the equation shown below. In the examples shown below, the composition contains 90% of one enantiomer (for example, the S enantiomer) and 10% of the other enantiomer (i.e., the R enantiomer).

$$ee = (90-10)/100 = 80\%.$$

Therefore, a composition containing 90% of one enantiomer and 10% of the other enantiomer is recited to have an enantiomeric excess of 80%.

The compounds or compositions described herein may contain at least 50%, 75%, 90%, 95%, or 99% enantiomeric excess of one form of the compound, for example, the S-enantiomer. In other words, such compounds or compositions contain the S enantiomer in an enantiomeric excess relative to the R enantiomer.

Those skilled in the art will understand that an organic compound can form a complex with a solvent, react in the solvent, or precipitate or crystallize out of the solvent. These complexes are called "solvates". When the solvent is water, the complex is called "hydrate". The present invention covers all solvates of the compounds of the present invention.

The term "solvate" refers to the form of a compound or a salt thereof combined with a solvent, usually formed by a solvolysis reaction. This physical association may include hydrogen bonding. Conventional solvents include water, methanol, ethanol, acetic acid, DMSO, THF, ether and the like. The compounds described herein can be prepared, for example, in crystalline forms, and can be solvated. Suitable solvates include pharmaceutically acceptable solvates and further include stoichiometric solvates and non-stoichiometric solvates. In some cases, the solvate will be able to be separated, for example, when one or more solvent molecules are incorporated into the crystal lattice of a crystalline solid. "Solvate" includes solvates in a solution state and isolatable solvates. Representative solvates include hydrates, ethanolates, and methanolates.

The term "hydrate" refers to a compound that is combined with water. Generally, the ratio of the number of water molecules contained in the hydrate of a compound to the number of molecules of the compound in the hydrate is definite. Therefore, the hydrate of a compound can be represented by, for example, the general formula $R.x\ H_2O$, where R is the compound and x is a number greater than zero. A given compound can form more than one type of hydrate, including, for example, monohydrate (x is 1), lower hydrate (x is a number greater than 0 and less than 1, for example, hemihydrate ($R.0.5H_2O$)) and polyhydrate (x is a number greater than 1, for example, dihydrate ($R.2H_2O$) and hexahydrate ($R.6\ H_2O$)).

The compounds of the invention may be in amorphous or crystalline form (polymorphs). In addition, the compounds of the present invention may exist in one or more crystalline forms. Therefore, the present invention includes all amorphous or crystalline forms of the compounds of the present invention within its scope. The term "polymorph" refers to a crystalline form of a compound (or a salt, hydrate or solvate thereof) in a specific crystal packing arrangement. All polymorphs have the same elemental composition. Different crystalline forms usually have different X-ray diffraction patterns, infrared spectra, melting points, density, hardness, crystal shape, photoelectric properties, stability and solubility. Recrystallization solvent, crystallization rate, storage temperature and other factors can cause one crystalline form to dominate. Various polymorphs of a compound can be prepared by crystallization under different conditions.

The present invention also includes isotopically-labeled compounds, which are equivalent to those described by formula (I), but have one or more atoms replaced by atoms whose atomic mass or mass number is different from the atomic mass or mass number common in nature. Examples of isotopes that can be introduced into the compounds of the present invention include isotopes of hydrogen, carbon, nitrogen, oxygen, phosphorus, sulfur, fluorine, and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. The compounds of the present invention containing the above isotopes and/or other isotopes of other atoms, their prodrugs, and pharmaceutically acceptable salts of the compounds or the prodrugs all fall within the scope of the present invention. Certain isotope-labeled compounds of the present invention, such as those incorporating radioisotopes (such as $^3H$ and $^{14}C$), can be used for drug and/or substrate tissue distribution determination. Tritium, i.e. $^3H$ and carbon-14, i.e. $^{14}C$ isotopes are particularly preferred, because they are easy to prepare and detect. Furthermore, substitution by heavier isotopes, such as deuterium, i.e. $^2H$, may provide therapeutic benefits due to higher metabolic stability, such as prolonged half-life in vivo or reduced dosage requirements, and may therefore be preferable in some cases. Isotope-labeled compounds of formula (I) of the present invention and their prodrugs can generally be prepared by replacing the non-isotope-labeled reagents with readily available isotope-labeled reagents when performing the processes disclosed in the following procedures and/or examples and preparation examples.

In addition, prodrugs are also included in the context of the present invention. The term "prodrug" as used herein refers to a compound that is converted into its active form with medical effects by, for example, hydrolysis in the blood in the body. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each incorporated herein by reference.

A prodrug is any covalently bonded compound of the invention. When such a prodrug is administered to a patient, it releases the parent compound in the body. Prodrugs are usually prepared by modifying functional groups, and the modification is performed in such a way that the parent compound can be produced by conventional operations or cleavage in vivo. Prodrugs include, for example, the compounds of the present invention in which a hydroxyl, amino, or sulfhydryl group is bonded to any group, which can be cleaved to form the hydroxyl, amino, or sulfhydryl group when administered to a patient. Therefore, representative examples of prodrugs include, but are not limited to, acetate/acetamide, formate/formamide, and benzoate/benzamide derivatives of the hydroxyl, sulfhydryl, and amino functional groups of the compounds of formula (I). In addition, in the case of carboxylic acid (—COOH), esters such as methyl esters, ethyl esters and the like can be used. The ester itself can be active and/or can be hydrolyzed in vivo. Suitable pharmaceutically acceptable ester groups hydrolyzable in vivo include those groups that are easily decomposed in the human body to release the parent acid or salt thereof.

Synthesis

The compounds of the present invention (including their salts and N-oxides) can be prepared using known organic synthesis techniques, and can be synthesized according to any of a variety of possible synthetic routes, such as those in the schemes below. The reaction for preparing the compound of the present invention can be carried out in a suitable solvent, and those skilled in the art of organic synthesis can easily select the solvent. A suitable solvent may be substantially non-reactive with the starting material (reactant), intermediate or product at the temperature at which the reaction proceeds (for example, a temperature in the range from the freezing temperature of the solvent to the boiling point of the solvent). The intended reaction can be carried out in one solvent or a mixture of more than one solvent. The skilled person can select the solvent used in a specific reaction step according to the specific reaction step.

The preparation of the compounds of the present invention may involve the protection and deprotection of different chemical groups. Those skilled in the art can easily determine whether protection and deprotection are required and select an appropriate protecting group. For the chemical properties of the protecting groups, see, for example, Wuts and Greene, Protective Groups in Organic Synthesis, 4th edition, John Wiley & Sons: New Jersey, (2006), which is incorporated herein by reference in its entirety.

The reaction can be monitored according to any suitable method known in the art. For example, spectroscopic means (such as nuclear magnetic resonance (NMR) spectroscopy (for example, $^1$H or $^{13}$C), infrared (IR) spectroscopy, spectrophotometry (for example, UV-vis), mass spectrometry (MS)) or chromatographic methods such as high performance liquid chromatography (HPLC) or thin layer chromatography (TLC) can be used to monitor product formation.

Pharmaceutical Compositions, Preparations and Kits

In another aspect, the invention provides a pharmaceutical composition comprising a compound of the invention (also referred to as an "active ingredient") and a pharmaceutically acceptable excipient. In some embodiments, the pharmaceutical composition comprises an effective amount of active ingredient. In some embodiments, the pharmaceutical composition comprises a therapeutically effective amount of the active ingredient. In some embodiments, the pharmaceutical composition comprises a prophylactically effective amount of the active ingredient.

The pharmaceutically acceptable excipient used in the present invention refers to a non-toxic carrier, adjuvant or vehicle that does not damage the pharmacological activity of the compound formulated together. Pharmaceutically acceptable carriers, adjuvants or vehicles that can be used in the composition of the present invention include, but are not limited to, ion exchangers, alumina, aluminum stearate, lecithin, serum proteins (such as human serum albumin), buffer substances (such as phosphate), glycine, sorbic acid, potassium sorbate, partial glyceride mixtures of saturated plant fatty acids, water, salts or electrolytes (such as protamine sulfate), disodium hydrogen phosphate, potassium hydrogen phosphate, sodium chloride, zinc salt, silica gel, magnesium trisilicate, polyvinylpyrrolidone, cellulose-based substances, polyethylene glycol, sodium carboxymethyl cellulose, polyacrylate, wax, polyethylene-polyoxypropylene block polymers, polyethylene glycol and lanolin.

The present invention also includes kits (e.g., pharmaceutical packaging). The kit provided may include the compound of the present invention, other therapeutic agents, and the first and second containers (for example, vials, ampoules, bottles, syringes, and/or dispersible packaging or other suitable containers) containing the compound of the present invention and the other therapeutic agents. In some embodiments, the kit provided may also optionally include a third container, which contains pharmaceutical excipients for diluting or suspending the compound of the present invention and/or other therapeutic agents. In some embodiments, the compound of the present invention and the other therapeutic agent provided in the first container and the second container are combined to form a unit dosage form.

The pharmaceutical composition provided by the present invention can be administered by many routes, including but not limited to: oral administration, parenteral administration, inhalation administration, topical administration, rectal administration, nasal administration, buccal administration, vaginal administration, administration via implants or other modes of administration. For example, parenteral administration as used herein includes subcutaneous administration, intradermal administration, intravenous administration, intramuscular administration, intraarticular administration, intraarterial administration, intrasynovial administration, intrasternal administration, intracerebrospinal administration, intralesional administration, and intracranial injection or infusion technology.

Generally, an effective amount of a compound provided herein is administered. According to relevant circumstances, including the condition being treated, the route of administration selected, the compound actually administered, the age, weight and response of the individual patient, the severity of the patient's symptoms, etc., the amount of the compound actually administered can be determined by a doctor.

When used to prevent the condition of the present invention, the compound provided herein is administered to a subject at risk of developing the condition, typically based on the doctor's advice and under the supervision of the doctor, at the dosage level as described above. Subjects at risk of developing a specific condition generally include subjects with a family history of the condition, or those subjects who are particularly sensitive to the formation of the condition as determined by genetic testing or screening.

The pharmaceutical compositions provided herein can also be administered chronically ("long-term administration"). Long-term administration refers to the administration of the compound or its pharmaceutical composition over a long period of time, for example, 3 months, 6 months, 1 year, 2 years, 3 years, 5 years, etc., or the administration can be continued indefinitely, for example, for the rest of the subject's life. In some embodiments, long-term administration is intended to provide a constant level of the compound, for example, within a therapeutic window, in the blood over a long period of time.

Various administration methods can be used to further deliver the pharmaceutical composition of the present invention. For example, in some embodiments, the pharmaceutical composition may be administered by bolus injection, for example, in order to rapidly increase the concentration of the compound in the blood to an effective level. The bolus dose depends on the target systemic level of the active ingredient. For example, an intramuscular or subcutaneous bolus dose releases the active ingredient slowly, while a bolus injection delivered directly into a vein (for example, by IV infusion) allows a more rapid delivery to rapidly increase the concentration of the active ingredient in the blood to an effective level. In other embodiments, the pharmaceutical composition may be administered in the form of a continuous infusion, for example, by IV infusion, so as to provide a steady concentration of the active ingredient in the subject's body. Furthermore, in other embodiments, a bolus dose of the pharmaceutical composition may be administered first, followed by continuous infusion.

Oral compositions can take the form of bulk liquid solutions or suspensions or bulk powders. However, more generally, in order to facilitate precise dosing, the composition is provided in unit dosage forms. The term "unit dosage form" refers to a physically discrete unit suitable as a unit dose for human patients and other mammals, each unit containing a predetermined amount of active substance suitable for producing the desired therapeutic effect and suitable pharmaceutical excipients. Typical unit dosage forms include pre-filled, pre-measured ampoules or syringes of liquid compositions, or pills, tablets, capsules, etc. in the case of solid compositions. In this composition, the compound is usually a minor component (in about 0.1 to about 50% by weight, or preferably about 1 to about 40% by weight), and the remainder is various carriers or excipients and processing aids useful for forming the desired administration form.

For oral doses, the representative regimen is one to five oral doses per day, especially two to four oral doses, typically three oral doses. Using these dosing modes, each dose provides about 0.01 to about 20 mg/kg of the compound of the present invention, with preferred doses each providing about 0.1 to about 10 mg/kg, especially about 1 to about 5 mg/kg.

In order to provide a blood level similar to or lower than the injected dose, the transdermal dose is usually selected in an amount of about 0.01 to about 20% by weight, preferably about 0.1 to about 20% by weight, and preferably about 0.1 to about 10% by weight, and more preferably about 0.5 to about 15% by weight.

From about 1 to about 120 hours, especially 24 to 96 hours, the injection dose level is in the range of about 0.1 mg/kg/hour to at least 10 mg/kg/hour. In order to obtain a sufficient steady level, a preload bolus of about 0.1 mg/kg to about 10 mg/kg or more can also be administered. For human patients of 40 to 80 kg, the maximum total dose cannot exceed approximately 2 g/day.

Liquid forms suitable for oral administration may include suitable aqueous or non-aqueous carriers as well as buffers, suspending and dispersing agents, coloring agents, flavoring agents, and the like. The solid form may include, for example, any of the following components, or compounds with similar properties: binders, for example, microcrystalline cellulose, tragacanth, or gelatin; excipients, for example, starch or lactose, disintegrants, for example, alginic acid, Primogel or corn starch; lubricants, for example, magnesium stearate; glidants, for example, colloidal silicon dioxide; sweeteners, for example, sucrose or saccharin; or flavoring agents, for example, mint, methyl salicylate or orange flavoring agent.

Injectable compositions are typically based on injectable sterile saline or phosphate buffered saline, or other injectable excipients known in the art. As mentioned earlier, in such compositions, the active compound is typically a minor component, often of about 0.05 to 10% by weight, with the remainder being injectable excipients and the like.

The transdermal composition is typically formulated as a topical ointment or cream containing the active ingredients. When formulated as an ointment, the active ingredient is typically combined with paraffin or a water-miscible ointment base. Alternatively, the active ingredient can be formulated as a cream with, for example, an oil-in-water cream base. Such transdermal formulations are well known in the art, and generally include other components for enhancing stable skin penetration of the active ingredient or the formulation. All such known transdermal formulations and components are included within the scope provided by the present invention.

The compounds of the present invention can also be administered via transdermal devices. Therefore, transdermal administration can be achieved using a reservoir or porous membrane type, or a variety of solid matrix patches.

The above-mentioned components of the composition for oral administration, injection or topical administration are only representative. Other materials and processing technologies are described in Part 8 in Remington's Pharmaceutical Sciences, 17th edition, 1985, Mack Publishing Company, Easton, Pa., which is incorporated herein by reference.

The compounds of the present invention can also be administered in a sustained release form or from a sustained release drug delivery system. A description of representative sustained-release materials can be found in Remington's Pharmaceutical Sciences.

The invention also relates to pharmaceutically acceptable formulations of the compounds of the invention. In one embodiment, the formulation contains water. In another embodiment, the formulation comprises a cyclodextrin derivative. The most common cyclodextrins are α-, β- and γ-cyclodextrins composed of 6, 7 and 8 α-1,4-linked glucose units, respectively, which optionally include one or more substituents on the linked sugar moieties, including but not limited to: methylated, hydroxyalkylated, acylated, and sulfoalkyl ether substituted. In some embodiments, the cyclodextrin is a sulfoalkyl ether β-cyclodextrin, for example, sulfobutyl ether β-cyclodextrin, also known as Captisol. See, for example, U.S. Pat. No. 5,376,645. In some embodiments, the formulation comprises hexapropyl-A-cyclodextrin (e.g., 10-50% in water).

Indications

The compounds of the invention can be used to treat human or non-human conditions associated with abnormal KIT activity. Activation mutations in KIT are present in a variety of indications, including systemic mastocytosis, gastrointestinal stromal tumors, acute myeloid leukemia, melanoma, seminoma, intracranial germ cell tumors, and mediastinum B-cell lymphoma.

Mastocytosis refers to a group of conditions characterized by excessive accumulation of mast cells in one or more tissues. Mastocytosis is divided into two groups of conditions: (1) cutaneous mastocytosis (CM), which describes a form limited to the skin; and (2) systemic mastocytosis (SM), which describes a form in which mast cells infiltrate organs other than dermis, with or without skin involvement. SM is further divided into five forms: indolent SM (ISM), smoldering SM (SSM), aggressive SM (ASM), SM with associated hematological non-mast cell lineage disorder (SM-AHNMD), and mast cell leukemia (MCL).

The diagnosis of systemic mastocytosis is partly based on histological and cytological studies of bone marrow, which show that mast cells often have atypical morphology during infiltration and express non-mast cell markers (CD25 and/or CD2). SM is diagnosed when bone marrow mast cell infiltration occurs in one of the following conditions: (1) abnormal mast cell morphology (spindle cells); (2) plasmin level increased to above 20 ng/mL; or (3) presence of activation KIT D816V mutation.

The activation mutations at D816 were found in many cases of mastocytosis (90-98%), among which the most common mutations were D816V and D86H, and D816Y. The D816V mutation is present in the activation loop in the kinase domain and causes the constitutive activation of KIT kinase.

The compounds of the invention can also be used to treat gastrointestinal stromal tumors (GIST). Complete surgical resection is still the primary treatment of choice for patients with primary GIST. Surgery is effective in about 50% of GIST patients; and in the remaining patients, tumor recurrence often occurs. It has also been demonstrated that initial treatment with KIT inhibitors such as imatinib is sufficient for initial treatment. However, resistance to imatinib appears within a few months due to somatic mutations. These second-generation imatinib resistance mutations are most often located in exon 11, 13, 14, 17, or 18. Sunitinib is the standard of care for second-line treatment of most imatinib-resistant tumors and is effective for those with mutations in exons 11, 13, and 14. However, the second-generation KIT mutations in exons 17 and 18 are resistant to sunitinib treatment and, in addition, tumors with the third-generation resistance mutations in exons 17 and 18 appear after several months of sunitinib treatment. Regorafenib has shown promising results in the phase 3 clinical trials of imatinib and sunitinib-resistant GIST. It has activity on some but not all exon 17 and 18 mutations (D816 is one of them). Therefore, there is a need for therapeutics for GIST patients with specific exon 17 mutations that regorafenib cannot resolve.

In the context of refractory GIST, in addition to using the compounds described herein as a single agent, the use of imatinib, sunitinib and/or regorafenib in combination with the compounds disclosed herein can prevent the occurrence of exon-17 mutation resistance.

There is a subset of GIST patients with the D842V mutation in PDGFRα: GIST patients in this subgroup can be classified by identifying the mutation. All currently available tyrosine kinase inhibitors are difficult to treat this subset of patients. The compounds described herein can be used to treat these patients due to their activity against PDGFRα D842V.

The compounds described herein can also be used to treat acute myeloid leukemia (AML). AML patients also have potentially KIT mutations, and most of these mutations are in the D816 position.

In addition, KIT mutations are associated with Ewing's sarcoma, DLBCL (diffuse large B-cell lymphoma), dysgerminoma, myelodysplastic syndrome, nasal NKIT-cell lymphoma, chronic myelomonocytic leukemia and brain cancer.

The compounds of the present invention have activity on one or more KIT mutations in exon 17 (e.g., D816V, D816Y, D816F, D816K, D816A, D816G, D820A, D820E, D820G, N822K, N822H, Y823D, and A829P), but much less activity on wild-type KIT. These compounds can be administered in combination with the following agents: a) those active on other KIT activation mutations such as exon 9 and 11 mutations, but b) inactive on exon 17 mutations. Such agents include imatinib, sunitinib and regorafenib. The combination of the compound and the agent will therefore inhibit the exon 17 mutation KIT as well as the exon 19/11 mutation KIT. The compound and agent can be administered simultaneously or in an alternating regimen. That is, the exon 17 mutation KIT inhibitor can be administered alone for a period of time; and then the exon 9/11 mutation KIT inhibitor can be administered alone for a period of time. This cycle can then be repeated. It is believed that such regimen can slow down the development of resistance to exon 17 mutation KIT inhibitors and/or exon 9/11 mutation KIT inhibitors.

In addition, the compounds of the present invention that can be selected for exon 17 mutations can be administered in combination with an agent active on exon 9/11 mutations and a third agent contemplated for mutations omitted in the case of a two-way combination. The combination of the three agents can inhibit a series of KIT mutations, and in some cases can inhibit wild-type KIT. The agents can be administered simultaneously or in an alternating regimen. They can be administered individually each time, or two agents can be administered together for a period of time; and then a third agent can be administered separately for a period of time. It is believed that such regimen can slow down the development of resistance to mutant KIT inhibitors.

EXAMPLE

The present invention will be further illustrated below in conjunction with specific examples. It should be understood that these examples are only used to illustrate the present invention and not to limit the scope of the present invention. The experimental methods that do not indicate specific conditions in the following examples usually follow the conventional conditions or the conditions suggested by the manufacturer. Unless otherwise specified, parts and percentages are parts by weight and percentages by weight.

Generally, in the preparation scheme, each reaction is usually carried out in an inert solvent at room temperature to reflux temperature (such as 0° C. to 100° C., preferably 0° C. to 80° C.). The reaction duration is usually 0.1-60 hours, preferably 0.5-24 hours.

The abbreviations used herein have the following meanings:

| APCI | atmosphere pressure chemical ionization |
| --- | --- |
| DIPEA | N,N-diisopropylethylamine |
| THF | tetrahydrofuran |
| NaOH | sodium hydroxide |
| HCl | hydrochloric acid |
| HOBT | 1-hydroxybenzotriazole |
| EDCI | 1-(3-dimethylaminopropyl)-3-ethyl carbodiimide hydrochloride |
| TFA | trifluoroacetic acid |
| Boc$_2$O | di-tert-butyl dicarbonate |
| NaH | sodium hydride |
| Pd(dppf)Cl$_2$ | [1,1'-bis(diphenylphosphino)ferrocene] palladium dichloride |
| DCM | dichloromethane |
| MTBE | methyl tert-butyl ether |

Example 1

Preparation of (4-fluorophenyl)(2-(piperazin-1-yl)pyrimidin-5-yl)methanone (Intermediate A-1)

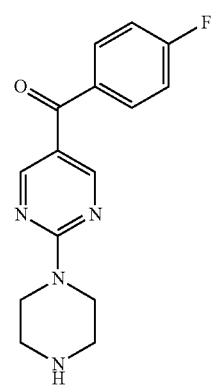

A-1

The following scheme was used for synthesis:

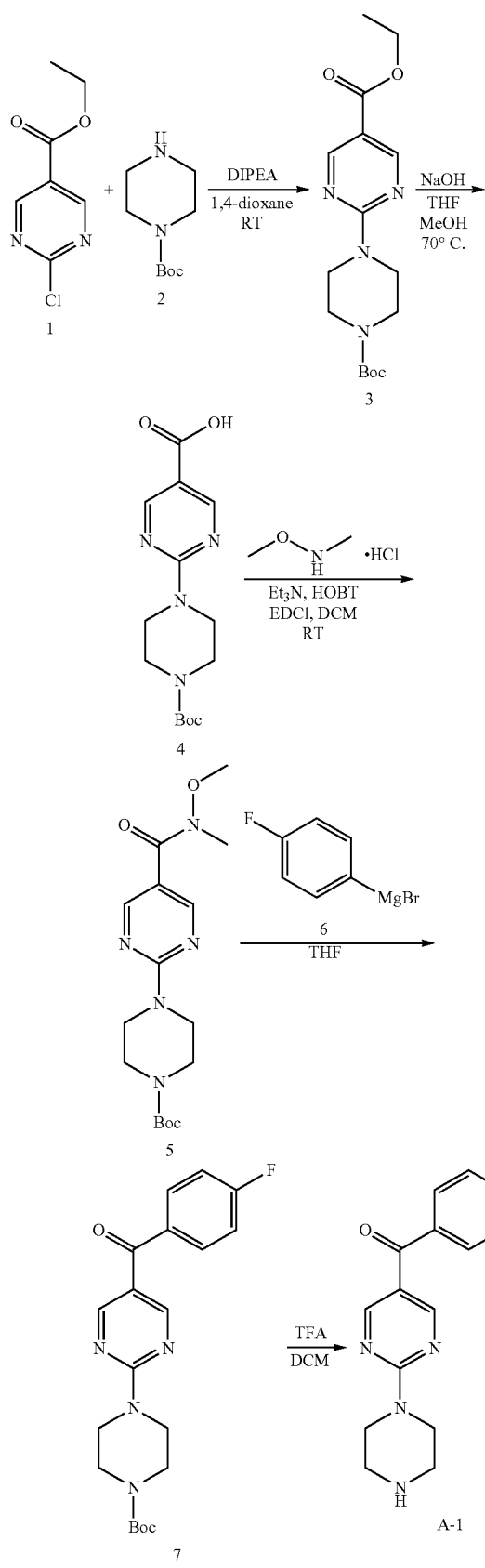

Step 1. Synthesis of Compound 3

1,4-dioxane (100 mL) and compound 1 (10.0 g, 53.59 mmol) were added to a 250 mL single-neck flask equipped with a magnetic stirrer, stirred to dissolve to clear, cooled in an ice-water bath, and then added with compound 2 (9.98 g, 53.59 mmol) and DIPEA (20.8 mL, 134 mmol). With the ice bath removed, the reaction was stirred at room temperature under a nitrogen atmosphere for 3 hours. The solvent was evaporated under reduced pressure. Silica gel column purification provided 18.0 g of white solid with a yield of 99.85%. LC-MS(APCI): m/z=337.2 (M+1)$^+$.

Step 2. Synthesis of Compound 4

THF (100 mL), methanol (100 mL) and compound 3 (17.0 g, 50.54 mmol) were added to a 500 mL single-neck flask equipped with a magnetic stirrer and condenser tube, stirred to dissolve to clear and added with aqueous NaOH solution (4.04 g, 0.11 mol, 100 mL) with stirring, warmed to 70° C. under a nitrogen atmosphere, stirred for reaction for 2 hours with the temperature kept, and cooled to room temperature, pH adjusted to ~5 with 1M HCl (aq.). A large amount of white solid precipitated, which was filtered, washed with water (10 mL), and dried under vacuum to obtain 15.0 g of white solid with a yield of 96.26%. LC-MS(APCI): m/z=309.2 (M+1)$^+$.

Step 3. Synthesis of Compound 5

Compound 4 (6.90 g, 22.38 mmol) and dry dichloromethane (100 mL) were added to a 250 mL single-neck flask equipped with a magnetic stirrer, stirred to dissolve to clear, and added with HOBT (3.63 g, 26.85 mmol), EDCI (6.43 g, 33.57 mmol) and triethylamine (9.06 g, 89.51 mmol). The mixture was stirred under nitrogen atmosphere at room temperature for 1 hour. N,O-dimethylhydroxylamine hydrochloride (2.62 g, 26.85 mmol) was added. After the addition, the reaction was stirred under nitrogen atmosphere for another 3 hours. Water (50 mL) was added to quench the reaction. The organic layer was separated, dried over anhydrous sodium sulfate, filtered, concentrated and subjected to a silica gel column to obtain 3.0 g of white solid with a yield of 38.15%. LC-MS(APCI): m/z=352.2 (M+1)$^+$. $^1$H NMR (400 MHz, CDCl$_3$) δ 8.82 (s, 2H), 3.90 (t, J=5.2 Hz, 4H), 3.62 (s, 3H), 3.51 (t, J=5.2 Hz, 4H), 3.36 (s, 3H), 1.49 (s, 9H).

Step 4. Synthesis of Compound 7

Compound 5 (3.0 g, 8.54 mmol) and anhydrous THF (30 mL) were added to a 100 mL two-neck flask equipped with a magnetic stirrer, stirred to dissolve to clear, vacuumed and protected by nitrogen, cooled in an ice-water bath, and added dropwise with a solution of compound 6 in THF (2M, 8.54 mL, 17.07 mmol). After the addition, with the ice bath removed, the reaction was stirred at room temperature for 3 hours. The reaction was quenched by adding dilute hydrochloric acid (1M, 15 mL), extracted with ethyl acetate (30 mL×2), washed with water (20 mL), saturated brine (20 mL), dried over anhydrous sodium sulfate, filtered, concentrated under reduced pressure and evaporated to remove the solvent. The residue was subjected to a silica gel column to obtain 2.37 g of off-white solid with a yield of 71.8%. LC-MS(APCI): m/z=387.1 (M+1)$^+$. $^1$H NMR (300 MHz, CDCl₃) δ 8.77 (s, 2H), 7.82-7.77 (m, 2H), 7.21-7.16 (m, 2H), 3.98-3.95 (m, 4H), 3.56-3.52 (m, 4H), 1.50 (s, 9H).

Step 5. Synthesis of Intermediate Compound A-1

Compound 7 (2.37 g, 6.13 mmol) and dichloromethane (25 mL) were added to a 100 mL single-neck flask equipped with a magnetic stirrer, stirred to dissolve to clear, and added with TFA (5 mL). The reaction was stirred at room temperature under nitrogen atmosphere for 2 hours. The solvent was evaporated under reduced pressure. The residue was added with saturated aqueous sodium bicarbonate (10 mL), and extracted with dichloromethane (20 mL×3). The organic phases were combined, dried over anhydrous sodium sulfate, filtered, and concentrated to dryness to obtain 1.50 g of so yellow solid with a yield of 85.42%. LC-MS(APCI): m/z=287.1 (M+1)⁺.

Example 2

Preparation of (4-fluorophenyl)(2-(piperazin-1-yl-2,2,3,3,5,5,6,6-d₈)pyrimidin-5-yl)methanone (Intermediate A-2)

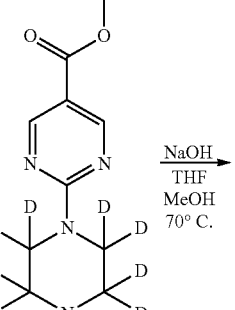

A-2

The following scheme was used for synthesis:

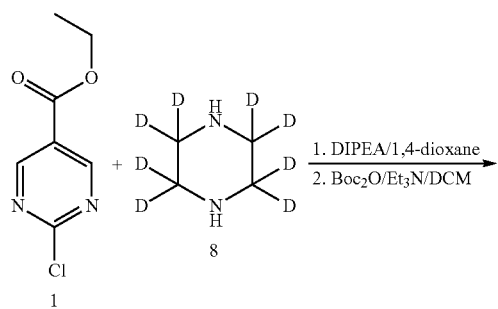

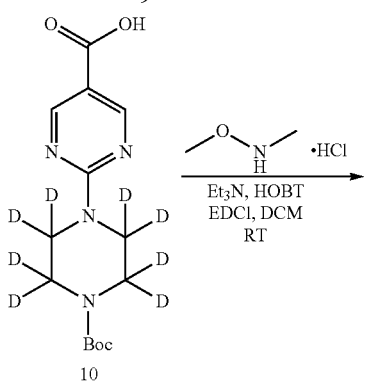

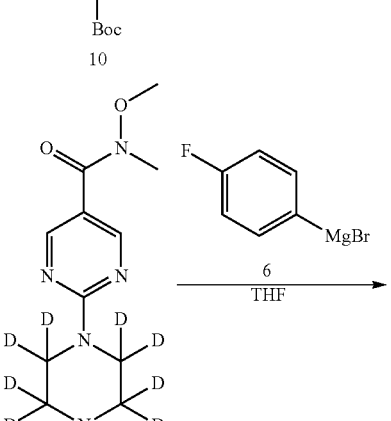

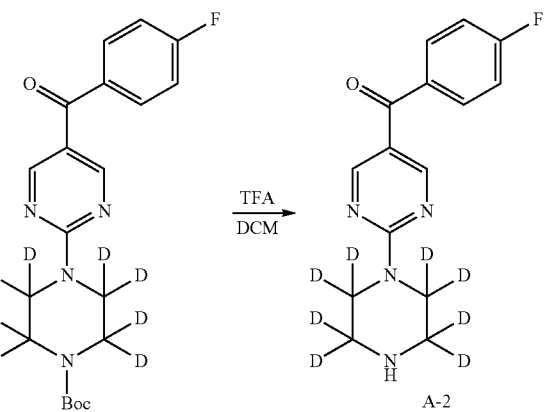

Step 1. Synthesis of Compound 9

1,4-dioxane (60 mL) and compound 1 (4.0 g, 21.4 mmol) were added to a 100 mL single-neck flask equipped with a magnetic stirrer, stirred to dissolve to clear, cooled in an ice-water bath, and then added with compound 8 (2.48 g, 25.6 mmol) and DIPEA (7.5 g, 53.6 mmol). With the ice bath removed, the reaction was stirred at room temperature under nitrogen atmosphere for 3 hours. Boc$_2$O (9.3 g, 40.3 mmol) was added, and the reaction was stirred for another 1 hour. The solvent was evaporated under reduced pressure. The residue was subjected to a silica gel column to obtain 3.5 g of white solid with a yield of 47.4%. LC-MS(APCI): m/z=345.2 (M+1)$^+$.

Step 2. Synthesis of Compound 10

THF (30 mL), methanol (30 mL) and compound 9 (3.5 g, 10.17 mmol) were added to a 100 mL single-neck flask equipped with a magnetic stirrer and condenser tube, stirred to dissolve to clear, added with an aqueous NaOH solution (0.83 g, 20.34 mmol, dissolved in 30 mL water) with stirring, warmed to 70° C. under nitrogen atmosphere, stirred for reaction for 2 hours with the temperature kept, and cooled to room temperature, pH adjusted to ~5 with 1M HCl (aq.). A large amount of white solid precipitated, which was filtered, washed with water (10 mL), and dried under vacuum to obtain 3.0 g of white solid, with a yield of 93.05%. LC-MS(APCI): m/z=317.2 (M+1)$^+$.

Step 3. Synthesis of Compound 11

Compound 10 (3.0 g, 9.48 mmol) and dry dichloromethane (30 mL) were added to a 100 mL single-neck flask equipped with a magnetic stirrer, stirred to dissolve to clear, added with HOBT (1.54 g, 11.38 mmol), EDCI (2.73 g, 14.22 mmol) and triethylamine (3.84 g, 37.93 mmol). The mixture was stirred under nitrogen atmosphere at room temperature for 1 hour. N,O-dimethylhydroxylamine hydrochloride (1.11 g, 11.38 mmol) was added. After the addition, the reaction was stirred under nitrogen atmosphere for another 3 hours. Water (30 mL) was added to quench the reaction. The organic layer was separated, dried over anhydrous sodium sulfate, filtered, concentrated and subjected to a silica gel column to obtain 3.0 g of white solid with a yield of 88.02%. LC-MS(APCI): m/z=360.2 (M+1)$^+$. $^1$H NMR (400 MHz, CDCl$_3$) δ 8.82 (s, 2H), 3.62 (s, 3H), 3.36 (s, 3H), 1.49 (s, 9H).

Step 4. Synthesis of Compound 12

Compound 11 (3.0 g, 8.35 mmol) and anhydrous THF (30 mL) were added to a 100 mL two-neck flask equipped with a magnetic stirrer, stirred to dissolve to clear, vacuumed and protected by nitrogen, cooled in an ice-water bath, and added dropwise with a solution of compound 6 in THF (2M, 8.35 mL, 16.69 mmol). After the addition, with the ice bath removed, the reaction was stirred at room temperature for 3 hours. The reaction was quenched by adding dilute hydrochloric acid (1M, 15 mL), extracted with ethyl acetate (30 mL×2), washed with water (20 mL), saturated brine (20 mL), dried over anhydrous sodium sulfate, filtered, concentrated under reduced pressure and evaporated to remove the solvent. The residue was subjected to a silica gel column to obtain 2.37 g of off-white solid with a yield of 72.0%. LC-MS(APCI): m/z=395.1 (M+1)$^+$. $^1$H NMR (300 MHz, CDCl$_3$) δ 8.77 (s, 2H), 7.82-7.77 (m, 2H), 7.21-7.16 (m, 2H), 1.50 (s, 9H).

Step 5. Synthesis of Intermediate A-2

Compound 12 (2.37 g, 6.01 mmol) and dichloromethane (25 mL) were added to a 50 mL single-neck flask equipped with a magnetic stirrer, stirred to dissolve to clear, and added with trifluoroacetic acid (5 mL). The reaction was stirred at room temperature under nitrogen atmosphere for 2 hours. The solvent was evaporated under reduced pressure. The residue was added with saturated aqueous sodium bicarbonate (10 mL), and extracted with dichloromethane (20 mL×3). The organic phases were combined, dried over anhydrous sodium sulfate, filtered, and concentrated to dryness to obtain 1.50 g of yellow solid with a yield of 84.82%. LC-MS(APCI): m/z=295.1 (M+1)$^+$.

Example 3

Preparation of 4-chloro-6-(1-methyl-1H-pyrazol-4-yl)pyrrolo[2,1-f][1,2,4]triazine (Intermediate B-1)

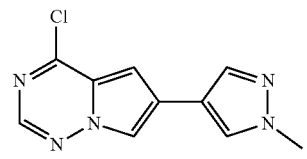

B-1

The following scheme was used for synthesis:

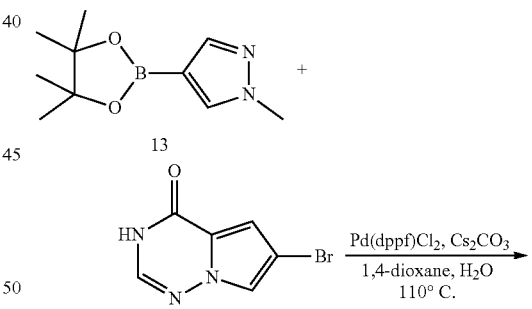

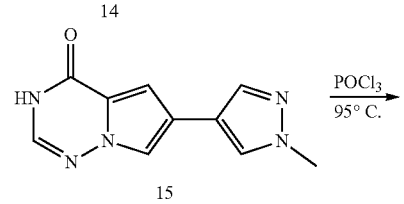

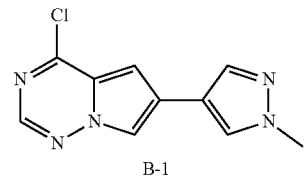

B-1

Step 1. Synthesis of Compound 15

Compound 13 (4.18 g, 20.09 mmol), compound 14 (2.15 g, 10.05 mmol), cesium carbonate (9.82 g, 30.14 mmol), Pd(dppf)Cl$_2$ (1.63 g, 2.22 mmol), 1,4-dioxane (100 mL) and water (20 mL) were added to a 100 mL single-neck flask equipped with a magnetic stirrer, evacuated and purged with nitrogen for 3 times, warmed to 110° C. overnight under nitrogen atmosphere, cooled to room temperature, and added with 80-100 mesh silica gel (50 g, 120 mL), concentrated to dryness under reduced pressure, and subjected to a silica gel column to obtain 1.2 g of yellow solid with a yield of 55.5%. LC-MS(APCI): m/z=216.1 (M+1)$^+$.

Step 2. Synthesis of Intermediate B-1

Compound 15 (1.0 g, 4.58 mmol) and phosphorus oxychloride (10 mL) were added to a 50 mL single-neck flask equipped with a magnetic stirrer, warmed to 95° C. under nitrogen atmosphere, stirred for reaction for 5 hours with the temperature kept, and cooled to room temperature. The residual phosphorus oxychloride was evaporated under reduced pressure. Dichloromethane (30 mL) and saturated aqueous sodium bicarbonate (10 mL) were added, the organic layer was separated, and the aqueous layer was extracted with dichloromethane (20 mL). The organic phases were combined, dried over anhydrous sodium sulfate, filtered, concentrated and subjected to a silica gel column to obtain 480 mg of white solid with a yield of 36.84%. LC-MS (APCI): m/z=234.1 (M+1)$^+$. $^1$H NMR (400 MHz, CDCl$_3$) δ 19 (s, 1H), 7.96 (d, J=1.6 Hz, 1H), 7.77 (s, 1H), 7.65 (s, 1H), 7.00 (d, J=1.6 Hz, 1H), 3.98 (s, 3H).

Example 4

Preparation of 4-Chloro-6-(1-(methyl-d$_3$)-1H-pyrazol-4-yl)pyrrolo[2,1-f][1,2,4]triazine (Intermediate B-2)

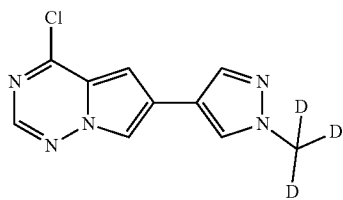

B-2

The following scheme was used for synthesis:

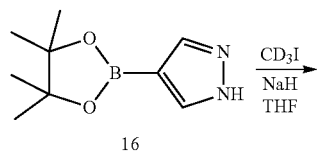

16

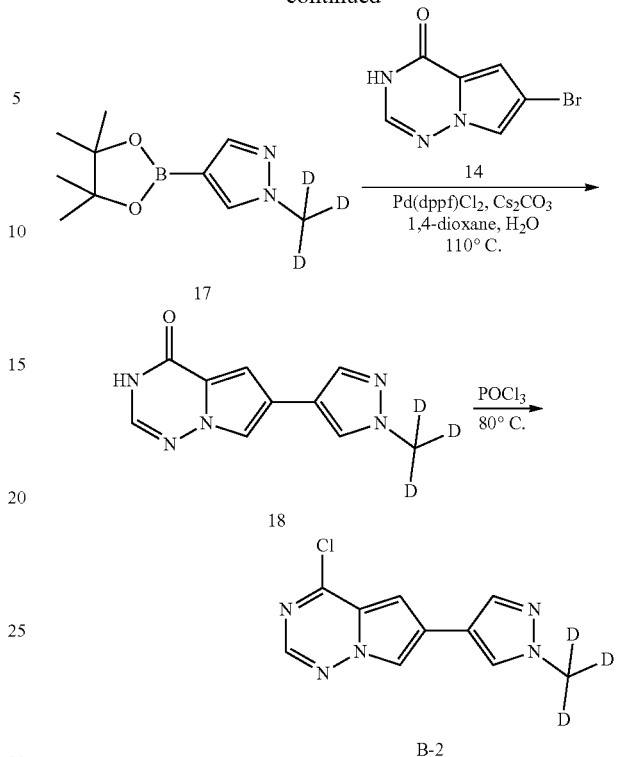

Step 1. Synthesis of Compound 17

Compound 16 (5.0 g, 25.77 mmol) and anhydrous THF (40 mL) were added to a 100 mL two-neck flask equipped with a magnetic stirrer, stirred to dissolve to clear, and slowly added with NaH (2.25 g, 51.54 mmol, 55% w/w) with ice-water bath cooling. After the addition, the reaction was stirred under nitrogen atmosphere for 10 minutes, and added dropwise with CD$_3$I (7.47 g, 51.54 mmol). After the addition, the ice bath was removed, and the reaction was stirred overnight at room temperature under nitrogen atmosphere. Methanol (5 mL) was added to quench the reaction, and then ethyl acetate (30 mL) was added to dilute the reaction solution. The insoluble solids were filtered off, and the filtrate was concentrated and subjected to a silica gel column to obtain 3.5 g of colorless oil with a yield of 64.35%. LC-MS(APCI): m/z=212.1 (M+1)$^+$.

Step 2. Synthesis of Compound 18

Compound 17 (3.49 g, 16.54 mmol), compound 14 (1.77 g, 8.27 mmol), cesium carbonate (8.08 g, 24.81 mmol), Pd(dppf)Cl$_2$ (678 mg, 0.83 mmol), 1,4-dioxane (70 mL), ethanol (15 mL) and water (10 mL) were added to a 100 mL single-neck flask equipped with a magnetic stirrer, evacuated and purged with nitrogen for 3 times, warmed to 110° C. overnight under nitrogen atmosphere, cooled to room temperature, and added with 80-100 mesh silica gel (50 g, 120 mL), concentrated to dryness under reduced pressure, and subjected to a silica gel column to obtain 1.1 g of yellow solid with a yield of 60.95%. LC-MS(APCI): m/z=219.1 (M+1)$^+$.

Step 3. Synthesis of Intermediate B-2

Compound 18 (1.0 g, 4.58 mmol) and phosphorus oxychloride (10 mL) were added to a 50 mL single-neck flask equipped with a magnetic stirrer, warmed to 95° C. under nitrogen atmosphere, stirred for reaction for 5 hours with the temperature kept, and cooled to room temperature. The residual phosphorus oxychloride was evaporated under reduced pressure. Dichloromethane (30 mL) and saturated aqueous sodium bicarbonate (10 mL) were added, the organic layer was separated, and the aqueous layer was extracted with dichloromethane (20 mL). The organic phases were combined, dried over anhydrous sodium sulfate, filtered, concentrated and subjected to a silica gel column to obtain 330 mg of white solid with a yield of 30.43%. LC-MS(APCI): m/z=237.1 (M+1)$^+$. $^1$H NMR (400 MHz, CDCl$_3$) δ 8.19 (s, 1H), 7.96 (d, J=1.6 Hz, 1H), 7.77 (s, 1H), 7.65 (s, 1H), 7.00 (d, J=1.6 Hz, 1H).

Example 5

Preparation of 1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl)pyrimidin-5-yl)ethylamine (Compound 22), (S)-1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl)pyrimidin-5-yl)ethylamine (Compound T-1-S), and (R)-1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl)pyrimidin-3-yl)ethylamine (Compound T-1-R)

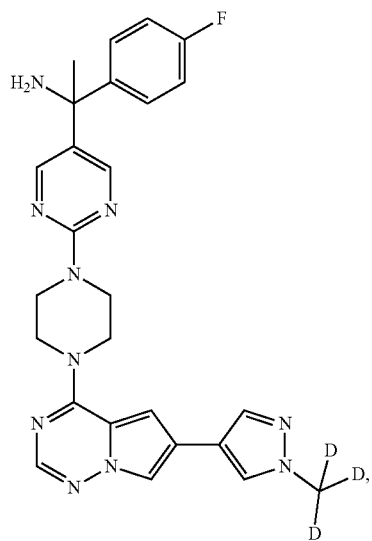

22

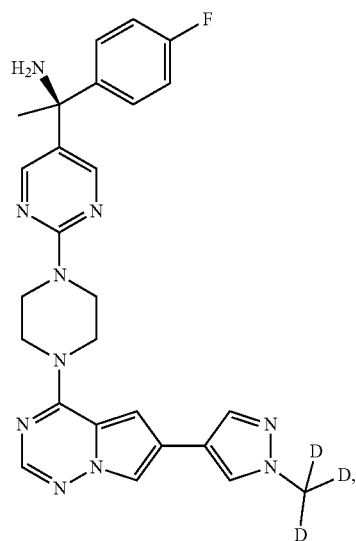

T-1-S

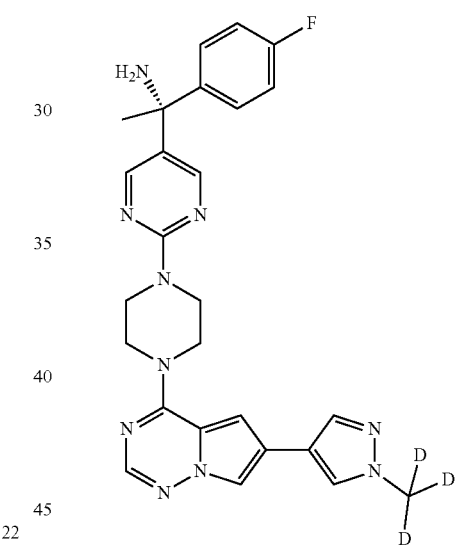

T-1-R

The following scheme was used for synthesis:

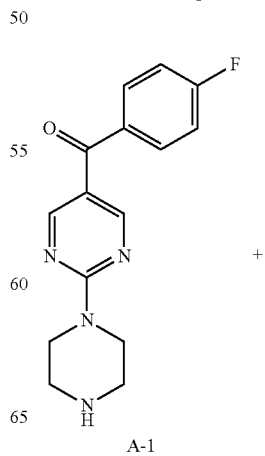

A-1

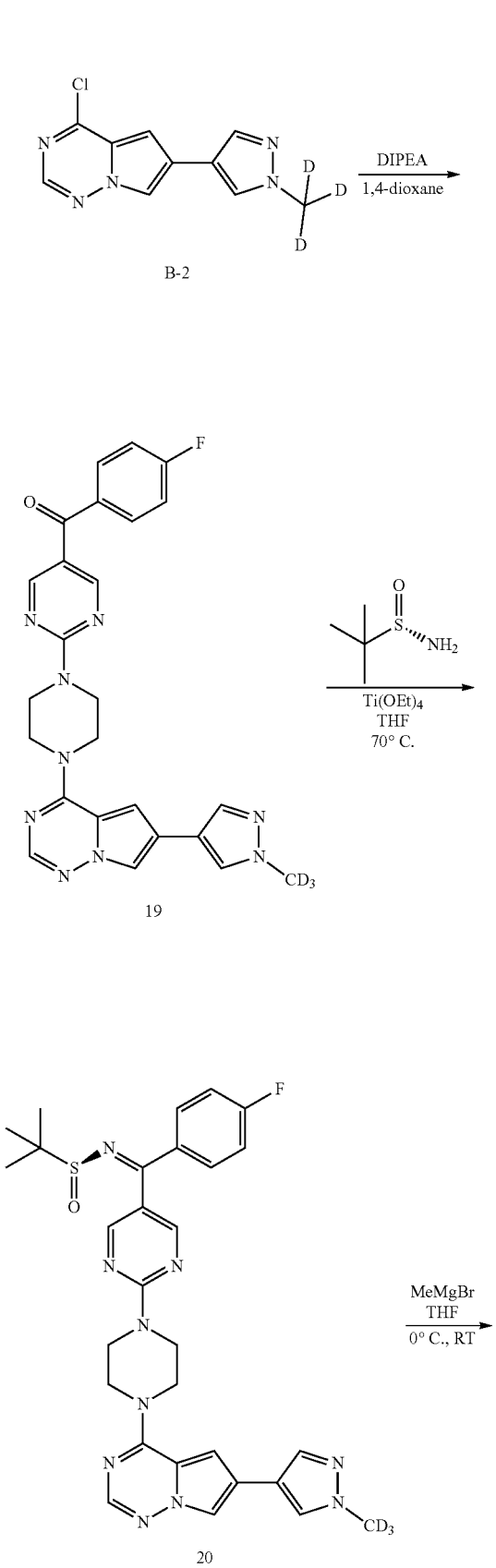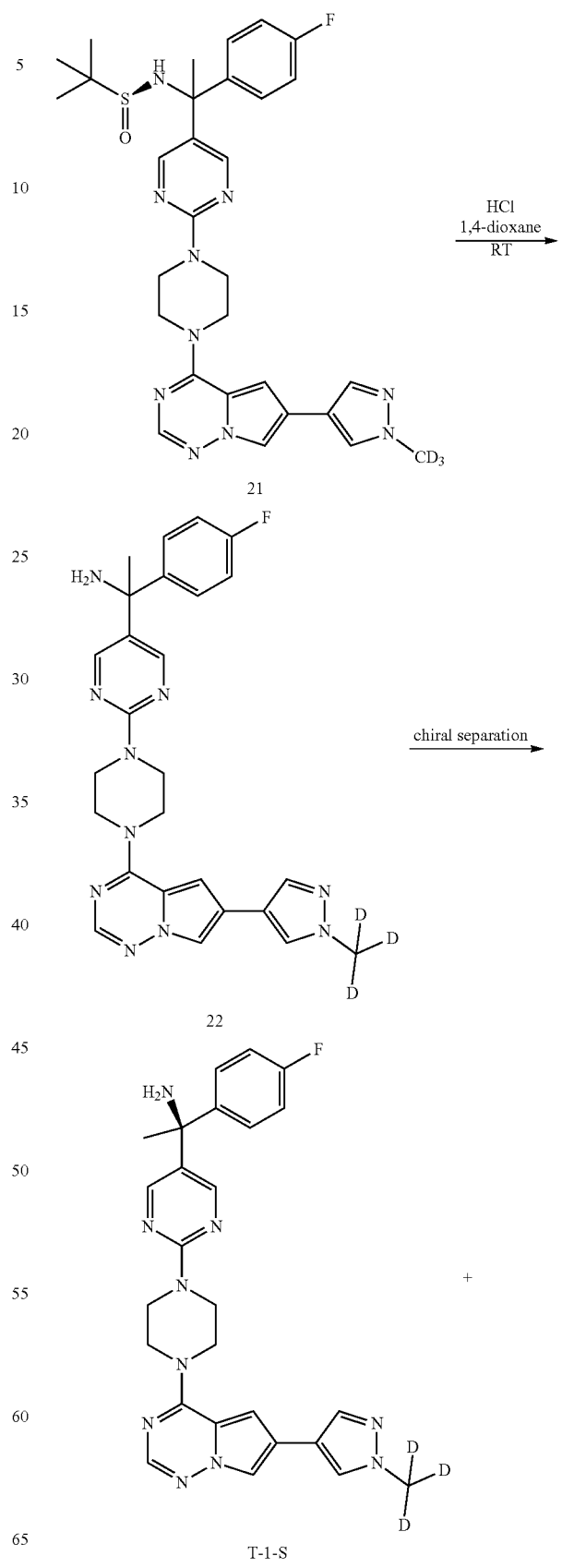

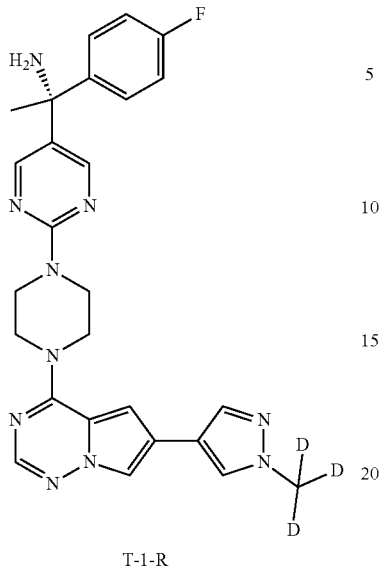

T-1-R

Step 1. Synthesis of Compound 19

Compound A-1 (261.3 mg, 0.91 mmol) and 1,4-dioxane (10 mL) were added to a 50 mL single-neck flask equipped with a magnetic stirrer, stirred to dissolve to clear, and added with DIPEA (200 mg, 1.52 mmol) and compound B-2 (180 mg, 0.76 mmol). The reaction was stirred overnight at room temperature under nitrogen atmosphere. The solvent was evaporated under reduced pressure, and the residue was subjected to a silica gel column to obtain 340 mg of yellow solid with a yield of 91.89%. LC-MS(APCI): m/z=487.1 (M+1)$^+$. $^1$H NMR (400 MHz, DMSO-D6) δ 8.82 (s, 2H), 7.83-7.79 (m, 2H), 7.73 (d, J=1.6 Hz, 1H), 7.71 (s, 1H), 7.58 (s, 1H), 7.20 (t, J=8.4 Hz, 2H), 6.80 (s, 1H), 4.09-4.07 (m, 4H), 3.90-3.88 (m, 4H).

Step 2. Synthesis of Compound 20

Compound 19 (340 mg, 0.70 mmol) and anhydrous THF (10 mL) were added to a 50 mL single-neck flask equipped with a magnetic stirrer, stirred to dissolve to clear, added with S-tert-butylsulfinamide (321 mg, 2.66 mmol) and tetraethyl titanate (526 mg, 2.31 mmol), warmed to 70° C. under nitrogen atmosphere, and stirred for reaction overnight with the temperature kept. The reaction was cooled to room temperature. The reaction was quenched with water (10 mL) and extracted with ethyl acetate (20 mL×3). Organic phases were combined, washed with water (30 mL) and saturated brine (20 mL), dried over anhydrous sodium sulfate, filtered, concentrated and subjected to a silica gel column to obtain 290 mg of yellow solid with a yield of 70.37%. LC-MS(APCI): m/z=590.3 (M+1)$^+$. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 4.19-4.16 (m, 4H), 4.06-4.04 (m, 4H), 3.78 (s, 1H), 2.08 (d, J=20.0 Hz, 3H), 1.22 (s, 9H).

Step 3. Synthesis of Compound 21

Compound 20 (290 mg, 0.49 mmol) and anhydrous THF (5 mL) were added to a 50 mL two-neck flask equipped with a magnetic stirrer, stirred to dissolve to clear, evacuated and protected with nitrogen, cooled to 0° C., and slowly added dropwise with a solution of methyl magnesium bromide in THF (1.0 mL, 3.0 mmol, 3M). After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS(APCI): m/z=606.3 (M+1)$^+$. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 4.19-4.16 (m, 4H), 4.06-4.04 (m, 4H), 3.78 (s, 1H), 2.08 (d, J=20.0 Hz, 3H), 1.22 (s, 9H).

Step 4. Synthesis of Compound 22

Compound 21 (160 mg, 0.26 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes.

The organic layer was separated, and the aqueous phase was extracted with dichloromethane (15 mL×2). The organic phases were combined, dried over anhydrous sodium sulfate, filtered, and concentrated to obtain 100 mg of white solid (Compound 22) with a yield of 75.48%. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 4.08-4.04 (m, 4H), 3.89-3.85 (m, 4H), 2.44 (br s, 1H), 1.70 (s, 3H).

Step 4. Synthesis of Compounds T-1-S and T-1-R 100 mg of compound 22 was dissolved in a mixed solvent of 30 mL of MeOH and 3 mL of DCM. The racemic compound 22 was resolved by chiral HPLC using the following separation conditions:

Chiral preparative chromatography column: CHIRALPAK IC (trade name), 4.6 mm×250 mm (inner diameter× length), Sym(filler particle size)

Column temperature: 30° C.

Flow rate: 3.0 mL/min

UV detection wavelength: 254 nm

Mobile phase: MTBE:EtOH=85:15

Compounds T-1-S (38 mg, retention time: 12.092 min, yield: 76%) and T-1-R (30 mg, retention time: 10.757 min, yield: 60%) were obtained. LC-MS(APCI): m/z=502.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 4.08-4.04 (m, 4H), 3.89-3.85 (m, 4H), 2.44 (br s, 1H), 1.70 (s, 3H).

Example 6

Preparation of 1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-2,2,2-d₃-1-amine (Compound 26), (S)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-2,2,2-d₃-1-amine (Compound T-2-S), and (R)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-2,2,2-d₃-1-amine (Compound T-2-R)

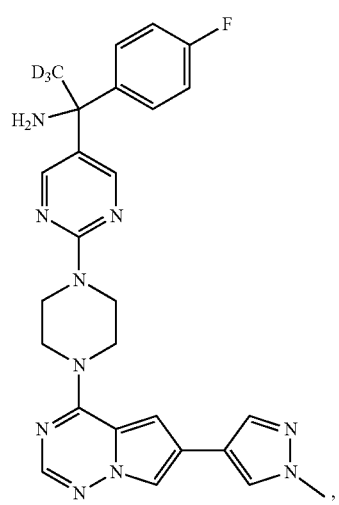

26

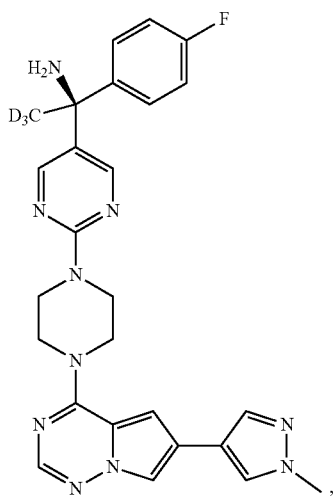

T-2-S

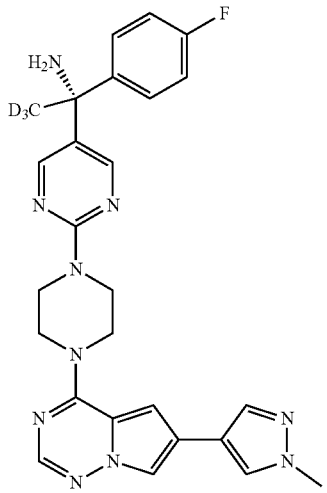

T-2-R

The following scheme was used for synthesis:

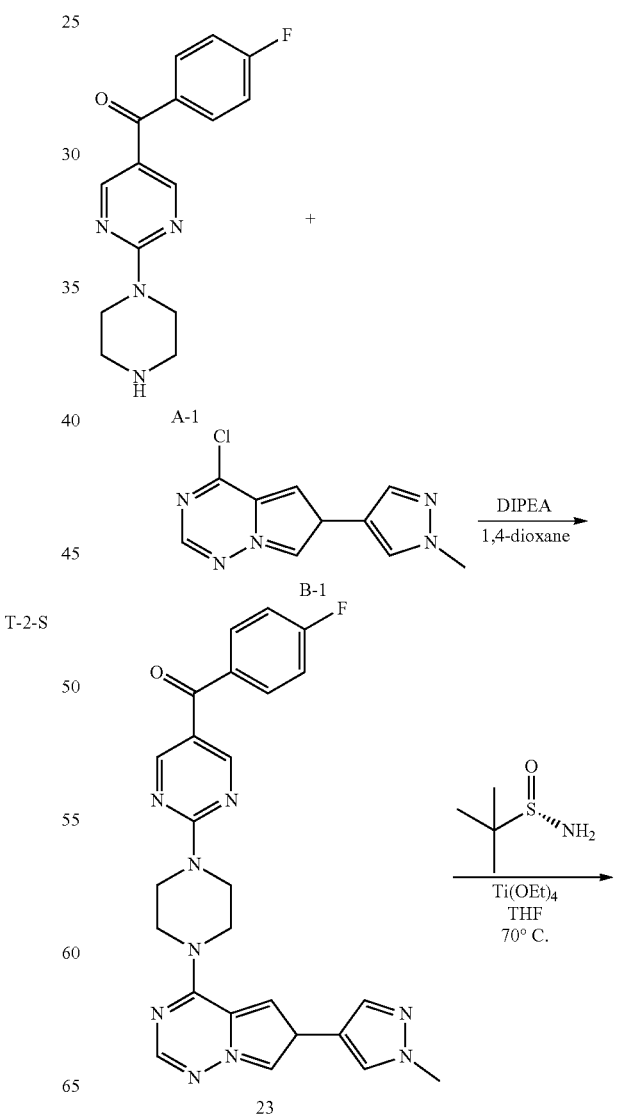

-continued
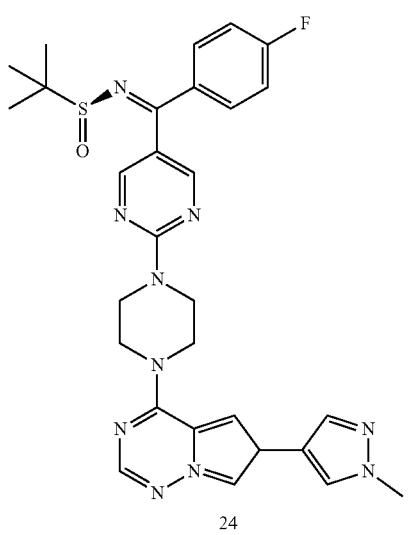
24
1. CD₃I, Mg, Et₂O, reflux
2. THF, 0° C., RT
→
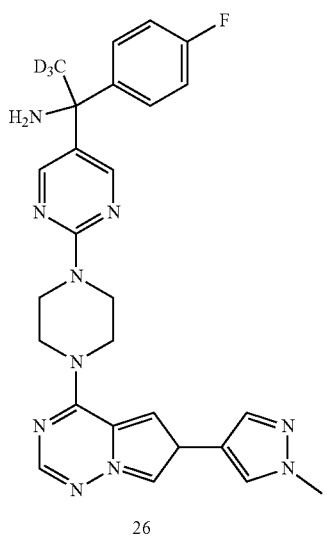
26
chiral separation →
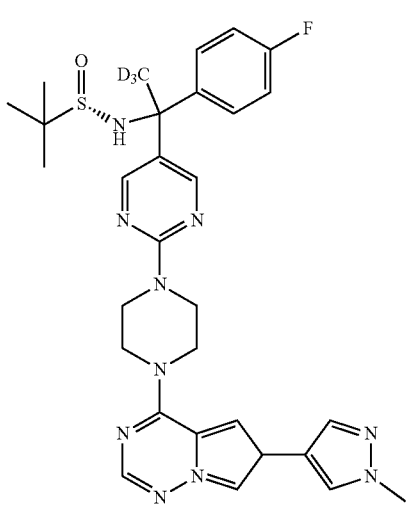
25
HCl
1,4-dioxane
RT
→
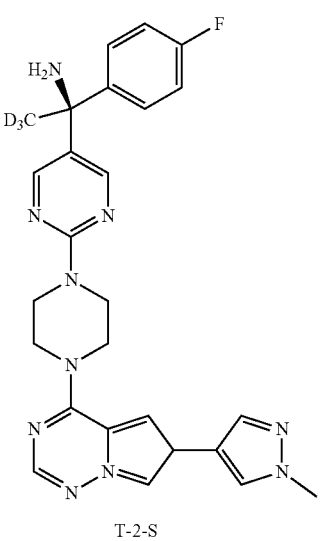
T-2-S
+
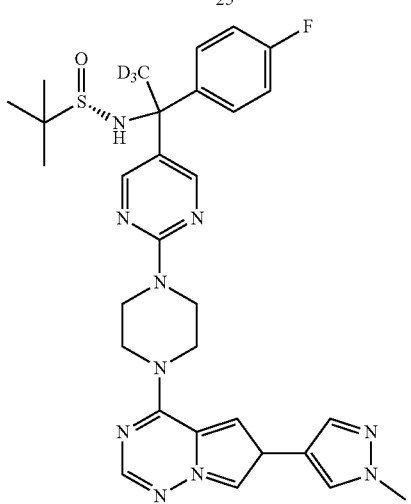
25
HCl
1,4-dioxane
RT
→
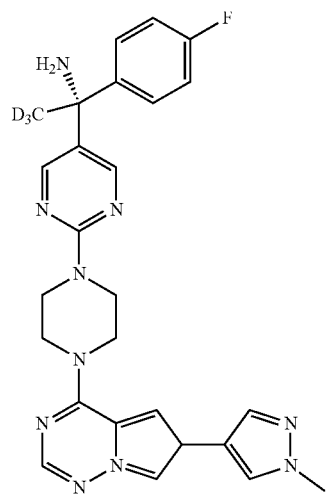
T-2-R

Step 1. Synthesis of Compound 23

Compound A-1 (261.3 mg, 0.91 mmol) and 1,4-dioxane (10 mL) were added to a 50 mL single-neck flask equipped with a magnetic stirrer, stirred to dissolve to clear, and added with DIPEA (200 mg, 1.52 mmol) and compound B-1 (180 mg, 0.76 mmol). The reaction was stirred overnight at room temperature under nitrogen atmosphere. The solvent was evaporated under reduced pressure, and the residue was subjected to a silica gel column to obtain 340 mg of yellow solid with a yield of 91.89%. LC-MS(APCI): m/z=487.1 (M+1)$^+$. $^1$H NMR (400 MHz, DMSO-D$_6$) δ 8.82 (s, 2H), 7.83-7.79 (m, 2H), 7.73 (d, J=1.6 Hz, 1H), 7.71 (s, 1H), 7.58 (s, 1H), 7.20 (t, J=8.4 Hz, 2H), 6.80 (s, 1H), 4.09-4.07 (m, 4H), 3.96 (s, 3H), 3.90-3.88 (m, 4H).

Step 2. Synthesis of Compound 24

Compound 23 (340 mg, 0.70 mmol) and anhydrous THF (10 mL) were added to a 50 mL single-neck flask equipped with a magnetic stirrer and a condenser tube, stirred to dissolve to clear, added with S-tert-butylsulfinamide (321 mg, 2.66 mmol) and tetraethyl titanate (526 mg, 2.31 mmol), warmed to 70° C. under nitrogen atmosphere, and stirred for reaction overnight with the temperature kept. The reaction was cooled to room temperature. The reaction was quenched with water (10 mL) and extracted with ethyl acetate (20 mL×3). Organic phases were combined, washed with water (30 mL) and saturated brine (20 mL), dried over anhydrous sodium sulfate, filtered, concentrated and subjected to a silica gel column to obtain 290 mg of yellow solid with a yield of 70.37%. LC-MS(APCI): m/z=587.3 (M+1)$^+$. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 4.19-4.16 (m, 4H), 4.06-4.04 (m, 4H), 3.95 (s, 3H), 3.78 (s, 1H), 2.08 (d, J=20.0 Hz, 3H), 1.22 (s, 9H).

Step 3. Synthesis of Compound 25

Magnesium powder (140 mg, 5.79 mmol) was added to a 50 mL two-neck flask equipped with a magnetic stirrer and condenser tube, evacuated and protected with nitrogen, added with ethyl ether (5 mL) and deuterated methyl iodide (700 mg, 4.83 mmol) via a syringe, heated to reflux, stirred for reaction for 2 hours with the temperature kept, and cooled to room temperature.

Compound 24 (290 mg, 0.49 mmol) and anhydrous THF (5 mL) were added to another 50 mL two-neck flask equipped with a magnetic stirrer, stirred to dissolve to clear, evacuated and protected with nitrogen, cooled to 0° C., and slowly added dropwise with the solution of CD$_3$MgI in ether prepared above. After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS (APCI): m/=606.3 (M+1)$^+$. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 4.19-4.16 (m, 4H), 4.06-4.04 (m, 4H), 3.97 (s, 3H), 3.78 (s, 1H), 1.22 (s, 9H).

Step 4. Synthesis of Compound 26

Compound 25 (160 mg, 0.26 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes. The organic layer was separated, and the aqueous phase was extracted with dichloromethane (15 mL×2). The organic phases were combined, dried over anhydrous sodium sulfate, filtered, and concentrated to obtain 100 mg of white solid with a yield of 75.48%. LC-MS(APCI): m/z=502.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 4.08-4.04 (m, 4H), 3.89-3.85 (m, 4H), 3.84 (s, 3H), 2.44 (br s, 1H).

Step 5. Synthesis of Compounds T-2-S and T-2-R 100 mg of compound 26 was dissolved in a mixed solvent of 30 mL of MeOH and 3 mL of DCM. The racemic compound 26 was resolved by chiral HPLC using the following separation conditions:

Chiral preparative chromatography column: CHIRALPAK IC (trade name), 4.6 mm×250 mm (inner diameter× length), 5 μm (filler particle size)
Column temperature: 30° C.
Flow rate: 3.0 mL/min
UV detection wavelength: 254 nm
Mobile phase: MTBE:EtOH=85:15

Compounds T-2-S (38 mg, retention time: 12.092 min, yield: 76%) and T-2-R (30 mg, retention time: 10.757 min, yield: 60%) were obtained. LC-MS(APCI): m/z=502.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 4.08-4.04 (m, 4H), 3.89-3.85 (m, 4H), 3.84 (s, 3H), 2.44 (br s, 1H).

Example 7

Preparation of 1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl)pyrimidin-5-yl)ethan-2,2,2-d$_3$-1-amine (Compound 28), (S)-1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl)pyrimidin-5-yl)ethan-2,2,2-d$_3$-1-amine (Compound T-3-S), and (R)-1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl)pyrimidin-5-yl)ethan-2,2,2-d$_3$-1-amine (Compound T-3-R)

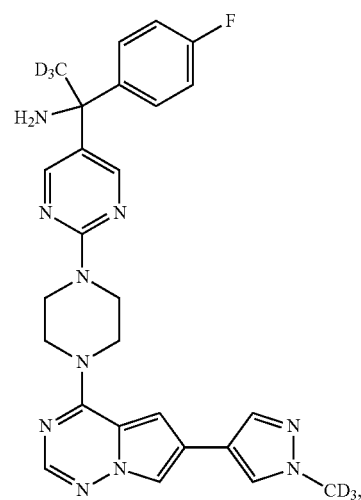

28

57
-continued
T-3-S
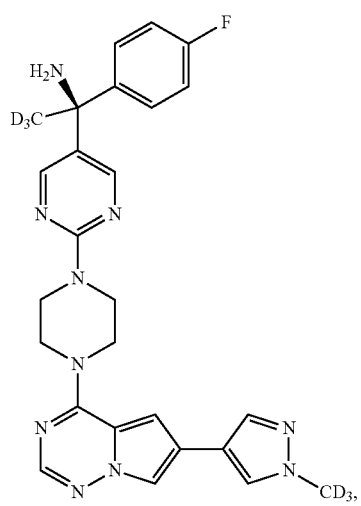
T-3-R
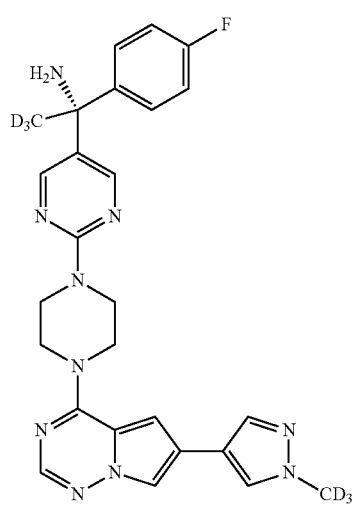
The following scheme was used for synthesis:
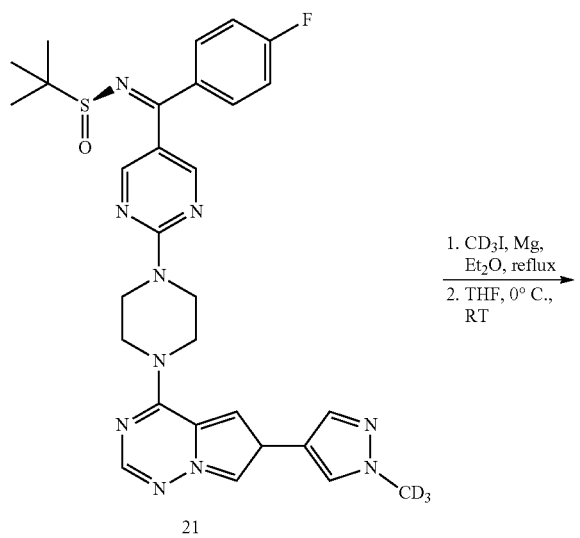
21
1. CD₃I, Mg, Et₂O, reflux
2. THF, 0° C., RT
58
-continued
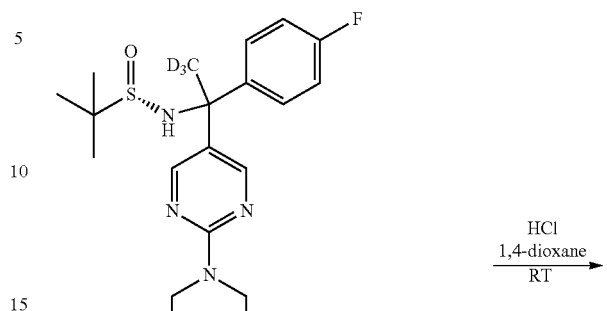
27
HCl
1,4-dioxane
RT
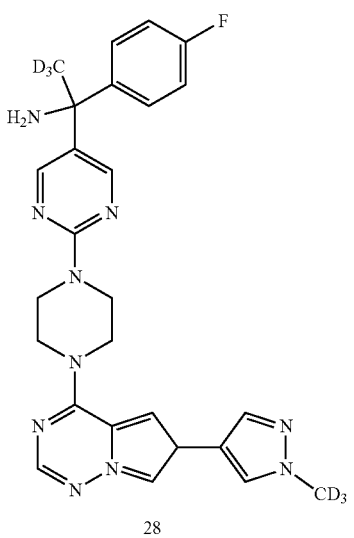
28
chiral separation
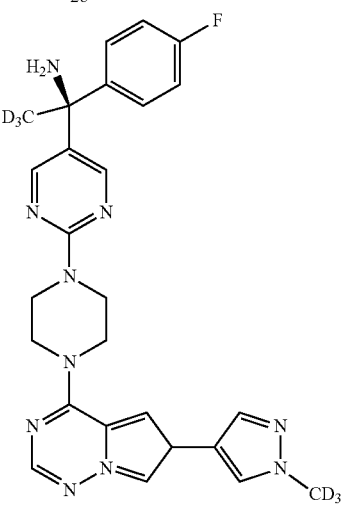
T-3-S
+

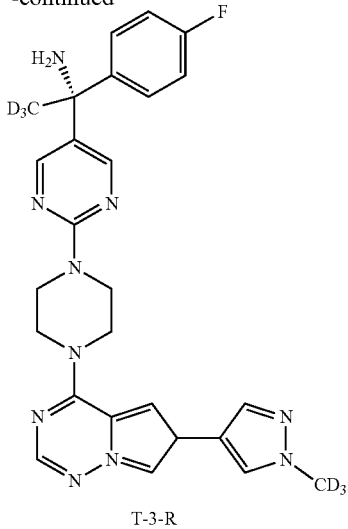

T-3-R

Step 1. Synthesis of Compound 27

Magnesium powder (140 mg, 5.79 mmol) was added to a 50 mL two-neck flask equipped with a magnetic stirrer and condenser tube, evacuated and protected with nitrogen, added with ethyl ether (5 mL) and deuterated methyl iodide (700 mg, 4.83 mmol) via a syringe, heated to reflux, stirred for reaction for 2 hours with the temperature kept, and cooled to room temperature.

Compound 21 (290 mg, 0.49 mmol) and anhydrous THF (5 mL) were added to another 50 mL two-neck flask equipped with a magnetic stirrer, stirred to dissolve to clear, evacuated and protected with nitrogen, cooled to 0° C., and slowly added dropwise with the solution of $CD_3MgI$ in ether prepared above. After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS (APCI): m/z=609.3 (M+1)$^+$. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 4.19-4.16 (m, 4H), 4.06-4.04 (m, 4H), 3.78 (s, 1H), 1.22 (s, 9H).

Step 2. Synthesis of Compound 28

Compound 27 (160 mg, 0.26 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes. The organic layer was separated, and the aqueous phase was extracted with dichloromethane (15 mL×2). The organic phases were combined, dried over anhydrous sodium sulfate, filtered, and concentrated to obtain 100 mg of white solid with a yield of 75.48%. LC-MS(APCI): m/z=502.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 4.08-4.04 (m, 4H), 3.89-3.85 (m, 4H), 2.44 (br s, 1H).

Step 3. Synthesis of Compounds T-3-S and T-3-R 100 mg of compound 28 was dissolved in a mixed solvent of 30 mL of MeOH and 3 mL of DCM. The racemic compound 28 was resolved by chiral HPLC using the following separation conditions:

Chiral preparative chromatography column: CHIRAL-PAK IC (trade name), 4.6 mm×250 mm (inner diameter× length), 5 μm (filler particle size)

Column temperature: 30° C.

Flow rate: 3.0 mL/min

UV detection wavelength: 254 nm

Mobile phase: MTBE:EtOH=85:15

Compounds T-3-S (38 mg, retention time: 12.092 min, yield: 76%) and T-3-R (30 mg, retention time: 10.757 min, yield: 60%) were obtained. LC-MS(APCI): m/z=502.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 4.08-4.04 (m, 4H), 3.89-3.85 (m, 4H), 2.44 (br s, 1H).

Example 8

Preparation of 1-(4-fluorophenyl)-1-(2-(4-(6-(1-methyl-1H-pyrazol-4-yl)pyrrolo[2,1-f][1,2,4]triazin-4-yl)piperazin-1-yl-2,2,3,3,5,5,6,6-d$_8$)pyrimidin-5-yl)ethylamine (Compound 32), (S)-1-(4-fluorophenyl)-1-(2-(4-(6-(1-methyl-1H-pyrazol-4-yl)pyrrolo[2,1-f][1,2,4]triazin-4-yl)piperazin-1-yl-2,2,3,3,5,5,6,6-d$_8$)pyrimidin-5-yl)ethylamine (Compound T-4-S), and (R)-1-(4-fluorophenyl)-1-(2-(4-(6-(1-methyl-1H-pyrazol-4-yl)pyrrolo[2,1-f][1,2,4]triazin-4-yl)piperazin-1-yl-2,2,3,3,5,5,6,6-d$_8$)pyrimidin-5-yl)ethylamine (Compound T-4-R)

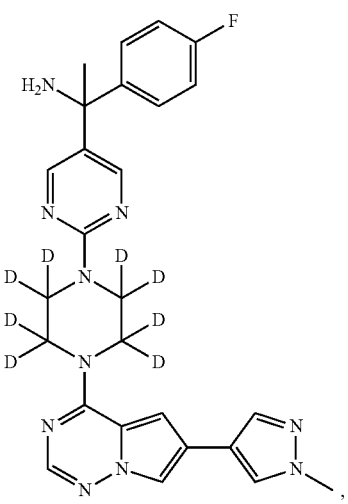

28

-continued
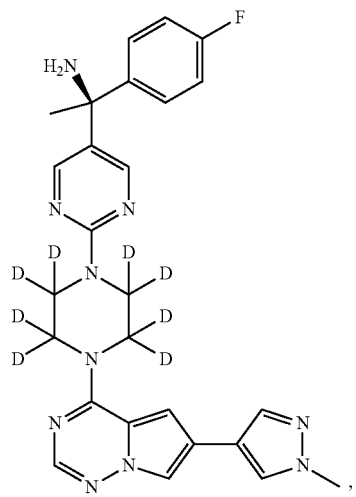
T-4-S
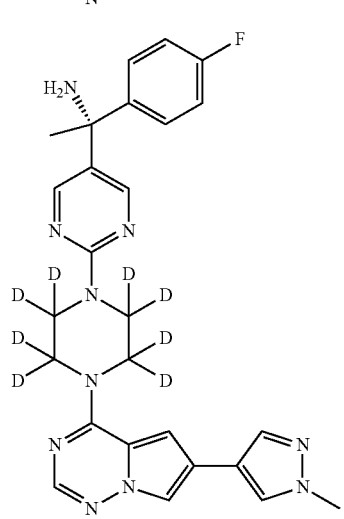
T-4-R
The following scheme was used for synthesis:
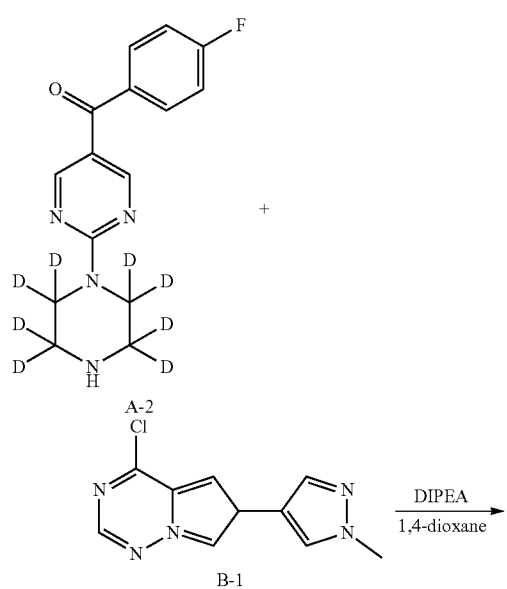
-continued
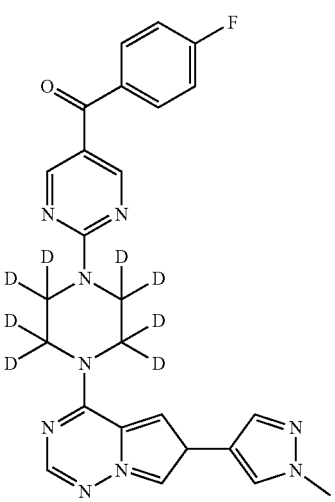 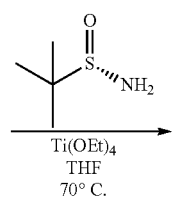
29
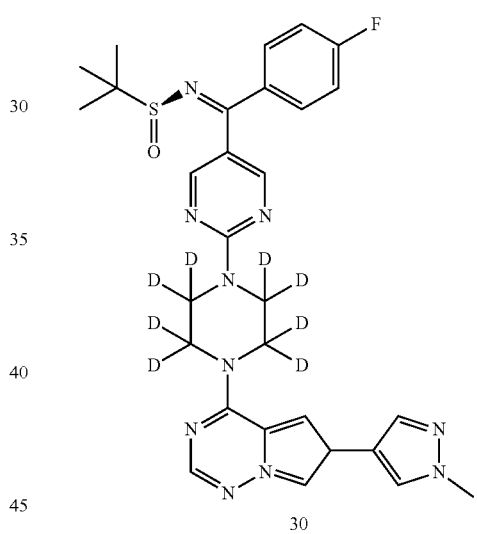 
30
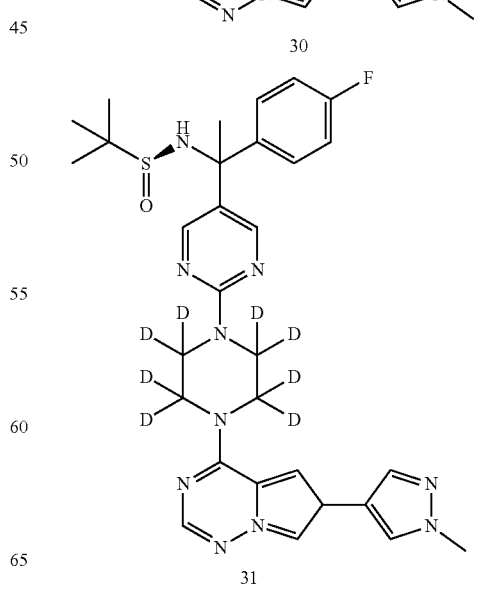 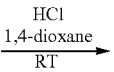
31

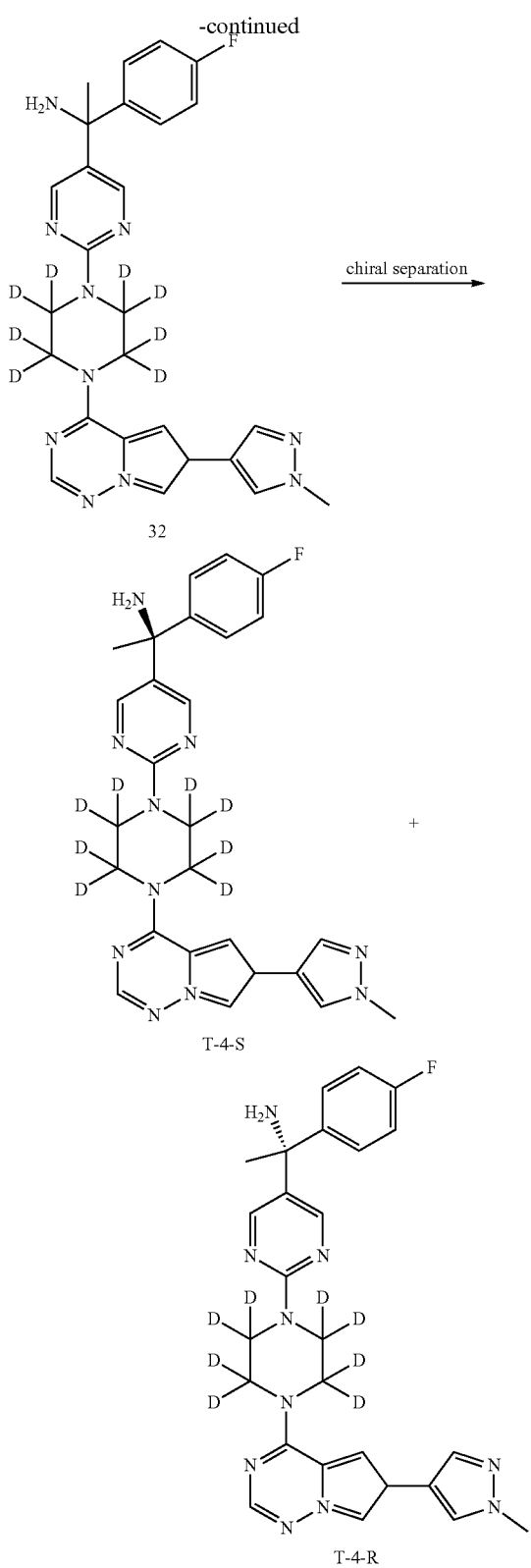

Step 1. Synthesis of Compound 29

Compound A-2 (261.3 mg, 0.88 mmol) and 1,4-dioxane (10 mL) were added to a 50 mL single-neck flask equipped with a magnetic stirrer, stirred to dissolve to clear, and added with DIPEA (200 mg, 1.52 mmol) and compound B-1 (200 mg, 0.88 mmol). The reaction was stirred overnight at room temperature under nitrogen atmosphere. The solvent was evaporated under reduced pressure, and the residue was subjected to a silica gel column to obtain 340 mg of yellow solid with a yield of 78.7%. LC-MS(APCI): m/z=492.1 (M+1)+. $^1$H NMR (400 MHz, DMSO-D$_6$) δ 8.82 (s, 2H), 7.83-7.79 (m, 2H), 7.73 (d, J=1.6 Hz, 1H), 7.71 (s, 1H), 7.58 (s, 1H), 7.20 (t, J=8.4 Hz, 2H), 6.80 (s, 1H), 3.93 (s, 3H).

Step 2. Synthesis of Compound 30

Compound 29 (340 mg, 0.68 mmol) and anhydrous THF (10 mL) were added to a 50 mL single-neck flask equipped with a magnetic stirrer, stirred to dissolve to clear, added with S-tert-butylsulfinamide (321 mg, 2.66 mmol) and tetraethyl titanate (526 mg, 2.31 mmol), warmed to 70° C. under nitrogen atmosphere, and stirred for reaction overnight with the temperature kept. The reaction was cooled to room temperature. The reaction was quenched with water (10 mL) and extracted with ethyl acetate (20 mL×3). Organic phases were combined, washed with water (30 mL) and saturated brine (20 mL), dried over anhydrous sodium sulfate, filtered, concentrated and subjected to a silica gel column to obtain 290 mg of yellow solid with a yield of 70.37%. LC-MS(APCI): m/z=595.3 (M+1)+. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 3.94 (s, 3H), 3.78 (s, 1H), 2.08 (d, J=20.0 Hz, 3H), 1.22 (s, 9H).

Step 3. Synthesis of Compound 31

Compound 30 (290 mg, 0.47 mmol) and anhydrous THF (5 mL) were added to a 50 mL two-neck flask equipped with a magnetic stirrer, stirred to dissolve to clear, evacuated and protected with nitrogen, cooled to 0° C., and slowly added dropwise with a solution of methyl magnesium bromide in THF (1.0 mL, 3.0 mmol, 3M). After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS(APCI): m/z=611.3 (M+1)+. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 3.91 (s, 3H), 3.78 (s, 1H), 2.08 (d, J=20.0 Hz, 3H), 1.22 (s, 9H).

Step 4. Synthesis of Compound 32

Compound 31 (160 mg, 0.24 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes. The organic layer was separated, and the aqueous phase was extracted with dichloromethane (15 mL×2). The organic phases were combined, dried over anhydrous sodium sulfate, filtered, and concentrated to obtain 100 mg of white solid with a yield of 75.48%. LC-MS(APCI): m/z=507.3 (M+1)+. $^1$H NMR (500 MHz, DMSO-D6) δ 8.38 (s, 2H), 8.00 (s, 1H), 7.95 (d, J=1.5H), 1H), 7.86 (s, 1H), 7.80 (s, 1H), 7.46-7.41 (m, 2H), 7.20 (d, J=1.5 Hz, 1H), 7.11-7.05 (m, 1H), 3.84 (s, 3H), 2.43 (br s, 1H), 1.73 (s, 3H).

Step 5. Synthesis of Compounds T-4-S and T-4-R 100 mg of compound 32 was dissolved in a mixed solvent of 30 mL of MeOH and 3 mL of DCM. The racemic compound 32 was resolved by chiral HPLC using the following separation conditions:

Chiral preparative chromatography column: CHIRAL-PAK IC (trade name), 4.6 mm×250 mm (inner diameter× length), 5 μm (filler particle size)

Column temperature: 30° C.

Flow rate: 3.0 mL/min

UV detection wavelength: 254 nm

Mobile phase: MTBE:EtOH=85:15

Compounds T-4-S (38 mg, retention time: 12.092 min, yield: 76%) and T-4-R (30 mg, retention time: 10.757 min, yield: 60%) were obtained. LC-MS(APCI): m/z=507.3 (M+1)+. $^1$H NMR (500 MHz, DMSO-D6) δ 8.38 (s, 2H), 8.00 (s, 1H), 7.95 (d, J=1.5 Hz, 1H), 7.86 (s, 1H), 7.80 (s, 1H), 7.46-7.41 (m, 2H), 7.20 (d, J=1.5 Hz, 1H), 7.11-7.05 (m, 1H), 3.84 (s, 3H), 2.43 (br s, 1H), 1.73 (s, 3H).

Example 9

Preparation of 1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl-2,2,3,3,5,5,6,6-d$_8$)pyrimidin-5-yl)ethylamine (Compound 36), (S)-1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl-2,2,3,3,5,5,6,6-d$_8$)pyrimidin-5-yl)ethylamine (Compound T-5-S), and (R)-1-(4-fluorophenyl)-1-(2-(4-(6-(1-(methyl-d$_3$)-1H-pyrazol-4-yl)pyrrolo[2,1-f][1,2,4]triazin-4-yl)piperazin-1-yl-2,2,3,3,5,5,6,6-d$_8$)pyrimidin-5-yl)ethylamine (Compound T-5-R)

36

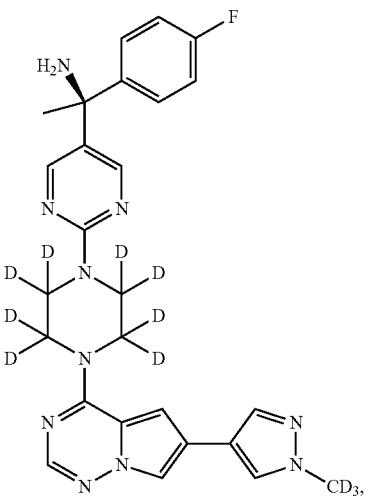

T-5-S

-continued

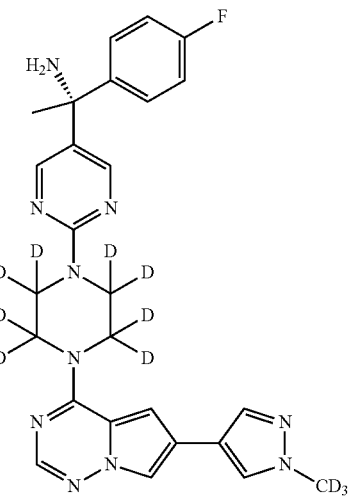

T-5-R

The following scheme was used for synthesis:

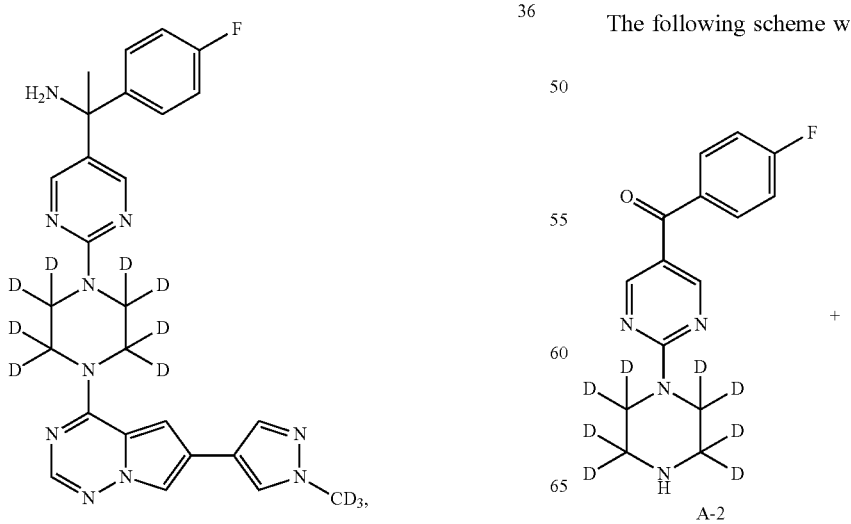

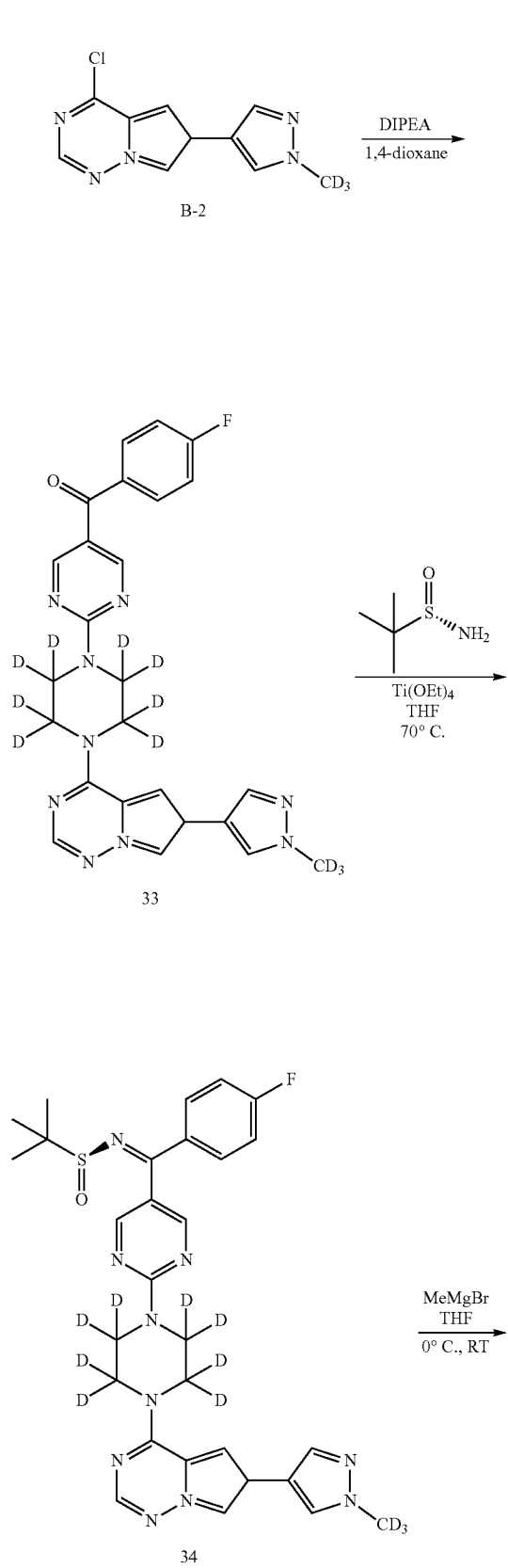
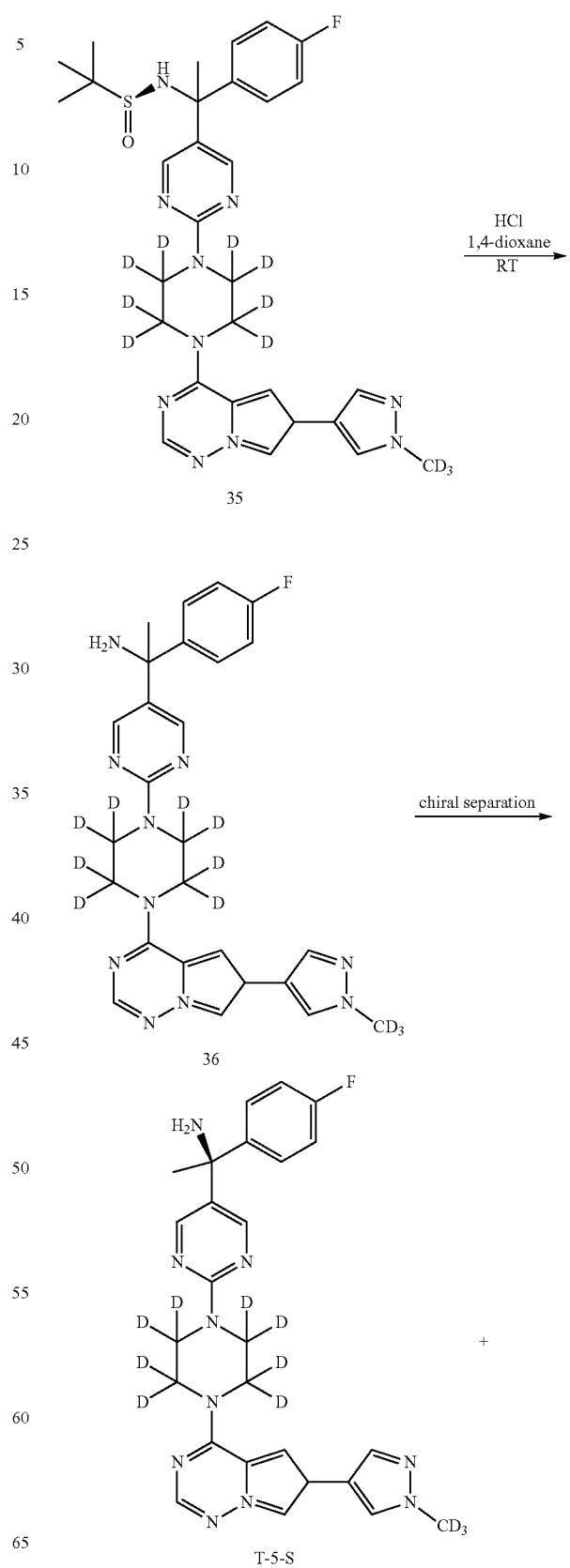

-continued

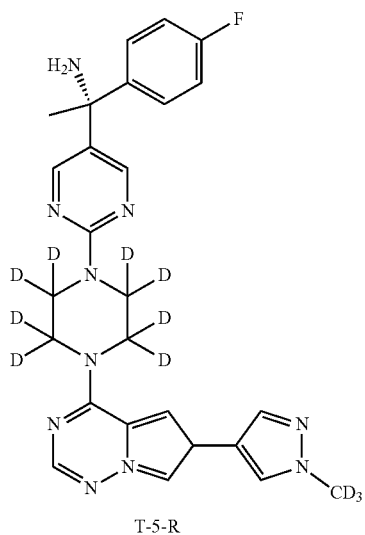
T-5-R

Step 1. Synthesis of Compound 33

Compound A-2 (261.3 mg, 0.88 mmol) and 1,4-dioxane (10 mL) were added to a 50 mL single-neck flask equipped with a magnetic stirrer, stirred to dissolve to clear, and added with DIPEA (200 mg, 1.52 mmol) and compound B-2 (200 mg, 0.89 mmol). The reaction was stirred overnight at room temperature under nitrogen atmosphere. The solvent was evaporated under reduced pressure, and the residue was subjected to a silica gel column to obtain 340 mg of yellow solid with a yield of 78.7%. LC-MS(APCI): m/z=495.1 (M+1)$^+$. $^1$H NMR (400 MHz, DMSO-D6) δ 8.82 (s, 2H), 7.83-7.79 (m, 2H), 7.73 (d, J=1.6 Hz, 1H), 7.71 (s, 1H), 7.58 (s, 1H), 7.20 (t, J=8.4 Hz, 2H), 6.80 (s, 1H).

Step 2. Synthesis of Compound 34

Compound 33 (340 mg, 0.68 mmol) and anhydrous THF (10 mL) were added to a 50 mL single-neck flask equipped with a magnetic stirrer, stirred to dissolve to clear, added with S-tert-butylsulfinamide (321 mg, 2.66 mmol) and tetraethyl titanate (526 mg, 2.31 mmol), warmed to 70° C. under nitrogen atmosphere, and stirred for reaction overnight with the temperature kept. The reaction was cooled to room temperature. The reaction was quenched with water (10 mL) and extracted with ethyl acetate (20 mL×3). Organic phases were combined, washed with water (30 mL) and saturated brine (20 mL), dried over anhydrous sodium sulfate, filtered, concentrated and subjected to a silica gel column to obtain 290 mg of yellow solid with a yield of 70.37%. LC-MS(APCI): m/z=598.3 (M+1)$^+$. 1H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 3.78 (s, 1H), 2.08 (d, J=20.0 Hz, 3H), 1.22 (s, 9H).

Step 3. Synthesis of Compound 35

Compound 34 (290 mg, 0.47 mmol) and anhydrous THF (5 mL) were added to a 50 mL two-neck flask equipped with a magnetic stirrer, stirred to dissolve to clear, evacuated and protected with nitrogen, cooled to 0° C., and slowly added dropwise with a solution of methyl magnesium bromide in THF (1.0 mL, 3.0 mmol, 3M). After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS(APCI): m/z=614.3 (M+1)+. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 3.78 (s, 1H), 2.08 (d, J=20.0 Hz, 3H), 1.22 (s, 9H).

Step 4. Synthesis of Compound 36

Compound 35 (160 mg, 0.24 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes. The organic layer was separated, and the aqueous phase was extracted with dichloromethane (15 mL×2). The organic phases were combined, dried over anhydrous sodium sulfate, filtered, and concentrated to obtain 100 mg of white solid with a yield of 75.48%. LC-MS(APCI): m/z=510.3 (M+1)$^+$. $^1$H NMR (500 MHz, DMSO-D6) δ 8.38 (s, 2H), 8.00 (s, 1H), 7.95 (d, J=1.5 Hz, 1H), 7.86 (s, 1H), 7.80 (s, 1H), 7.46-7.41 (m, 2H), 7.20 (d, J=1.5 Hz, 1H), 7.11-7.05 (m, 1H), 2.55 (br s, 1H), 1.73 (s, 3H).

Step 5. Synthesis of Compounds T-5-S and T-5-R 100 mg of compound 36 was dissolved in a mixed solvent of 30 mL of MeOH and 3 mL of DCM. The racemic compound 36 was resolved by chiral HPLC using the following separation conditions:

Chiral preparative chromatography column: CHIRAL-PAK IC (trade name), 4.6 mm×250 mm (inner diameter× length), 5 μm (filler particle size)

Column temperature: 30° C.

Flow rate: 3.0 mL/min

UV detection wavelength: 254 nm

Mobile phase: MTBE:EtOH=85:15

Compounds T-5-S (38 mg, retention time: 12.092 min, yield: 76%) and T-5-R (30 mg, retention time: 10.757 min, yield: 60%) were obtained. LC-MS(APCI): m/z=510.3 (M+1)$^+$. $^1$H NMR (500 MHz, DMSO-D6) δ 8.38 (s, 2H), 8.00 (s, 1H), 7.95 (d, J=1.5 Hz, 1H), 7.86 (s, 1H), 7.80 (s, 1H), 7.46-7.41 (m, 2H), 7.20 (d, J=1.5 Hz, 1H), 7.11-7.05 (m, 1H), 2.55 (br s, 1H), 1.73 (s, 3H).

Example 10

Preparation of 1-(4-fluorophenyl)-1-(2-(4-(6-(1-methyl-1H-pyrazol-4-yl)pyrrolo[2,1-f][1,2,4]triazin-4-yl)piperazin-1-yl-2,2,3,3,5,5,6,6-d$_8$)pyrimidin-5-yl)ethan-2,2,2-d$_{3-1}$-amine (Compound 38), (S)-1-(4-fluorophenyl)-1-(2-(4-(6-(1-methyl-1H-pyrazol-4-yl)pyrrolo[2,1-f][1,2,4]triazin-4-yl)piperazin-1-yl-2,2,3,3,5,5,6,6-d$_8$)pyrimidin-5-yl)ethan-2,2,2-d$_{3-1}$-amine (Compound T-6-S), and (R)-1-(4-fluorophenyl)-1-(2-(4-(6-(1-methyl-1H-pyrazol-4-yl)pyrrolo[2,1-f][1,2,4]triazin-4-yl)piperazin-1-yl-2,2,3,3,5,5,6,6-d$_8$)pyrimidin-5-yl)ethan-2,2,2-d$_{3-1}$-amine (Compound T-6-R)

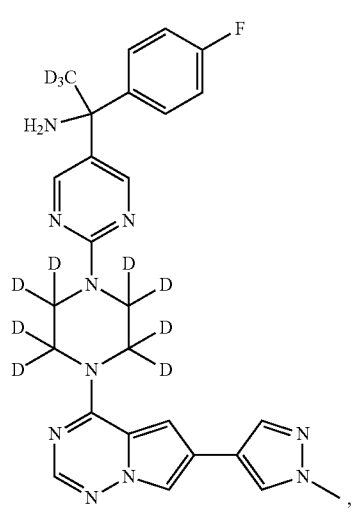

38

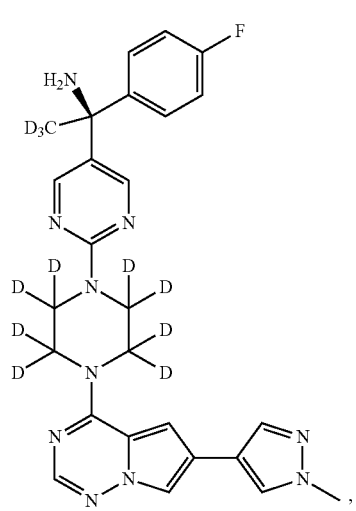

T-6-S

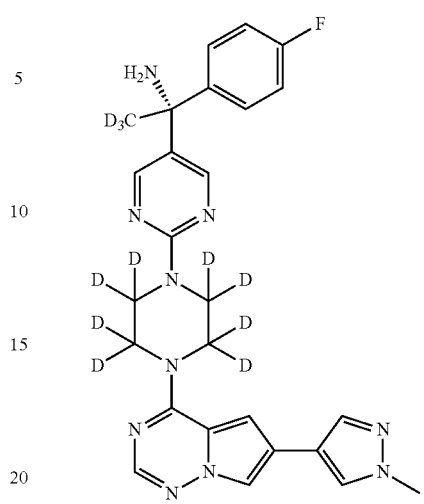

T-6-R

The following scheme was used for synthesis:

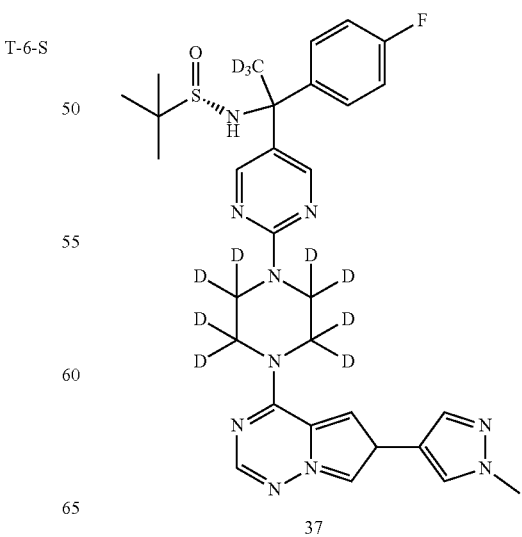

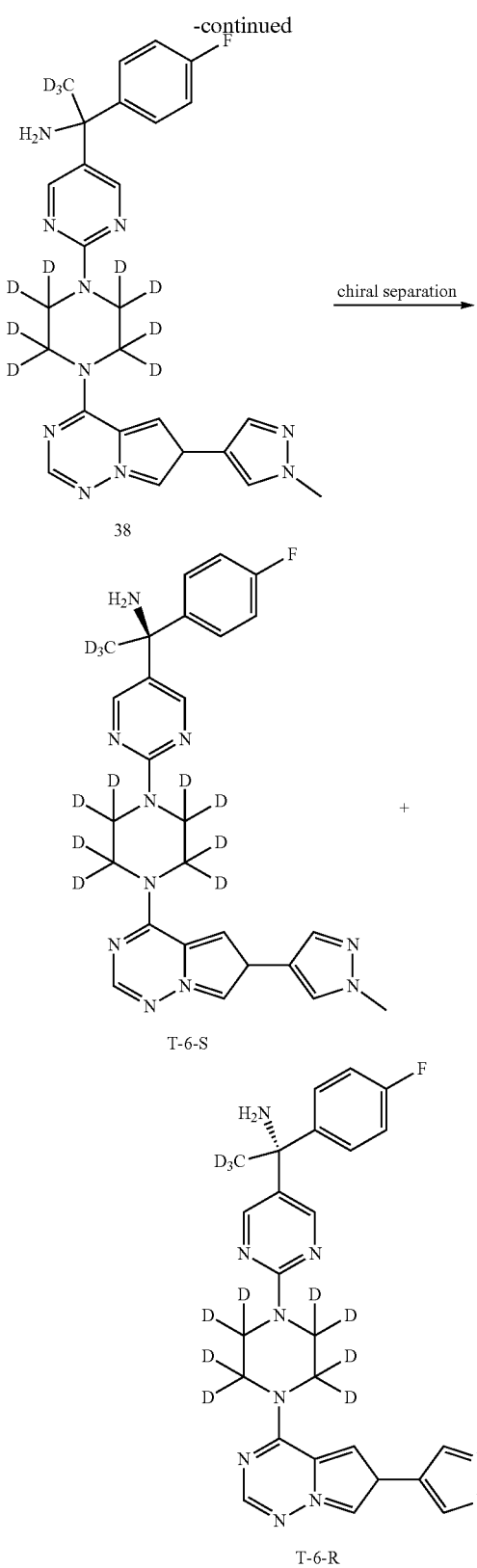

38

T-6-S

T-6-R

Step 1. Synthesis of Compound 37

Magnesium powder (140 mg, 5.79 mmol) was added to a 50 mL two-neck flask equipped with a magnetic stirrer and condenser tube, evacuated and protected with nitrogen, added with ethyl ether (5 mL) and deuterated methyl iodide (700 mg, 4.83 mmol) via a syringe, heated to reflux, stirred for reaction for 2 hours with the temperature kept, and cooled to room temperature.

Compound 31 (290 mg, 0.47 mmol) and anhydrous THF (5 mL) were added to another 50 mL two-neck flask equipped with a magnetic stirrer, stirred to dissolve to clear, evacuated and protected with nitrogen, cooled to 0° C., and slowly added dropwise with the solution of CD$_3$MgI in ether prepared above. After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS (APCI): m/z=614.3 (M+1)$^+$. $^1$H NMR (400 MHz, CDCl$_3$) δ 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 3.94 (s, 3H), 3.78 (s, 1H), 1.22 (s, 9H).

Step 2. Synthesis of Compound 38

Compound 37 (160 mg, 0.24 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes. The organic layer was separated, and the aqueous phase was extracted with dichloromethane (15 mL×2). The organic phases were combined, dried over anhydrous sodium sulfate, filtered, and concentrated to obtain 100 mg of white solid with a yield of 75.48%. LC-MS(APCI): m/z=510.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 3.85 (s, 3H), 2.44 (br s, 2H).

Step 3. Synthesis of Compounds T-6-S and T-6-R 100 mg of compound 38 was dissolved in a mixed solvent of 30 mL of MeOH and 3 mL of DCM. The racemic compound 38 was resolved by chiral HPLC using the following separation conditions:

Chiral preparative chromatography column: CHIRAL-PAK IC (trade name), 4.6 mm×250 mm (inner diameter× length), 5 μm (filler particle size)

Column temperature: 30° C.

Flow rate: 3.0 mL/min

UV detection wavelength: 254 nm

Mobile phase: MTBE:EOH=85:15

Compounds T-6-S (38 mg, retention time: 12.092 min, yield: 76%) and T-6-R (30 mg, retention time: 10.757 min, yield: 60%) were obtained. LC-MS (APCI): m/z=510.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 3.85 (s, 3H), 2.44 (br s, 2H).

Example 11

Preparation of 1-(4-fluorophenyl)-1-(2-(4-(6-(1-(methyl-d₃)-1H-pyrazol-4-yl)pyrrolo[2,1-f][1,2,4]triazin-4-yl)piperazin-1-yl-2,2,3,3,5,5,6,6-d₈)pyrimidin-5-yl)ethan-2,2,2-d₃-1-amine (Compound 40), (S)-1-(4-fluorophenyl)-1-(2-(4-(6-(1-(methyl-d₃)-1H-pyrazol-4-yl)pyrrolo[2,1-f][1,2,4]triazin-4-yl)piperazin-1-yl-2,2,3,3,5,5,6,6-d₈)pyrimidin-5-yl)ethan-2,2,2-d₃-1-amine (Compound T-7-S), and (R)-1-(4-fluorophenyl)-1-(2-(4-(6-(1-(methyl-d₃)-1H-pyrazol-4-yl)pyrrolo[2,1-f][1,2,4]triazin-4-yl)piperazin-1-yl-2,2,3,3,5,5,6,6-d₈)pyrimidin-5-yl)ethan-2,2,2-d₃-1-amine (Compound T-7-R)

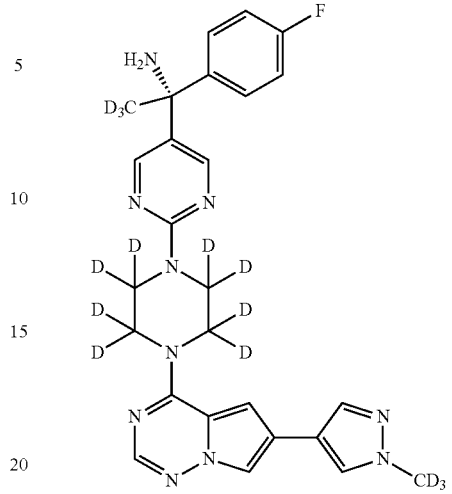

T-7-R

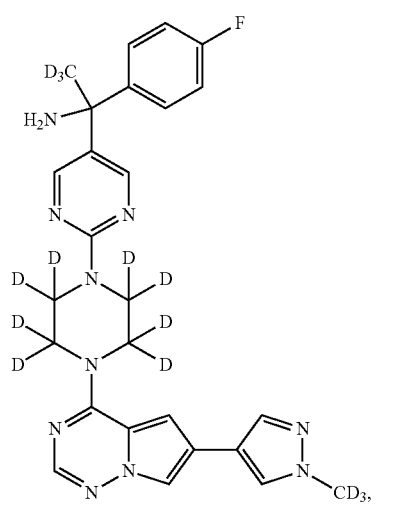

The following scheme was used for synthesis:

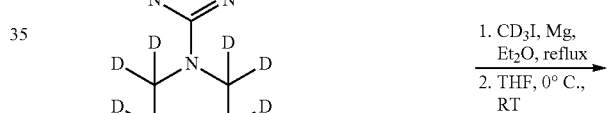

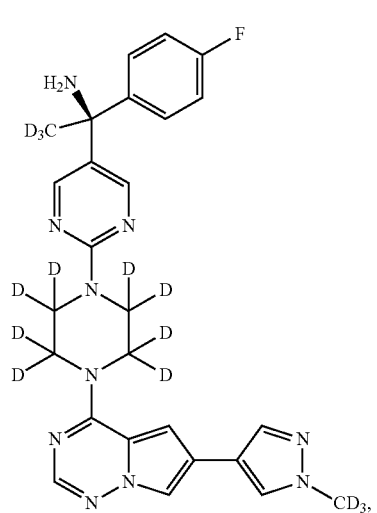

T-7-S

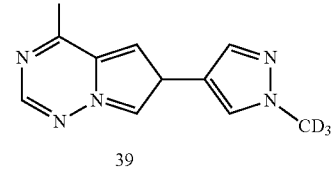

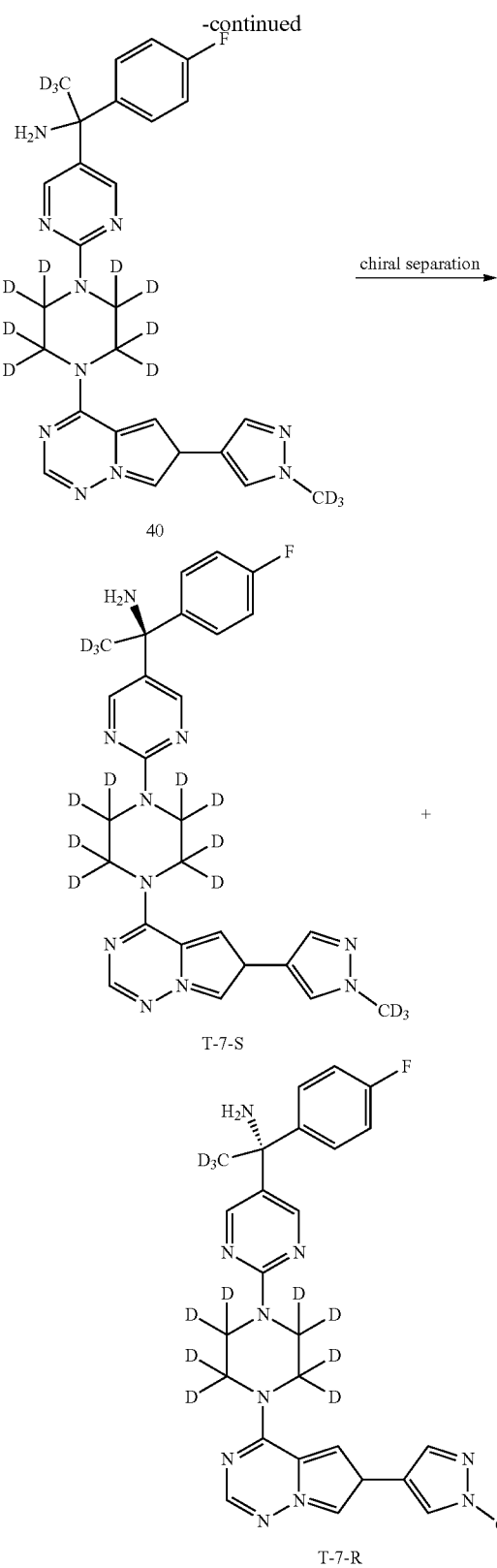

Step 1. Synthesis of Compound 39

Magnesium powder (140 mg, 5.79 mmol) was added to a 50 mL two-neck flask equipped with a magnetic stirrer and condenser tube, evacuated and protected with nitrogen, added with ethyl ether (5 mL) and deuterated methyl iodide (700 mg, 4.83 mmol) via a syringe, heated to reflux, stirred for reaction for 2 hours with the temperature kept, and cooled to room temperature.

Compound 35 (290 mg, 0.49 mmol) and anhydrous THF (5 mL) were added to another 50 mL two-neck flask equipped with a magnetic stirrer, stirred to dissolve to clear, evacuated and protected with nitrogen, cooled to 0° C., and slowly added dropwise with the solution of $CD_3MgI$ in ether prepared above. After the addition, the reaction was stirred at 0° C. for another 1 hour. The reaction was quenched with saturated aqueous ammonium chloride (5 mL), and extracted with ethyl acetate (10 mL×3). Organic phases were combined, washed with water (10 mL) and saturated brine (10 mL), dried over anhydrous sodium sulfate, filtered, concentrated and subjected to a silica gel column to obtain 180 mg of a white solid with a yield of 60.43%. LC-MS (APCI): m/z=617.3 (M+1)$^+$. $^1$H NMR (400 MHz, CDCl$_3$) δ/ppm: 8.35 (s, 1H), 8.31 (s, 1H), 7.91 (s, 1H), 7.72-7.70 (m, 2H), 7.57 (s, 1H), 7.38-7.34 (m, 2H), 7.07-7.01 (m, 2H), 6.79 (s, 1H), 3.78 (s, 1H), 1.22 (s, 9H).

Step 2. Synthesis of Compound 40

Compound 39 (160 mg, 0.26 mmol) and methanol (3 mL) were added to a 50 mL two-neck flask equipped with a magnetic stirrer, stirred to dissolve to clear, and added with a solution of hydrogen chloride in dioxane (3 mL, 4M). After the addition, the reaction was stirred under nitrogen atmosphere at room temperature for 1 hour. The solvent was evaporated under reduced pressure. Dichloromethane (15 mL) and saturated aqueous sodium bicarbonate (10 mL) were added, and stirred for 2 minutes. The organic layer was separated, and the aqueous phase was extracted with dichloromethane (15 mL×2). The organic phases were combined, dried over anhydrous sodium sulfate, filtered, and concentrated to obtain 100 mg of white solid with a yield of 75.48%. LC-MS(APCI): m/z=513.3 (M+1). $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 2.44 (br s, 2H).

Step 3. Synthesis of Compounds T-7-S and T-7-R 100 mg of compound 40 was dissolved in a mixed solvent of 30 mL of MeOH and 3 mL of DCM. The racemic compound 40 was resolved by chiral HPLC using the following separation conditions:

Chiral preparative chromatography column: CHIRALPAK IC (trade name), 4.6 mm×250 mm (inner diameter× length), 5 μm (filler particle size)

Column temperature: 30° C.

Flow rate: 3.0 mL/min

UV detection wavelength: 254 nm

Mobile phase: MTBE:EtOH=85:15

Compounds T-7-S (38 mg, retention time: 12.092 min, yield: 76%) and T-7-R (30 mg, retention time: 10.757 min, yield: 60%) were obtained. LC-MS(APCI): m/z=513.3 (M+1)$^+$. $^1$H NMR (300 MHz, DMSO-D$_6$) δ 8.38 (s, 2H), 8.00 (s, 1H), 7.95 (d, J=1.8 Hz, 1H), 7.84 (s, 1H), 7.78 (s, 1H), 7.46-7.41 (m, 2H), 7.20 (d, J=1.5 Hz, 1H), 7.11-7.05 (m, 1H), 2.44 (br s, 2H).

Biological Activity Tests (1) Kinase Activity Test

The ADP-Glo™ Kinase Assay kit (Promega, V9102) was used to determine the inhibitory activity of the test compounds on PDGFR α (D842V) (Signalchem, P12-12BG) and KIT (D816V) (Signalchem, C06-12LG).

Each compound was diluted in a 3-fold concentration gradient with DMSO (MP, 196055) to obtain 12 doses. The starting concentrations of the compounds were 10 mM and 0.1 mM, respectively. 100 nl diluent of the compound and 5 µL of PDGFR α (D842V) or KIT (D816V) were added to each well of a 384-well plate (Perkin Elmer, 6007290) in duplicate. After 15 minutes of incubation at 25° C., 5 µL of substrate was added to start the reaction, followed by incubation at 25° C. for 60 minutes. The final concentrations for reaction in the system were as follows: 4 nM PDGFR α (D842V), 15 µM ATP, 0.03 mg/mL MBP/1 nM KIT (D816V), 10 µM ATP, 0.1 mg/mL Poly (4:1 Glu, Tyr) Peptide, HEPES 50 mM, EGTA 1 mM, MgCl2 10 mM, and Brij35 0.01%. Test compound concentrations: 100, 33.3, 11.1, 3.7, 1.23, 0.41, 0.137, 0.046, 0.015, 0.0051 0.0017, 0.0006, 0 nM/1000, 333.33, 111.11, 37.04, 12.35, 4.12, 1.37, 0.46, 0.15, 0.051, 0.017, 0.006, 0 nM. Then 10 µL ADP Glo reagent was added, followed by incubation at 25° C. for another 40 minutes. Then 20 µL of detection reagent was added, and after incubation at 25° C. for 40 minutes, the enzyme activity in the presence of each concentration of compound was determined by Envision microplate reader (Perkin Elmer 2104) and the inhibitory effect of different concentrations of the compound on enzyme activity was calculated. Afterwards, according to the four-parameter equation and using Graphpad 5.0 software, the inhibition data of the enzyme activity were fitted to the different concentrations of the compound to calculate the $IC_{50}$ value. The data of representative example compounds tested in the assay are presented in Table 1, where A means $IC_{50}<1$ nM, B means $1\ nM \leq IC_{50}<50$ nM, C means $50\ nM \leq IC_{50}<200$ nM, and D means $IC_{50} \geq 200$ nM.

The compounds of the present invention and the non-deuterated compound Avapritinib were tested in the above-mentioned kinase inhibition experiment, and it was found that compared with Avapritinib, the compounds of the present invention had more potent activities on PDGFR α (D824V) and fairly potent activities on Kit(D816V).

(2) Cytotoxicity Test

Cell line: Ba/F3 Kit D816V (3000 cells/well; cell type: suspension; medium: RPMI-1640+10% FBS), incubated at 37° C., 5% $CO_2$, and 95% humidity.

Reagents and materials: Fetal Bovine Serum FBS (GBICO, Cat #10099-141); CellTiter-Glo® Luminescent Cell Viability Assay (Promega, Cat #G7572); 96-well transparent flat-bottomed black-walled plate (Corning®, Cat #3603) Control compound: Sunitinib (Selleck, Cat #S7781)

Cell culture and seeding: the cells in the logarithmic growth phase were harvested and counted using a platelet counter, the cell viability was determined using the trypan blue exclusion method to ensure that the cell viability was above 90%; the cell concentration was adjusted; 90 µL of cell suspension was added to a 96-well plate; and the cells in the 96-well plate were incubated overnight at 37° C., 5% $CO_2$, and 95% humidity.

Drug dilution and dosing: a 10-fold drug solution was prepared, the highest concentration being 3 µM, and 9 concentrations were obtained with 3.16-fold dilution; 10 µL of drug solution was added to each well of the 96-well plate seeded with cells, in triplicate for each drug concentration; and the cells in the 96-well plate with the drug added were incubated at 37° C., 5% C02, and 95% humidity for another 72 hours, followed by CTG analysis.

End-point plate reading: the CTG reagent was melted and the cell plate was equilibrated to room temperature for 30 minutes; an equal volume of CTG solution was added to each well; shaking on an orbital shaker for 5 minutes was made to lyse the cells; the cell plate was placed at room temperature for 20 minutes to stabilize the luminescence signal; and the luminescence values were read.

Data processing: GraphPad Prism 5.0 software was used to analyze the data; nonlinear S-curve regression was used to fit the data to obtain the dose-effect curve, and thereby calculate the $IC_{50}$ values. The data of representative example compounds tested in the assay are presented in Table 1, where A means $IC_{50}<1$ nM, B means $1\ nM \leq IC_{50}<50$ nM, C means $50\ nM \leq IC_{50}<200$ nM, and D means $IC_{50} \geq 200$ nM.

Cell survival rate (%)=
$(Lum_{tested\ drug} - Lum_{medium\ control}) / (Lum_{cell\ control} - Lum_{medium\ control}) \times 100\%$.

In the above cytotoxicity experiment, the compounds of the present invention and the non-deuterated compound Avapritinib were tested, and it was found that the compounds of the present invention had potent activities on BaF3[Kit(D816V)].

TABLE 1

|  | Kinase $IC_{50}$ (nM) | | Cell $IC_{50}$ (nM) |
|---|---|---|---|
|  | PDGFR α(D824V) | Kit(D816V) | BaF3/Kit(D816V) |
| Avapritinib | B | A | B |
| T-1-S | A | A | B |
| T-2-S | A | A | B |
| T-3-S | A | A | B |
| T-4-S | A | A | B |
| T-5-S | A | A | B |
| T-6-S | A | A | B |
| T-7-S | A | A | B |

(3) Metabolic Stability Evaluation

Microsome experiment: human liver microsome: 0.5 mg/mL, Xenotech; rat liver microsome: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solution: a certain amount of the example compound powder and control compound powder were accurately weighed, and respectively dissolved to 5 mM with DMSO.

Preparation of phosphate buffer (100 mM, pH7.4): 150 mL of 0.5M potassium dihydrogen phosphate and 700 mL of 0.5M dipotassium hydrogen phosphate prepared beforehand were mixed, with pH of the mixture adjusted to 7.4 with 0.5M dipotassium hydrogen phosphate solution. Before use, the mixture was diluted by 5 folds with ultrapure water and magnesium chloride was added to obtain the phosphate buffer (100 mM), which contains 100 mM potassium phosphate, 3.3 mM magnesium chloride, and has pH 7.4.

NADPH regeneration system solution (containing 6.5 mM NADP, 16.5 mM G-6-P, 3 U/mL G-6-P D, 3.3 mM magnesium chloride) was prepared, and placed on wet ice before use.

Preparation of stop solution: a solution of 50 ng/mL propranolol hydrochloride and 200 ng/mL tolbutamide (internal standard) in acetonitrile. 25057.5 µL of phosphate buffer (pH 7.4) was taken into a 50 mL centrifuge tube, added with 812.5 µL of human liver microsome, and mixed well to obtain a liver microsome diluent with a protein concentration of 0.625 mg/mL. 25057.5 μL of phosphate buffer (pH 7.4) was taken into a 50 mL centrifuge tube, added with 812.5 μL of SD rat liver microsome, and mixed well to obtain a liver microsome diluent with a protein concentration of 0.625 mg/mL.

Incubation of the samples: the stock solutions of the corresponding compounds were respectively diluted to 0.25 mM with an aqueous solution containing 70% acetonitrile to obtain working solutions for later use. 398 μL of human liver microsome and rat liver microsome diluents were respectively taken and added to a 96-well incubation plate (N=2), added with 2 μL of 0.25 mM working solution respectively, and mixed well.

Determination of metabolic stability: 300 μL of pre-cooled stop solution was added to each well of a 96-well deep-well plate, and the plate was placed on ice as a stop plate. The 96-well incubation plate and the NADPH regeneration system were placed in a 37° C. water bath, shaken at 100 rpm, and pre-incubated for 5 minutes. 80 μL of incubation solution was taken out of each well of the incubation plate and added to the stop plate, mixed well, and supplemented with 20 μL of NADPH regeneration system solution to obtain the 0 min sample. Then 80 μL of NADPH regeneration system solution was added to each well of the incubation plate to initiate the reaction and start timing. The reaction concentration of the corresponding compound was 1 μM, and the protein concentration was 0.5 mg/mL. At 10, 30, and 90 minutes of reaction, 100 μL of the reaction solution was taken and added to the stop plate, and vortexed for 3 minutes to stop the reaction. The stop plate was centrifuged at 5000×g for 10 min at 4° C. 100 μL of supernatant was taken to a 96-well plate pre-added with 100 μL of distilled water, mixed well, and subjected to sample analysis by LC-MS/MS.

Data analysis: the peak areas of the corresponding compound and internal standard were detected through the LC-MS/MS system, and the ratio of the peak area of the compound to the internal standard was calculated. The natural logarithm of the remaining percentage of the compound was plotted against time to measure the slope and calculate $t_{1/2}$ and $CL_{int}$ according to the following equations, where V/M is equal to 1/protein concentration.

$$t_{1/2} = -\frac{0.693}{\text{Slope}}, \quad CL_{int} = \frac{0.693}{t_{1/2}} \cdot \frac{V}{M}, \quad t_{1/2}(\text{min}); \; CL_{int}(\mu L/\text{min}/\text{mg})$$

The compounds of the present invention and the corresponding non-deuterated compounds were simultaneously tested for comparison and evaluated for the metabolic stability in human and rat liver microsomes. The non-deuterated compound Avapritinib was used as the control. In human and rat liver microsomal experiments, the compounds of the present invention significantly improved metabolic stability, as compared with the non-deuterated compound Avapritinib and (R)-1-(4-fluorophenyl)-1-(2-(4-(6-(1-methyl-1H-pyrazol-4-yl)pyrrolo[2,1-f][1,2,4]triazin-4-yl)piperazin-1-yl)pyrimidin-5-yl)ethan-1-amine (Compound A). The experimental results of representative example compounds in liver microsomes are summarized in Table 2 below.

TABLE 2

|  | human liver microsome experiment | | rat liver microsome experiment | |
|---|---|---|---|---|
|  | T½ (min) | CL (μL/min/mg) | T½ (min) | CL (μL/min/mg) |
| Avapritinib | 87.6 | 15.8 | 56.3 | 24.6 |
| T-1-S | 88.6 | 15.6 |  |  |
| T-3-S | 106.6 | 13 | 89.1 | 15.6 |
| T-4-S | 90.5 | 15.3 | 81.1 | 17.1 |
| T-6-S | 105.4 | 13.1 | 89.4 | 15.5 |
| Compound A | 48.1 | 28.8 | 33.4 | 41.5 |
| T-3-R | 51.3 | 27 | 37.3 | 37.2 |
| T-4-R | 53.3 | 26 | 51.4 | 27 |
| T-6-R | 57.3 | 24.2 | 35.9 | 38.6 |

(4) Rat Pharmacokinetics Experiment 6 male Sprague-Dawley rats, 7-8 weeks old, weighing about 210 g, were divided into 2 groups, 3 rats in each group, and a single dose of the compound (10 mg/kg orally) was administered intravenously or orally to compare the pharmacokinetics.

The rats were fed with standard feed and given water, and fasting began 16 hours before the test. The drug was dissolved with PEG400 and dimethyl sulfoxide. Blood was collected from the orbit. The time points for blood collection were 0.083, 0.25, 0.5, 1, 2, 4, 6, 8, 12, and 24 hours after administration.

The rats were briefly anesthetized after inhaling ether, and a blood sample of 300 μL was collected from the orbit in a test tube. There was 30 μL of 1% heparin salt solution in the test tube. Before use, the test tube was dried overnight at 60° C. After the blood sample was collected at the last time point, the rats were anesthetized with ether and sacrificed.

Immediately after the blood sample was collected, the test tube was gently inverted at least 5 times to ensure thorough mixing and then placed on ice. The blood sample was centrifuged at 5000 rpm for 5 minutes at 4° C. to separate the plasma from the red blood cells. 100 μL of plasma was transferred with a pipette into a clean plastic centrifuge tube, labeled with the name of the compound and the time point. The plasma was stored at −80° C. before analysis. The concentration of the compound of the invention in the plasma was determined by LC-MS/MS. The pharmacokinetic parameters were calculated based on the blood drug concentrations of each animal at different time points.

Experiments showed that the compounds of the present invention had better pharmacokinetic properties in animals.

The above content is a further detailed description of the present invention in conjunction with specific preferred embodiments, and it cannot be considered that the specific implementation of the present invention is just limited to the description. For those of ordinary skill in the technical field to which the present invention belongs, a number of simple deductions or substitutions can be made without departing from the concept of the present invention, which should be regarded as falling within the protection scope of the present invention.

The invention claimed is:
1. A compound selected from the group consisting of:
T-1-S
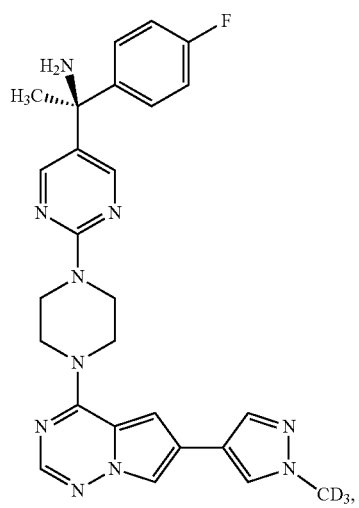
T-2-S
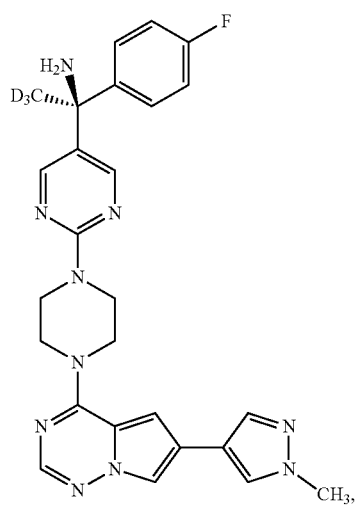
T-3-S
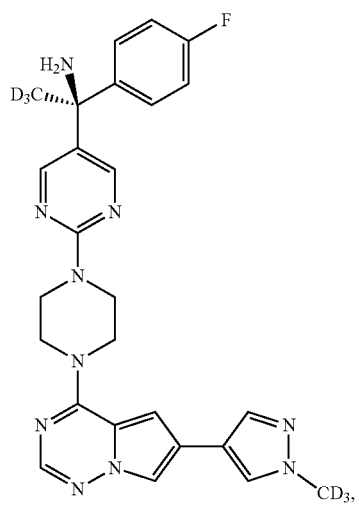
T-4-S
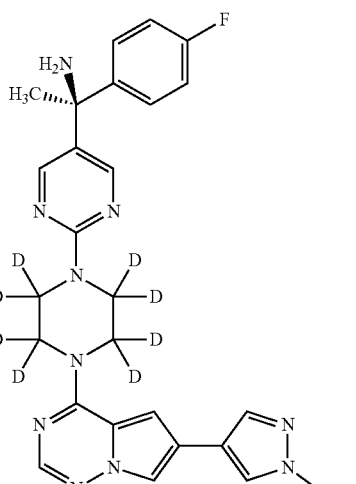
T-5-S
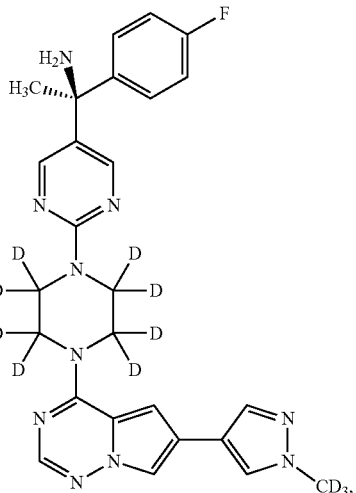
T-6-S
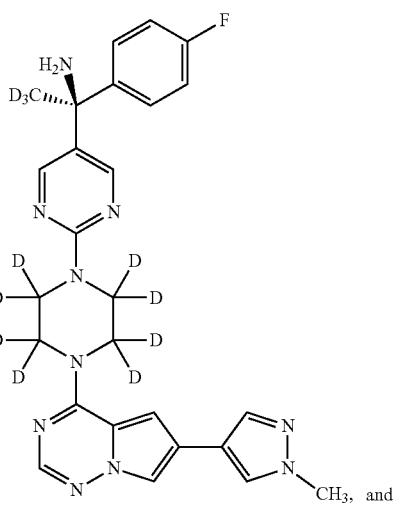
and

-continued

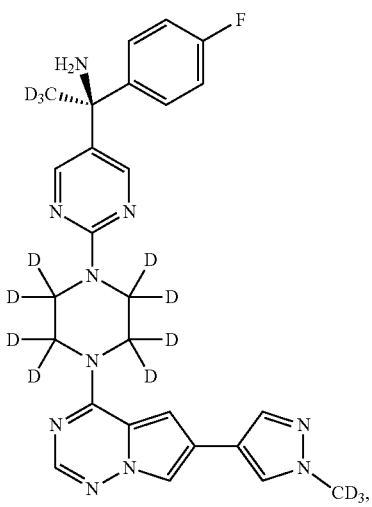

T-7-S or a pharmaceutically acceptable salt thereof.

2. The compound according to claim 1, wherein the compound is:

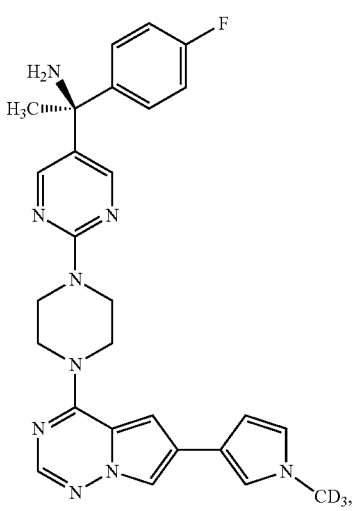

T-1-S or a pharmaceutically acceptable salt thereof.

3. The compound according to claim 1, wherein the compound is:

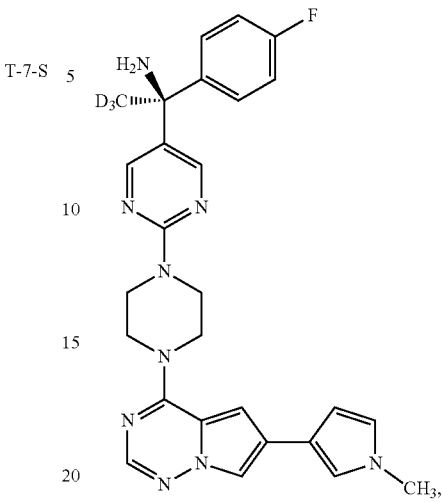

T-2-S or a pharmaceutically acceptable salt thereof.

4. A pharmaceutical composition comprising a pharmaceutically acceptable excipient and a compound according to claim 1, or a pharmaceutically acceptable salt thereof.

5. The pharmaceutical composition according to claim 4, wherein the pharmaceutical composition further comprises at least one additional therapeutic agent.

6. A method for inhibiting platelet-derived growth factor receptor alpha activity in a subject, wherein the method comprises administering to the subject in need thereof an effective amount of a compound according to claim 1, or a pharmaceutically acceptable salt thereof.

7. The method according to claim 6, wherein the subject has a disease mediated by platelet-derived growth factor receptor alpha selected from the group consisting of acute myeloid leukemia, a gastrointestinal stromal tumor and mastocytosis.

8. The method according to claim 6, wherein the platelet-derived growth factor receptor alpha has a mutation in exon 18.

9. The method according to claim 6, wherein the platelet-derived growth factor receptor alpha has a mutation at residue 842.

10. A method for inhibiting platelet-derived growth factor receptor alpha activity in a subject, wherein the method comprises administering to the subject in need thereof an effective amount of the pharmaceutical composition according to claim 4.

11. The method according to claim 10, wherein the subject has a disease mediated by platelet-derived growth factor receptor alpha selected from the group consisting of acute myeloid leukemia, a gastrointestinal stromal tumor and mastocytosis.

12. The method according to claim 10, wherein the platelet-derived growth factor receptor alpha has a mutation in exon 18.

13. The method according to claim 10, wherein the platelet-derived growth factor receptor alpha has a mutation at residue 842.

* * * * *